United States Patent
Hanuka et al.

(10) Patent No.: US 10,524,953 B2
(45) Date of Patent: Jan. 7, 2020

(54) COMPACT OSTOMY APPLIANCE

(71) Applicant: B. Braun Medical SAS, Boulogne-Billancourt (FR)

(72) Inventors: David Hanuka, Ramat-Yishai (IL); Meir Or, Doar-Na Misgav (IL); Refael Sommer, Nesher (IL); Tamir Shavit, Doar-Na Galil Maaravi (IL)

(73) Assignee: B. Braun Medical SAS, Saint-Cloud (FR)

( * ) Notice: Subject to any disclaimer, the term of this patent is extended or adjusted under 35 U.S.C. 154(b) by 753 days.

(21) Appl. No.: 14/890,003

(22) PCT Filed: May 8, 2014

(86) PCT No.: PCT/IL2014/050416
§ 371 (c)(1),
(2) Date: Mar. 21, 2016

(87) PCT Pub. No.: WO2014/181338
PCT Pub. Date: Nov. 13, 2014

(65) Prior Publication Data
US 2016/0113810 A1   Apr. 28, 2016

Related U.S. Application Data

(63) Continuation-in-part of application No. 13/890,433, filed on May 9, 2013, now Pat. No. 9,345,612, and a
(Continued)

(51) Int. Cl.
*A61F 5/44*    (2006.01)
*B31B 50/26*   (2017.01)
(Continued)

(52) U.S. Cl.
CPC .............. *A61F 5/4407* (2013.01); *A61F 5/441* (2013.01); *A61F 5/4401* (2013.01); *A61F 5/442* (2013.01);
(Continued)

(58) Field of Classification Search
CPC .................. A61F 5/4404; A61F 5/4407; A61F 2005/4402; A61F 2005/4415; A61F 5/445;
(Continued)

(56) References Cited

U.S. PATENT DOCUMENTS 2,243,529 A    5/1941   Grossman et al.
2,341,984 A    2/1944   Graves
(Continued)

FOREIGN PATENT DOCUMENTS

CN    1694661 A     11/2005
DE    19921555 A1    2/2000
(Continued)

OTHER PUBLICATIONS

International Preliminary Report on Patentability for International Application No. PCT/IL2013/050401, dated Nov. 11, 2014 (10 pages).
(Continued)

*Primary Examiner* — Susan S Su
(74) *Attorney, Agent, or Firm* — Clark & Elbing LLP

(57) ABSTRACT

Ostomy appliance components providing low profile containment of waste from a surgical stoma. Waste collection pouch configuration, positioning, and positioning structure relate to potential advantages in manufacturing and operation of components.

35 Claims, 32 Drawing Sheets

Related U.S. Application Data continuation-in-part of application No. PCT/IL2013/050401, filed on May 9, 2013.

(60) Provisional application No. 61/903,523, filed on Nov. 13, 2013, provisional application No. 61/884,256, filed on Sep. 30, 2013.

(51) Int. Cl.
*A61F 5/445* (2006.01)
*A61F 5/442* (2006.01)
*A61F 5/441* (2006.01)
*A61F 5/448* (2006.01)

(52) U.S. Cl.
CPC .......... *A61F 5/4404* (2013.01); *A61F 5/4405* (2013.01); *A61F 5/445* (2013.01); *A61F 5/448* (2013.01); *B31B 50/26* (2017.08); *A61F 2005/4402* (2013.01); *A61F 2005/4415* (2013.01)

(58) Field of Classification Search
CPC .. A61F 5/448; A61F 5/449; A61F 2005/4455; A61F 2005/4483; A61F 2005/4486; A61F 2005/4495
See application file for complete search history.

(56) References Cited

U.S. PATENT DOCUMENTS

| | | |
|---|---|---|
| 2,510,766 A | 6/1950 | Surface |
| 2,544,579 A | 3/1951 | Ardner |
| 2,639,710 A | 5/1953 | Fazio |
| 2,667,167 A | 1/1954 | Raiche |
| 2,971,510 A | 2/1961 | Berger |
| 3,398,744 A | 8/1968 | Hooper |
| 3,447,533 A | 6/1969 | Spicer |
| 3,718,141 A | 2/1973 | Goetz |
| 3,976,076 A | 8/1976 | Beach |
| 4,030,500 A | 6/1977 | Ronnquist |
| 4,121,589 A | 10/1978 | McDonnell |
| 4,170,231 A | 10/1979 | Collins |
| 4,183,357 A | 1/1980 | Bentley et al. |
| 4,209,010 A | 6/1980 | Ward et al. |
| 4,210,131 A | 7/1980 | Perlin |
| 4,211,224 A | 7/1980 | Kubach et al. |
| 4,217,664 A | 8/1980 | Faso |
| 4,232,672 A | 11/1980 | Steer et al. |
| 4,233,325 A | 11/1980 | Slangan et al. |
| 4,265,244 A | 5/1981 | Hill |
| 4,338,937 A | 7/1982 | Lerman |
| 4,344,434 A | 8/1982 | Robertson |
| 4,351,322 A | 9/1982 | Prager |
| 4,381,765 A | 5/1983 | Burton |
| 4,399,809 A | 8/1983 | Baro et al. |
| 4,421,124 A | 12/1983 | Marshall |
| 4,460,363 A | 7/1984 | Steer et al. |
| 4,462,510 A | 7/1984 | Steer et al. |
| 4,516,974 A | 5/1985 | Davis |
| 4,534,761 A | 8/1985 | Raible |
| 4,634,421 A | 1/1987 | Hegemann |
| 4,642,107 A | 2/1987 | Arnone et al. |
| 4,662,890 A | 5/1987 | Burton |
| 4,721,508 A | 1/1988 | Burton |
| 4,786,283 A | 11/1988 | Andersson |
| 4,804,375 A | 2/1989 | Robertson |
| 4,810,250 A | 3/1989 | Ellenberg et al. |
| 4,834,731 A | 5/1989 | Nowak et al. |
| 4,854,316 A | 8/1989 | Davis |
| 4,863,447 A | 9/1989 | Smith |
| 4,941,869 A | 7/1990 | D'amico |
| 4,950,223 A | 8/1990 | Silvanov |
| 4,981,465 A | 1/1991 | Ballan et al. |
| 5,004,464 A | 4/1991 | Leise, Jr. |
| 5,026,360 A | 6/1991 | Johnsen et al. |
| 5,045,052 A | 9/1991 | Sans |
| D323,213 S | 1/1992 | Iacone |
| 5,108,430 A | 4/1992 | Ravo |
| 5,125,916 A | 6/1992 | Panebianco et al. |
| 5,135,519 A | 8/1992 | Helmer |
| 5,163,897 A | 11/1992 | Persky |
| 5,163,930 A | 11/1992 | Blum |
| 5,236,426 A | 8/1993 | Schottes et al. |
| 5,250,057 A | 10/1993 | Chen |
| 5,261,898 A | 11/1993 | Polin et al. |
| 5,269,774 A | 12/1993 | Gray |
| 5,372,594 A | 12/1994 | Colacello et al. |
| D354,560 S | 1/1995 | Chase |
| 5,401,264 A | 3/1995 | Leise, Jr. |
| 5,501,678 A | 3/1996 | Olsen |
| 5,549,588 A | 8/1996 | Johnsen |
| 5,569,216 A | 10/1996 | Kim |
| 5,658,266 A | 8/1997 | Colacello et al. |
| 5,658,267 A | 8/1997 | Colacello et al. |
| 5,672,163 A | 9/1997 | Ferreira et al. |
| 5,683,372 A | 11/1997 | Colacello et al. |
| 5,693,035 A | 12/1997 | Leise, Jr. et al. |
| 5,771,590 A | 6/1998 | Colacello et al. |
| 5,785,677 A | 7/1998 | Auweiler |
| 5,785,695 A | 7/1998 | Sato et al. |
| 5,947,942 A | 9/1999 | Galjour |
| 6,033,390 A | 3/2000 | von Dyck |
| D422,357 S | 4/2000 | Niedospial, Jr. et al. |
| 6,050,982 A | 4/2000 | Wheeler |
| 6,071,268 A | 6/2000 | Wagner |
| 6,329,465 B1 | 12/2001 | Takahashi et al. |
| 6,350,255 B1 | 2/2002 | von Dyck |
| 6,357,445 B1 | 3/2002 | Shaw |
| 6,481,589 B2 | 11/2002 | Blomdahl et al. |
| 6,485,476 B1 | 11/2002 | von Dyck et al. |
| 6,543,453 B1 | 4/2003 | Klima et al. |
| 6,589,222 B1 | 7/2003 | Olsen |
| 6,595,971 B1 | 7/2003 | von Dyck et al. |
| 6,659,988 B1 | 12/2003 | Steer et al. |
| 6,689,111 B2 | 2/2004 | Mulhauser et al. |
| 6,695,825 B2 | 2/2004 | Castles |
| 6,723,079 B2 | 4/2004 | Cline |
| 6,963,772 B2 | 11/2005 | Bloom et al. |
| 7,001,367 B2 | 2/2006 | Arkinstall |
| D516,714 S | 3/2006 | McAllister et al. |
| 7,083,569 B2 | 8/2006 | Boulanger et al. |
| 7,087,041 B2 | 8/2006 | von Dyck et al. |
| 7,250,040 B2 * | 7/2007 | Andersen ............... A61F 5/445 604/332 |
| 7,258,661 B2 | 8/2007 | Davies et al. |
| 7,314,443 B2 | 1/2008 | Jordan et al. |
| 7,582,072 B2 | 9/2009 | McMichael |
| 7,628,767 B1 | 12/2009 | Simmons et al. |
| 7,670,289 B1 | 3/2010 | McCall |
| 7,704,240 B2 * | 4/2010 | Buhl ....................... A61F 5/445 604/327 |
| 7,722,586 B2 | 5/2010 | Mullejans et al. |
| 7,857,796 B2 | 12/2010 | Cline et al. |
| 7,867,207 B2 | 1/2011 | Therkelsen et al. |
| 7,946,417 B2 | 5/2011 | Plishka et al. |
| 7,976,522 B2 | 7/2011 | Hansen et al. |
| 8,070,737 B2 | 12/2011 | Cline et al. |
| 8,092,437 B2 | 1/2012 | Cline |
| 8,100,875 B2 | 1/2012 | Cline et al. |
| 8,142,406 B2 | 3/2012 | Blum |
| 8,217,221 B2 | 7/2012 | Davies et al. |
| 8,372,015 B2 | 2/2013 | Escutia et al. |
| 8,388,586 B2 | 3/2013 | Weig |
| D685,094 S | 6/2013 | Green et al. |
| 8,460,259 B2 | 6/2013 | Tsai |
| D687,144 S | 7/2013 | Gronberg |
| 8,657,799 B2 | 2/2014 | Carrubba |
| 8,690,848 B2 | 4/2014 | Cason |
| D710,977 S | 8/2014 | Chen |
| 8,821,464 B2 | 9/2014 | Hanuka et al. |
| 8,821,465 B2 | 9/2014 | Hanuka et al. |
| 8,845,607 B2 | 9/2014 | Hanuka et al. |
| 8,858,519 B2 | 10/2014 | Hanuka et al. |
| 8,864,729 B2 | 10/2014 | Hanuka et al. |

(56) References Cited

U.S. PATENT DOCUMENTS

| | | | |
|---|---|---|---|
| 8,900,116 | B2 | 12/2014 | Hanuka et al. |
| 8,998,862 | B2 | 4/2015 | Hanuka et al. |
| D728,759 | S | 5/2015 | Gonzalez |
| D739,012 | S | 9/2015 | Hanuka et al. |
| D739,525 | S | 9/2015 | Hanuka et al. |
| D741,996 | S | 10/2015 | Strong et al. |
| D743,552 | S | 11/2015 | Bronnimann et al. |
| 9,314,365 | B2 | 4/2016 | Hanuka et al. |
| 9,345,612 | B2 | 5/2016 | Hanuka et al. |
| 9,517,157 | B2 | 12/2016 | Hanuka et al. |
| D783,814 | S | 4/2017 | Hanuka et al. |
| D796,029 | S | 8/2017 | Hanuka et al. |
| 9,801,754 | B2 * | 10/2017 | Masters ............... A61F 5/4407 |
| 9,883,964 | B2 | 2/2018 | Hanuka et al. |
| 9,987,160 | B2 | 6/2018 | Hanuka et al. |
| 2002/0077611 | A1 | 6/2002 | von Dyck et al. |
| 2003/0004477 | A1 | 1/2003 | Nielsen et al. |
| 2003/0150050 | A1 | 8/2003 | Tanaka et al. |
| 2003/0187393 | A1 | 10/2003 | Cline |
| 2003/0199783 | A1 | 10/2003 | Bloom et al. |
| 2003/0220621 | A1 | 11/2003 | Arkinstall |
| 2004/0029467 | A1 | 2/2004 | Lacroix |
| 2004/0073179 | A1 | 4/2004 | Andersen |
| 2004/0122527 | A1 | 6/2004 | Imran |
| 2004/0167376 | A1 | 8/2004 | Peters et al. |
| 2004/0171999 | A1 | 9/2004 | Andersen et al. |
| 2004/0181197 | A1 | 9/2004 | Cline |
| 2004/0193122 | A1 | 9/2004 | Cline et al. |
| 2005/0027159 | A1 | 2/2005 | Feng et al. |
| 2005/0054996 | A1 | 3/2005 | Gregory |
| 2005/0065488 | A1 | 3/2005 | Elliott |
| 2005/0104457 | A1 | 5/2005 | Jordan et al. |
| 2005/0115857 | A1 | 6/2005 | Homann |
| 2005/0175665 | A1 | 8/2005 | Hunter et al. |
| 2005/0186244 | A1 | 8/2005 | Hunter et al. |
| 2005/0187140 | A1 | 8/2005 | Hunter et al. |
| 2005/0196421 | A1 | 9/2005 | Hunter et al. |
| 2005/0208095 | A1 | 9/2005 | Hunter et al. |
| 2006/0048283 | A1 | 3/2006 | Sorensen |
| 2006/0058576 | A1 | 3/2006 | Davies et al. |
| 2006/0106354 | A1 | 5/2006 | Vantroostenberghe |
| 2006/0111682 | A1 | 5/2006 | Schena et al. |
| 2006/0206069 | A1 | 9/2006 | Cline |
| 2006/0229596 | A1 | 10/2006 | Weiser et al. |
| 2007/0049878 | A1 | 3/2007 | Kim et al. |
| 2007/0088300 | A1 | 4/2007 | Cline et al. |
| 2007/0123832 | A1 | 5/2007 | Cline et al. |
| 2007/0129695 | A1 | 6/2007 | Blum |
| 2007/0142780 | A1 | 6/2007 | Van Lue |
| 2007/0191794 | A1 | 8/2007 | Cline et al. |
| 2007/0219532 | A1 | 9/2007 | Karpowicz et al. |
| 2007/0260206 | A1 | 11/2007 | Mullejans et al. |
| 2007/0276346 | A1 | 11/2007 | Poulsen et al. |
| 2008/0004580 | A1 | 1/2008 | Mullejans et al. |
| 2008/0015405 | A1 | 1/2008 | Davies et al. |
| 2008/0033380 | A1 | 2/2008 | Andersen |
| 2008/0091154 | A1 | 4/2008 | Botten |
| 2008/0108862 | A1 | 5/2008 | Jordan et al. |
| 2008/0135044 | A1 | 6/2008 | Freitag et al. |
| 2008/0269698 | A1 | 10/2008 | Alexander et al. |
| 2008/0275410 | A1 | 11/2008 | Burt |
| 2009/0043151 | A1 | 2/2009 | Gobel |
| 2009/0076532 | A1 | 3/2009 | Rebuffat et al. |
| 2009/0138030 | A1 | 5/2009 | Gronberg |
| 2009/0216206 | A1 | 8/2009 | Nishtala et al. |
| 2009/0247969 | A1 | 10/2009 | Nishtala et al. |
| 2010/0069859 | A1 | 3/2010 | Weig |
| 2010/0174253 | A1 | 7/2010 | Cline et al. |
| 2010/0241092 | A1 | 9/2010 | Nguyen-DeMary et al. |
| 2011/0015475 | A1 | 1/2011 | Hanuka et al. |
| 2011/0040231 | A1 | 2/2011 | Gregory |
| 2011/0040269 | A1 | 2/2011 | Cline |
| 2011/0106032 | A1 | 5/2011 | Kratky |
| 2012/0059341 | A1 | 3/2012 | Masters |
| 2012/0109086 | A1 | 5/2012 | Tsai |
| 2012/0136324 | A1 | 5/2012 | Hanuka et al. |
| 2012/0179124 | A1 | 7/2012 | Nguyen-Demary et al. |
| 2012/0215188 | A1 | 8/2012 | Salama |
| 2012/0245535 | A1 | 9/2012 | Jacobsson et al. |
| 2013/0053802 | A1 | 2/2013 | Maidl et al. |
| 2013/0053803 | A1 | 2/2013 | Willoughby et al. |
| 2013/0060212 | A1 * | 3/2013 | Hanuka ............... A61F 5/445 604/333 |
| 2013/0060214 | A1 | 3/2013 | Willoughby et al. |
| 2013/0072886 | A1 | 3/2013 | Schertiger et al. |
| 2013/0116642 | A1 | 5/2013 | Hanuka et al. |
| 2013/0304008 | A1 | 11/2013 | Hanuka et al. |
| 2014/0148770 | A1 * | 5/2014 | Masters ............... A61F 5/4407 604/344 |
| 2014/0194844 | A1 | 7/2014 | Edvardsen et al. |
| 2015/0025488 | A1 | 1/2015 | Hanuka et al. |
| 2015/0057626 | A1 | 2/2015 | Hanuka et al. |
| 2015/0141944 | A1 | 5/2015 | Hanuka et al. |
| 2015/0305916 | A1 | 10/2015 | Hanuka et al. |
| 2015/0359657 | A1 | 12/2015 | Argent et al. |
| 2015/0359658 | A1 | 12/2015 | Leise, Jr. |
| 2016/0166424 | A1 | 6/2016 | Hanuka et al. |
| 2017/0143533 | A1 | 5/2017 | Schertiger et al. |

FOREIGN PATENT DOCUMENTS

| | | |
|---|---|---|
| DE | 102004001631 A1 | 8/2004 |
| DE | 102007062133 B3 | 7/2009 |
| EP | 1795157 A2 | 6/2007 |
| EP | 2027835 A1 | 2/2009 |
| FR | 2870112 A1 | 11/2005 |
| GB | 2094153 A | 9/1982 |
| JP | 2006-314479 A | 11/2006 |
| JP | 2008-507308 A | 3/2008 |
| WO | 87/03192 A1 | 6/1987 |
| WO | 90/07311 A1 | 7/1990 |
| WO | 96/32904 A1 | 10/1996 |
| WO | 99/43277 A1 | 9/1999 |
| WO | 01/49224 A1 | 7/2001 |
| WO | 02/058603 A1 | 8/2002 |
| WO | 03/065945 A1 | 8/2003 |
| WO | 03/071997 A1 | 9/2003 |
| WO | 2006/010556 A1 | 2/2006 |
| WO | 2007/030703 A2 | 3/2007 |
| WO | 2008/048856 A2 | 4/2008 |
| WO | 2008/103789 A2 | 8/2008 |
| WO | 2008/141180 A1 | 11/2008 |
| WO | 2009/083183 A2 | 7/2009 |
| WO | 2009/155537 A1 | 12/2009 |
| WO | 2011/007355 A2 | 1/2011 |
| WO | 2011/013872 A1 | 2/2011 |
| WO | 2011/039517 A1 | 4/2011 |
| WO | 2011/057635 A1 | 5/2011 |
| WO | 2011/138727 A1 | 11/2011 |
| WO | 2011/138728 A2 | 11/2011 |
| WO | 2011/138730 A1 | 11/2011 |
| WO | 2011/138731 A2 | 11/2011 |
| WO | 2013/022487 A1 | 2/2013 |
| WO | 2014/081889 A1 | 5/2014 |
| WO | 2014/181339 A2 | 11/2014 |

OTHER PUBLICATIONS

International Search Report and Written Opinion for International Application No. PCT/IL2013/050401, dated Dec. 20, 2013 (17 pages).

International Search Report for International Application No. PCT/IL2014/050416, dated Dec. 19, 2014 (7 pages).

Written Opinion for International Application No. PCT/IL2014/050416, dated Dec. 19, 2014 (11 pages).

Zhang et al., "Occlusion effect comparison of artificial silicone rubber closure devices with different diameters," Chinese Journal of Tissue Engineering Research. 16(8):1496-1500 (2012). Abstract in English.

\* cited by examiner

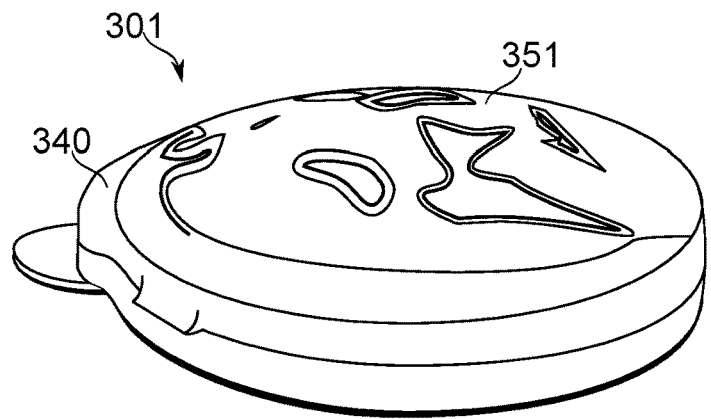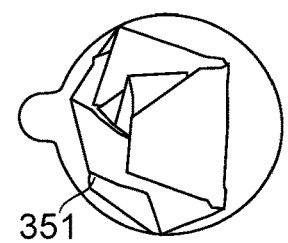
FIG. 3B
FIG. 3A
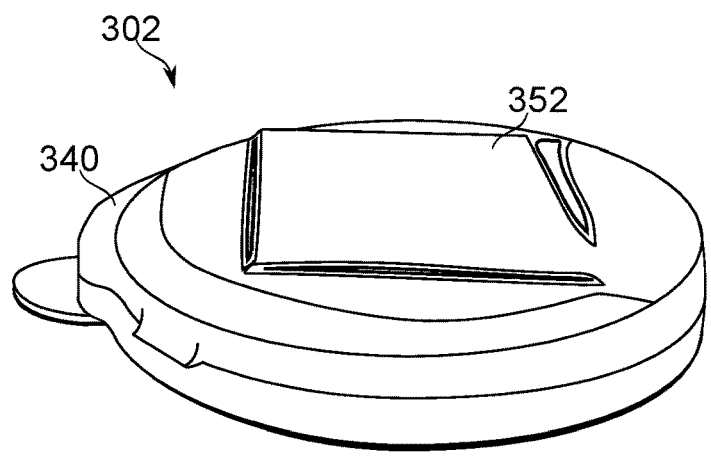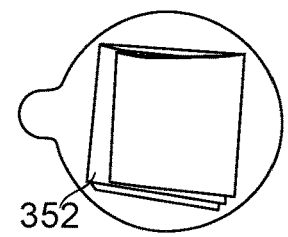
FIG. 3D
FIG. 3C

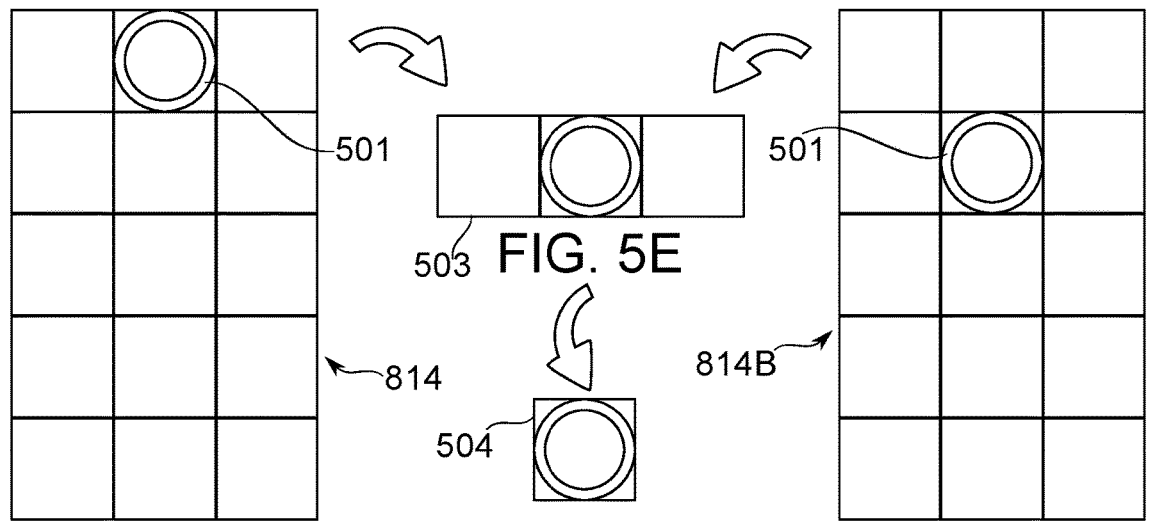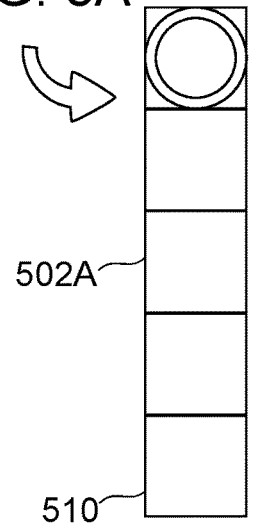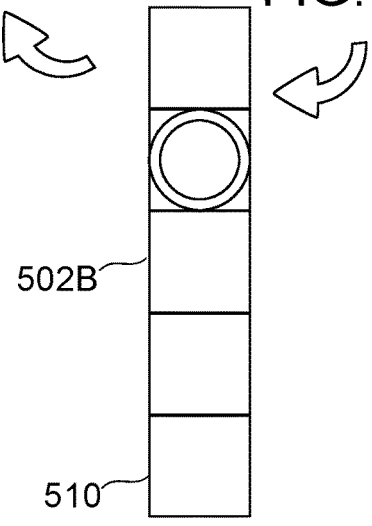

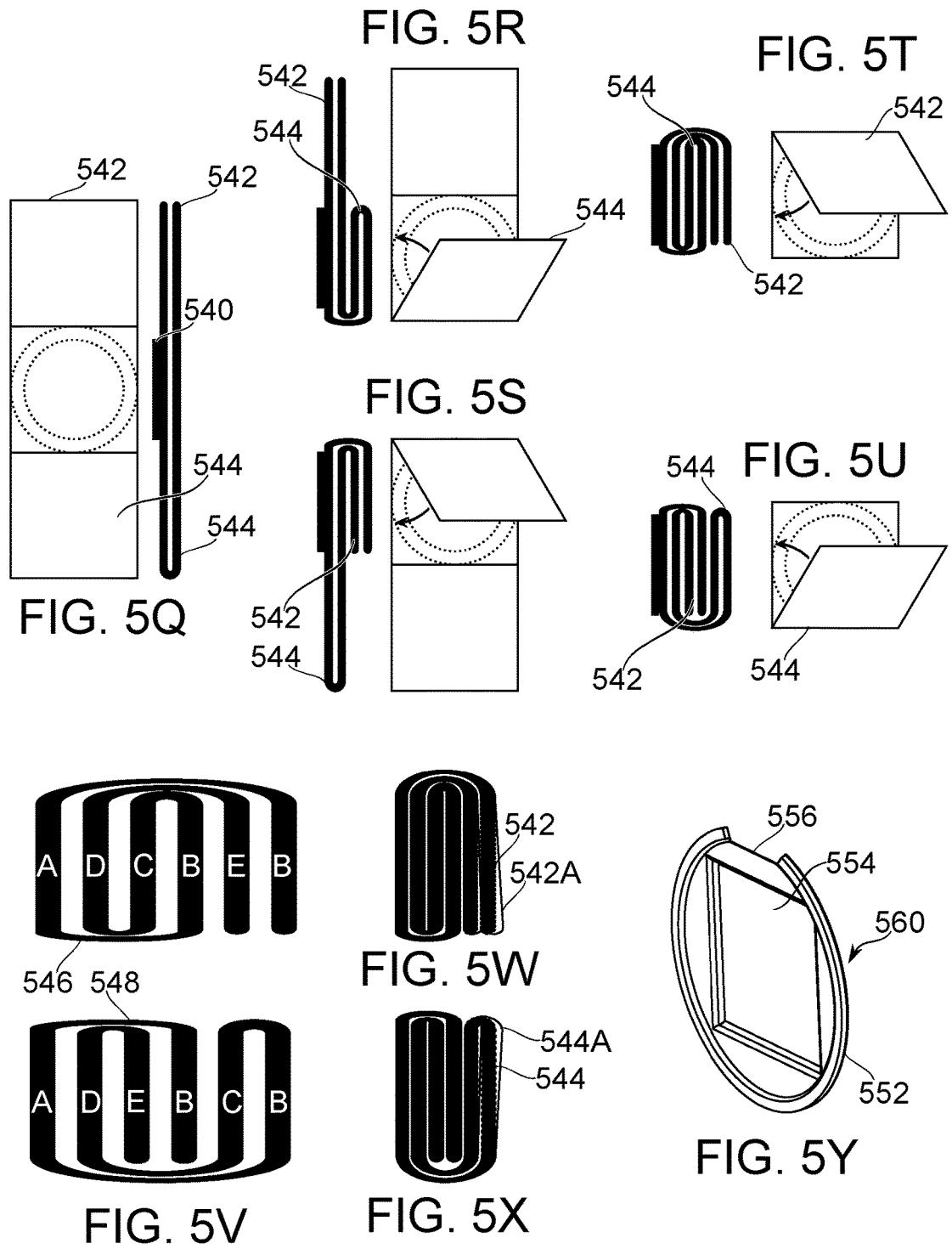

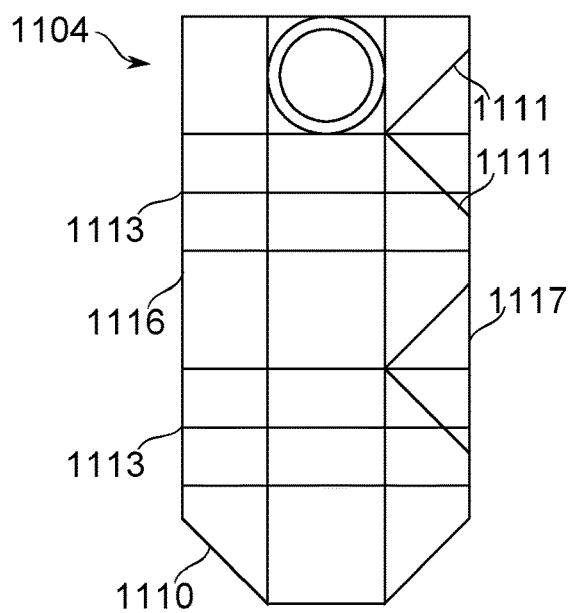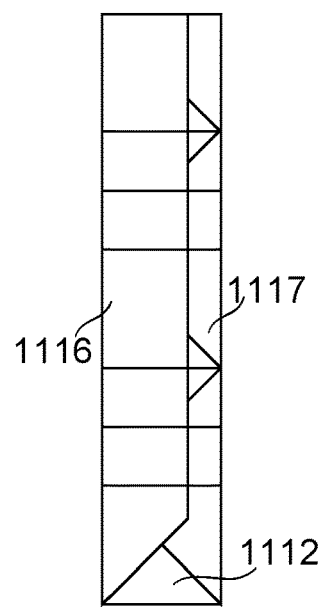
FIG. 6G  FIG. 6H
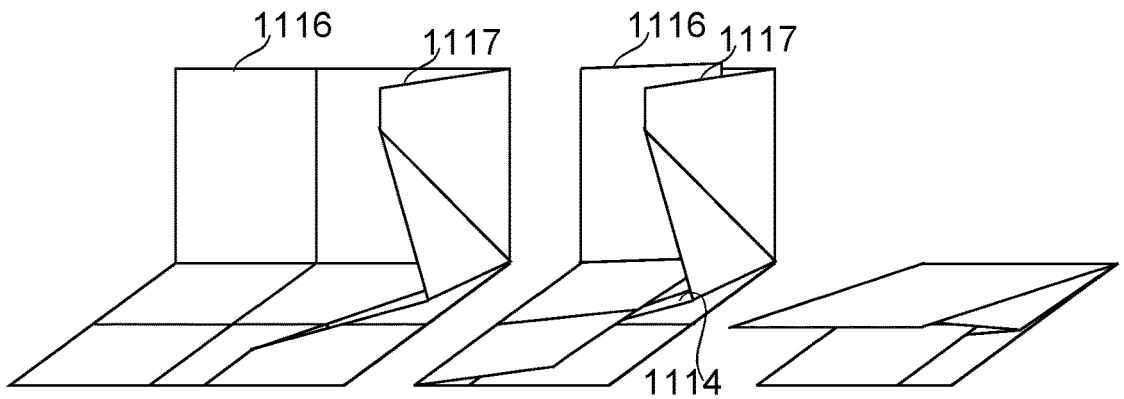
FIG. 6I  FIG. 6J  FIG. 6K
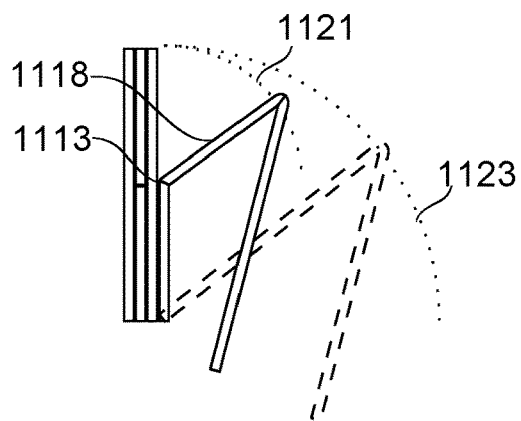
FIG. 6L

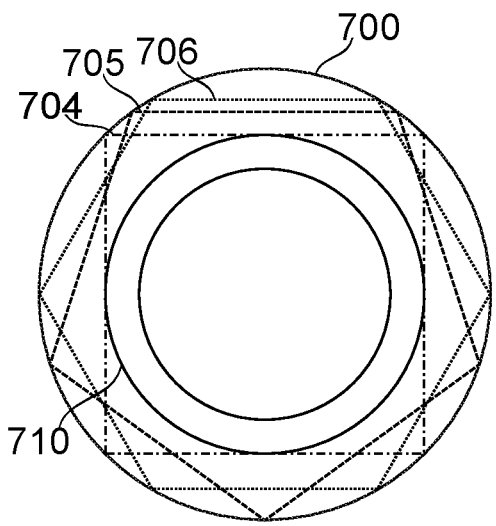
FIG. 7
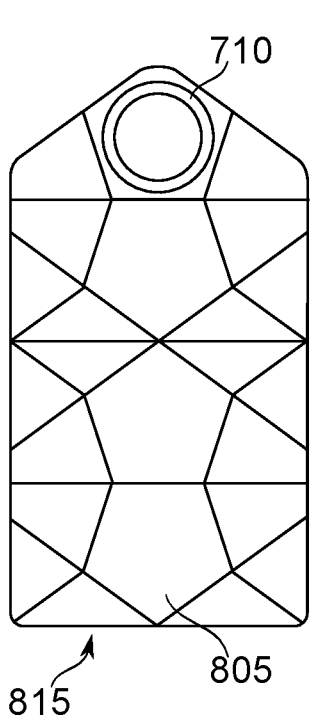 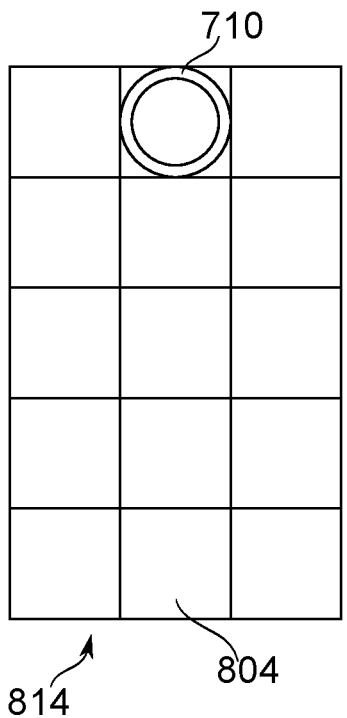 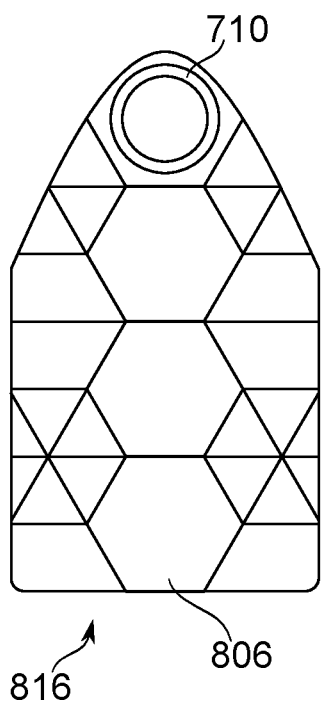
FIG. 8A    FIG. 8B    FIG. 8C

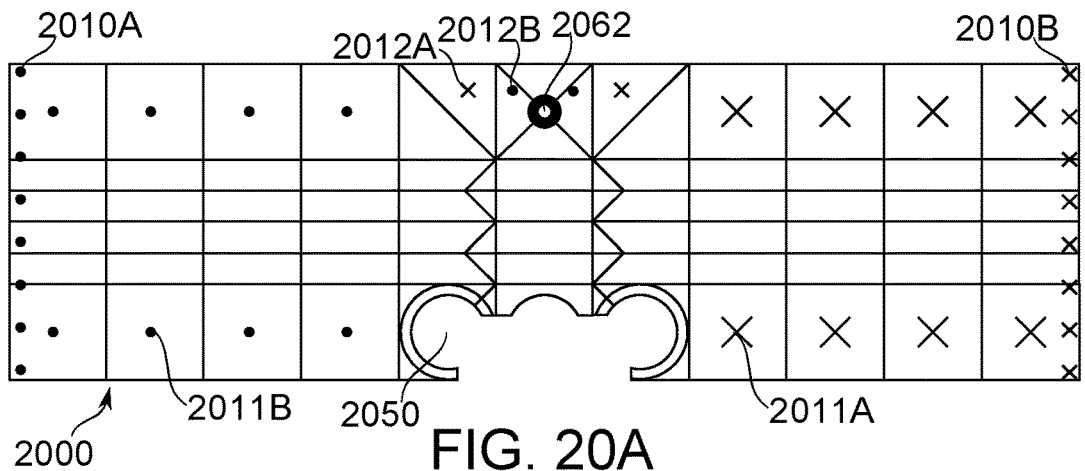
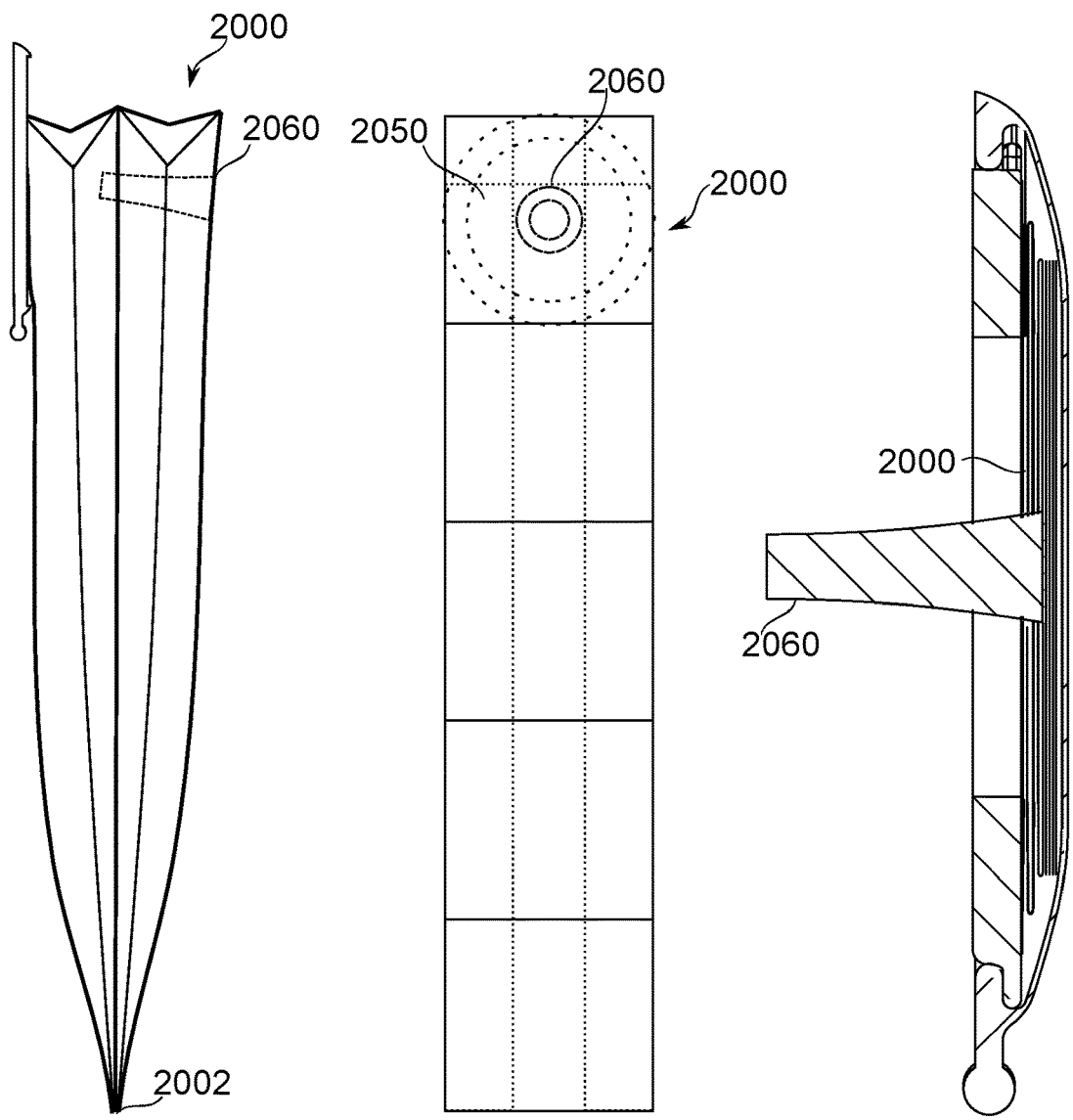
FIG. 20C  FIG. 20B  FIG. 20D

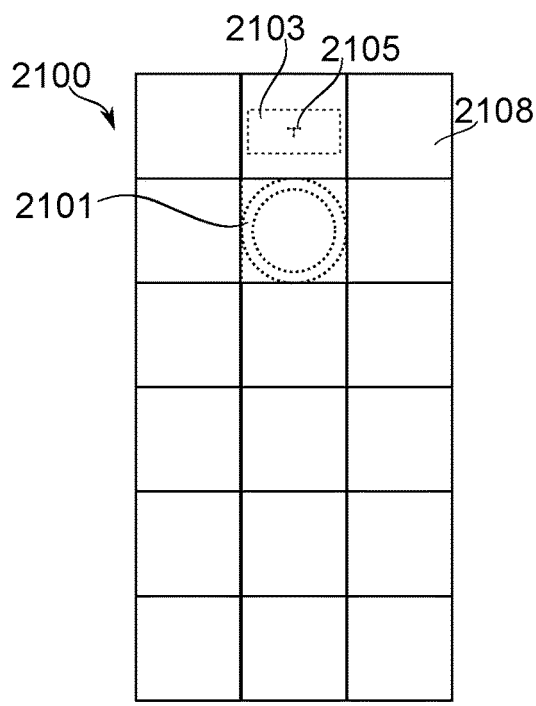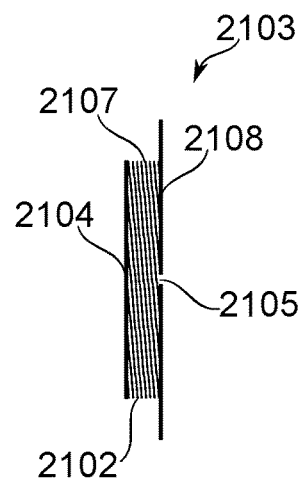
FIG. 21A  FIG. 21B
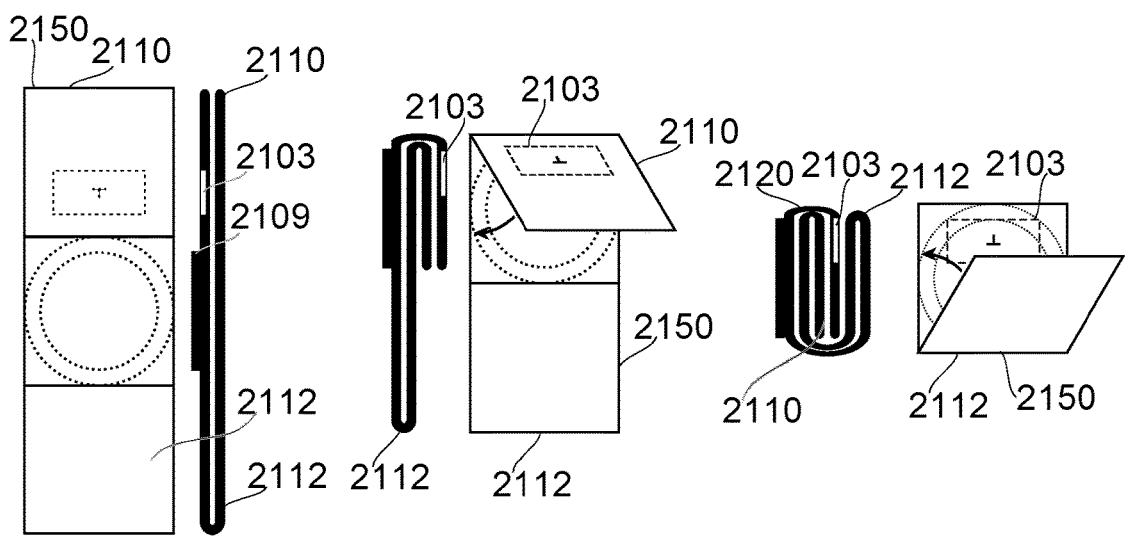
FIG. 21C  FIG. 21D  FIG. 21E

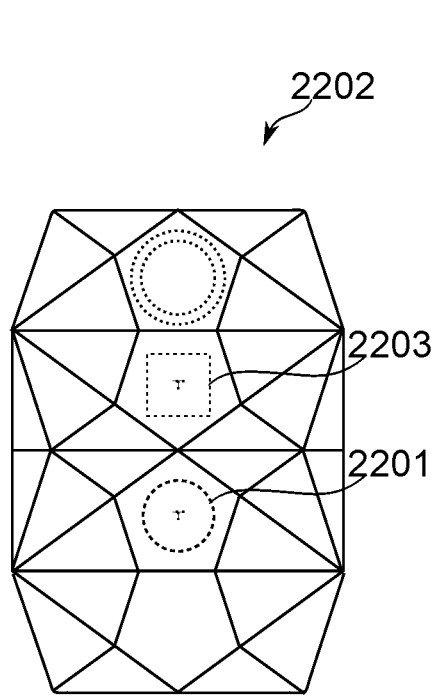
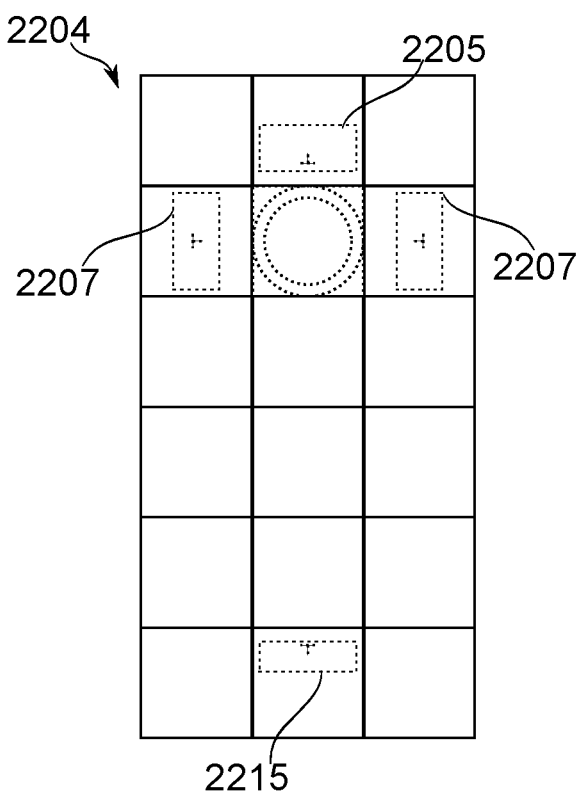
FIG. 22A
FIG. 22B
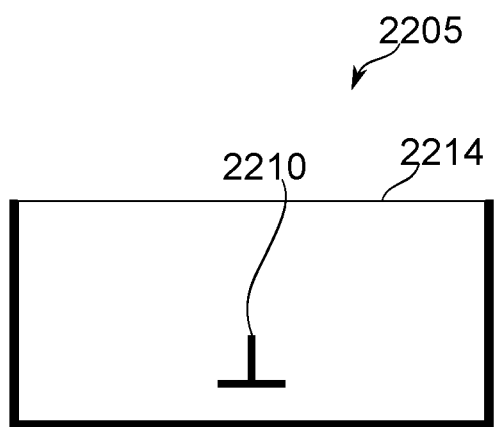
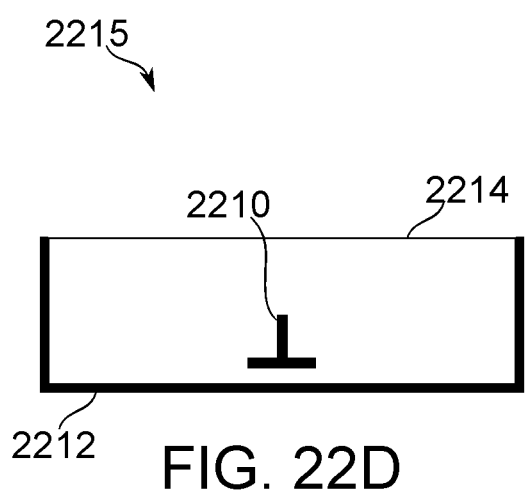
FIG. 22C
FIG. 22D

COMPACT OSTOMY APPLIANCE

FIELD AND BACKGROUND OF THE INVENTION

The present invention, in some embodiments thereof, relates to the field of medical care for surgically created openings (stoma) in living subjects, and more particularly, to devices and methods for covering a stoma as may be used in the case of a colostomy, ileostomy or urostomy.

In ostomy surgeries, an end or a side of a healthy portion of intestine is surgically attached to a stoma formed in the abdominal wall. Attachment may be to the visceral side, or a surgeon may pass the intestinal portion through the stoma and attach it to the outside of the abdominal wall. Large or small intestine is attached, depending on the type of ostomy.

A stoma may be permanently left in a patient when intestinal content can no longer pass out through the anus, due, for example, to colon cancer, diverticulitis, trauma, or inflammatory bowel disease. A stoma may be temporary, for example, following an operation on a section of bowel requiring a healing period.

Use of an ostomy appliance is indicated for patients with a stoma, to help manage stomal discharge. According to the nature of the stoma, stomal discharge comprises, for example, fecal matter, urine, and/or mucus. Appliances may be wholly external, or at least partially internal. Common elements of ostomy appliances include a pouch for collecting stomal discharge, and a means to seal the pouch over the stoma. In some cases, a plug or cover is used in addition to, or in place of a pouch.

Described ostomy appliance designs include the following:

U.S. Pat. No. 8,070,737 relates to "a controlled evacuation ostomy appliance compris[ing] a membrane that is urged into sealing engagement with a stoma, by the generation of radial tension in the membrane. A tensioning device applies tension, with respect to the stoma, at one or more positions that are (i) outboard of the periphery of the projecting portion of the stoma, and/or (ii) between the level of the peristomal skin and the level of the most projecting part of the stoma. Tension limiting means are disclosed. The membrane may be gas-permeable to allow flatus to be vented".

U.S. Pat. No. 8,092,437 relates to "a flexible membrane [ . . . ] situated within a rigid or semi-rigid cap. The edge of the cap wall is adhesively fixed to the tissue surrounding the stoma. The interior of the cap is pressurized to press the membrane to seal the stoma against the discharge of solid and semi-solid waste. Gas escapes through a vent with a filter element. The cap can be pressurized by an external pump or an integral pump member situated on top of the cap. A relief valve prevents over pressurization. A collection pouch can be provided as part of a device. The device can be removably mounted on a standard two-piece faceplate".

U.S. Pat. No. 7,250,040 relates to "an arrangement at a stoma bag of the type used by persons or animals with a colostoma, including a flexible bag (flexibag) and a ring fastener/magazine ring, where the ring fastener/magazine ring is designed to be connected to a stoma plate, and where, in its initial position, the entire flexibag is located in or in close proximity to the ring fastener/magazine ring".

SUMMARY OF THE INVENTION

According to an aspect of some embodiments of the present invention, including, for example, any of the embodiments described herein, there is provided an ostomy appliance to provide continence to a stoma, comprising: a collapsed waste collection pouch for receiving stomal waste, and having a membranous body; the membranous body having an aperture attached to a proximal end of the ostomy appliance and sized to receive waste therefrom; a closure region of the membranous body comprising membrane surface extending substantially parallel and proximal to the aperture; wherein the limits of the closure region are defined by folds; and the folds restrict waste reaching the aperture from moving past the closure region into the remainder of the pouch body, when attached as a collapsed pouch to the ostomy appliance.

According to some embodiments of the invention, including, for example, any of the embodiments described herein, the body of the waste collection pouch comprises a folded configuration having a polygonal cross-section perpendicular to a distal-proximal axis, the area of the cross-section being less than 25% of the enclosed area of the unfolded pouch.

According to some embodiments of the invention, including, for example, any of the embodiments described herein, at least one region of the pouch outside the closure region extends substantially parallel to the aperture and across at least 80% of the closure region.

According to some embodiments of the invention, including, for example, any of the embodiments described herein, a plurality of separate regions of the pouch, each separated from the closure region by at least one of the folds, are folded to overlap one another.

According to some embodiments of the invention, including, for example, any of the embodiments described herein, the pouch comprises at least two plies of a membranous material, secured to one another at the edges to create a sealed receptacle for receiving waste.

According to some embodiments of the invention, including, for example, any of the embodiments described herein, the folded configuration comprises a predetermined number of layered panels of pouch material lying substantially perpendicular to a proximal-distal axis.

According to some embodiments of the invention, including, for example, any of the embodiments described herein, the closure region membrane surface comprises a substantially flat wall proximal to the proximal end.

According to some embodiments of the invention, including, for example, any of the embodiments described herein, the polygonal cross-section is fitted to the shape of a recess in a component of the ostomy appliance.

According to some embodiments of the invention, including, for example, any of the embodiments described herein, the recess is fitted to the depth of the collapsed waste collection pouch, such that the collapsed pouch is held with layers compressed against one another.

According to some embodiments of the invention, including, for example, any of the embodiments described herein, the ostomy appliance comprises a pouch restraint, wherein the pouch restraint comprises the recess.

According to some embodiments of the invention, including, for example, any of the embodiments described herein, the ostomy appliance comprises an ostomy component housing extending distally from the pouch, wherein the ostomy component housing comprises the recess.

According to some embodiments of the invention, including, for example, any of the embodiments described herein, the folds comprise bends in opposite enclosing surfaces of the membranous body, such that the enclosing surfaces are pressed into continuous contact with one another along the extent of the folds.

According to some embodiments of the invention, including, for example, any of the embodiments described herein, the membranous body is held into a compact configuration such that the folds are pressed together, such that there is insufficient volume beyond them for the waste to move into.

According to some embodiments of the invention, including, for example, any of the embodiments described herein, the polygonal cross-section is a quadrilateral.

According to some embodiments of the invention, including, for example, any of the embodiments described herein, the polygonal cross-section is a pentagon.

According to some embodiments of the invention, including, for example, any of the embodiments described herein, the polygonal cross-section is a hexagon.

According to some embodiments of the invention, including, for example, any of the embodiments described herein, the polygon is regular.

According to some embodiments of the invention, including, for example, any of the embodiments described herein, the polygon is convex.

According to some embodiments of the invention, including, for example, any of the embodiments described herein, the polygonal cross-section comprises a shape formed by folds comprising a plurality of substantially parallel crease lines.

According to some embodiments of the invention, including, for example, any of the embodiments described herein, the plurality comprises at least three crease lines.

According to some embodiments of the invention, including, for example, any of the embodiments described herein, the polygonal cross-section comprises a shape formed by folds comprising at least one crease line at a substantially right angle to the substantially parallel crease lines.

According to some embodiments of the invention, including, for example, any of the embodiments described herein, the polygonal cross-section comprises a shape formed by folds comprising at least two crease lines substantially at relative angles characteristic of at least one of the group of right quadrilateral, regular pentagon, and regular hexagon.

According to some embodiments of the invention, including, for example, any of the embodiments described herein, the at least two crease lines comprise intersections in the body of the waste collection pouch.

According to some embodiments of the invention, including, for example, any of the embodiments described herein, the substantially flat wall proximal to the proximal end comprises a smooth region which occupies a predetermined distance from a distal floor of the ostomy appliance.

According to some embodiments of the invention, including, for example, any of the embodiments described herein, the predetermined distance comprises a stomal height, adjusted by a predetermined tolerance spacing.

According to some embodiments of the invention, including, for example, any of the embodiments described herein, the predetermined tolerance is greater than 0 mm, and less than 5 mm.

According to some embodiments of the invention, including, for example, any of the embodiments described herein, the predetermined tolerance is greater than 0 mm, and less than 2 mm.

According to some embodiments of the invention, including, for example, any of the embodiments described herein, the pouch is restrained from deployment by the folded structure of the pouch body interfering with its own opening.

According to some embodiments of the invention, including, for example, any of the embodiments described herein, the interfering comprises a first fold being restrained from opening before a second fold opens.

According to some embodiments of the invention, including, for example, any of the embodiments described herein, the interfering comprises distributing forces acting to deploy the pouch body such that non-zero magnitude opening forces at a fold are insufficient to overcome forces that act to close the fold.

According to some embodiments of the invention, including, for example, any of the embodiments described herein, the collapsed waste collection pouch is folded to present a proximal surface comprising the face of a single folded panel.

According to some embodiments of the invention, including, for example, any of the embodiments described herein, the collapsed waste collection pouch is folded to present a proximal surface comprising a region which is adapted to be manipulated to deploy the pouch for filling with waste.

According to some embodiments of the invention, including, for example, any of the embodiments described herein, pulling on a proximal portion of the folded pouch in a single direction deploys the pouch for filling with waste.

According to some embodiments of the invention, including, for example, any of the embodiments described herein, the folded configuration comprises at least one fold following a crease-line which runs substantially at an angle between parallel to and perpendicular to an axis of the bag which follows the direction along which the bag hangs when deployed.

According to some embodiments of the invention, including, for example, any of the embodiments described herein, the proximal end of the ostomy appliance to which the pouch is attached comprises an ostomy appliance cap.

According to an aspect of some embodiments of the present invention, including, for example, any of the embodiments described herein, there is provided a folded pouch for use with an ostomy appliance to provide continence to a stoma, comprising: a membranous body having an aperture: configured to fit against a proximal end of the ostomy appliance and sized to receive waste therefrom; a frame configured to attach to the ostomy appliance and fit the aperture thereto; a closure region of the membranous body comprising membrane surface extending substantially parallel and proximal to the aperture; wherein folding of the pouch restricts waste reaching the aperture from moving past the closure region into the remainder of the pouch body, when attached as a collapsed pouch to the ostomy appliance.

According to some embodiments of the invention, including, for example, any of the embodiments described herein, the folding comprises folds at an angle deviating from substantially parallel and substantially perpendicular to a direction of force applied when the pouch is manipulated to be deployed for filling with waste.

According to an aspect of some embodiments of the present invention, including, for example, any of the embodiments described herein, there is provided a packaged set of ostomy appliance components for providing continence to a stoma, comprising: at least a predetermined number of collapsed waste collection pouches, each having a body; and at least one pouch restraint; wherein a proximal surface region of the body is disposed to press against the pouch restraint upon receiving pressure from a distal side; the pouch restraint being configured to release the pouch on average at a target level of the pressure; and the standard deviation of the actual release pressure among all pouches provided in the packaged set is no more than 20% of the target level.

According to some embodiments of the invention, including, for example, any of the embodiments described herein, the standard deviation is no more than 10% of the target level.

According to some embodiments of the invention, including, for example, any of the embodiments described herein, the predetermined number of collapsed waste collection pouches is ten or more.

According to some embodiments of the invention, including, for example, any of the embodiments described herein, the pressing occurs entirely over the surface of a single folded panel of the waste collection pouch.

According to an aspect of some embodiments of the present invention, including, for example, any of the embodiments described herein, there is provided a method of deploying a pouch from an ostomy appliance, comprising: setting a pouch restraint to release a pouch for deployment at a predetermined release pressure; and automatically releasing the restraint at an actual intra-abdominal release pressure based on the predetermined release pressure; wherein for an unbiased sampling of at least ten such actual intra-abdominal release pressures, the standard deviation of the unbiased sampling is no more than 20% of the predetermined release pressure.

According to an aspect of some embodiments of the present invention, including, for example, any of the embodiments described herein, there is provided a method of manufacturing a waste collection pouch for use with an ostomy appliance, comprising: receiving a folding pattern for the waste collection pouch comprising crease lines and directions of folding therearound; and folding the pouch according to the folding pattern.

According to some embodiments of the invention, including, for example, any of the embodiments described herein, the folding comprises setting a jig for setting the location of the crease lines on the pouch.

According to some embodiments of the invention, including, for example, any of the embodiments described herein, the method comprises attaching an aperture of the pouch over an aperture of an ostomy appliance.

According to some embodiments of the invention, including, for example, any of the embodiments described herein, the method, comprises attaching a frame member to the pouch.

According to some embodiments of the invention, including, for example, any of the embodiments described herein, the method comprises setting a pouch restraint to prevent deployment of the pouch below a predetermined release pressure.

According to some embodiments of the invention, including, for example, any of the embodiments described herein, the pouch is folded to a substantially flat package shape by the folding.

According to some embodiments of the invention, including, for example, any of the embodiments described herein, the folding pattern comprises at least four parallel creases.

According to some embodiments of the invention, including, for example, any of the embodiments described herein, the direction of bending around the parallel folds changes in alternation.

According to some embodiments of the invention, including, for example, any of the embodiments described herein, the direction of bending around each of the parallel folds is the same.

According to an aspect of some embodiments of the present invention, including, for example, any of the embodiments described herein, there is provided an ostomy cap for sealing a surgical stoma comprising: a folded ostomy pouch; and a pressure-releasing pouch restraint positioned to prevent the pouch from deploying from its collapsed state below a selected threshold of pressure received from within the abdominal cavity; wherein the folding pattern of the collapsed pouch is adjustable to one of a plurality of predetermined folding patterns; and the selected threshold of pressure is changeable, according to the folding pattern.

According to some embodiments of the invention, including, for example, any of the embodiments described herein, the relative orientation of the folded ostomy pouch and the pressure-releasing pouch restraint is selectable from among a plurality of relative orientations, and the selected threshold of pressure is changeable, according to the relative orientation.

According to an aspect of some embodiments of the present invention, including, for example, any of the embodiments described herein, there is provided an ostomy appliance for sealing a surgical stoma comprising: a collapsed pouch; and a pressure-releasing pouch restraint mechanism, including a region of reversible attachment to the ostomy appliance along an extent of an attachment interface, wherein the region of reversible attachment is positioned to receive pressure from the pouch due to pressure exerted from within the abdominal cavity; the region of reversible attachment is configured to progressively detach along the extent over a range of the abdominal cavity pressures, as the abdominal cavity pressure increases.

According to some embodiments of the invention, including, for example, any of the embodiments described herein, the difference in pressure between the lower and upper pressures of the range is at least 10 mmHg.

According to an aspect of some embodiments of the present invention, including, for example, any of the embodiments described herein, there is provided an ostomy cap for sealing a surgical stoma comprising: an ostomy waste collection pouch, collapsed by crimped folding into a package comprising substantially parallel layers of sub-panels, and having a waste inlet into a first sub-panel; and a filter element, sealed across a break in the material of a second sub-panel of the pouch separated from the first sub-panel by a crimped fold, such that it is configured to receive flatus reaching it from the waste inlet pouch, and vent the flatus to the pouch exterior.

According to some embodiments of the invention, including, for example, any of the embodiments described herein, the first and the second sub-panels are separated by a crease located, when the ostomy cap is worn, above the waste inlet, and above the filter element.

According to some embodiments of the invention, including, for example, any of the embodiments described herein, the side of the second sub-panel to which the filter element is attached is overlaid on the outside of the pouch by a substantially parallel surface pressed thereagainst.

According to some embodiments of the invention, including, for example, any of the embodiments described herein, the crimped fold comprises a region which resists the flow of fluid into the second sub-panel.

According to some embodiments of the invention, including, for example, any of the embodiments described herein, the predetermined pressure level is between 1 mmHg and 10 mmHg.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 3A-3D illustrate the appearance of arbitrarily- and pattern-folded pouches with and without a cover-restraint, according to some exemplary embodiments of the invention;

FIGS. 5A-5F illustrate variations on the folding pattern described in reference to FIGS. 4A-4F, according to some exemplary embodiments of the invention;

FIGS. 5Q-5X illustrate the effects of two alternative pouch folding configuration on the function of the folded pouch, according to some exemplary embodiments of the invention;

FIG. 5Y shows a pouch deployment restraint having regions of different attachment strength, according to some exemplary embodiments of the invention;

FIGS. 6G-6L illustrate an exemplary shape and folding pattern of a waste collection pouch according to some exemplary embodiments of the invention;

FIG. 7 illustrates the relative sizes of different regular polygon shapes relative to a circumscribing circle and a central aperture, according to some exemplary embodiments of the invention;

FIGS. 8A-8C show different folding patterns superimposed on pouches of varying shapes, according to some exemplary embodiments of the invention;

FIGS. 20A-20D illustrate a box-pleated ostomy pouch, according to some exemplary embodiments of the invention;

FIG. 21A schematically shows a filter element positioned to vent through the material of an ostomy pouch, according to some exemplary embodiments of the invention;

FIG. 21B schematically shows structural detail of a filter element, according to some exemplary embodiments of the invention;

FIGS. 21C-21E schematically illustrate positioning of a filter relative to folded structure of an ostomy pouch, according to some exemplary embodiments of the invention;

FIGS. 22A-22B show different configurations of filters attached to pouch embodiments, according to some exemplary embodiments of the invention; and FIGS. 22C-22D show filter elements having at least one side protected from waste contamination by a sealing element, according to some exemplary embodiments of the invention.

DESCRIPTION OF SPECIFIC EMBODIMENTS OF THE INVENTION

Figure 1A:
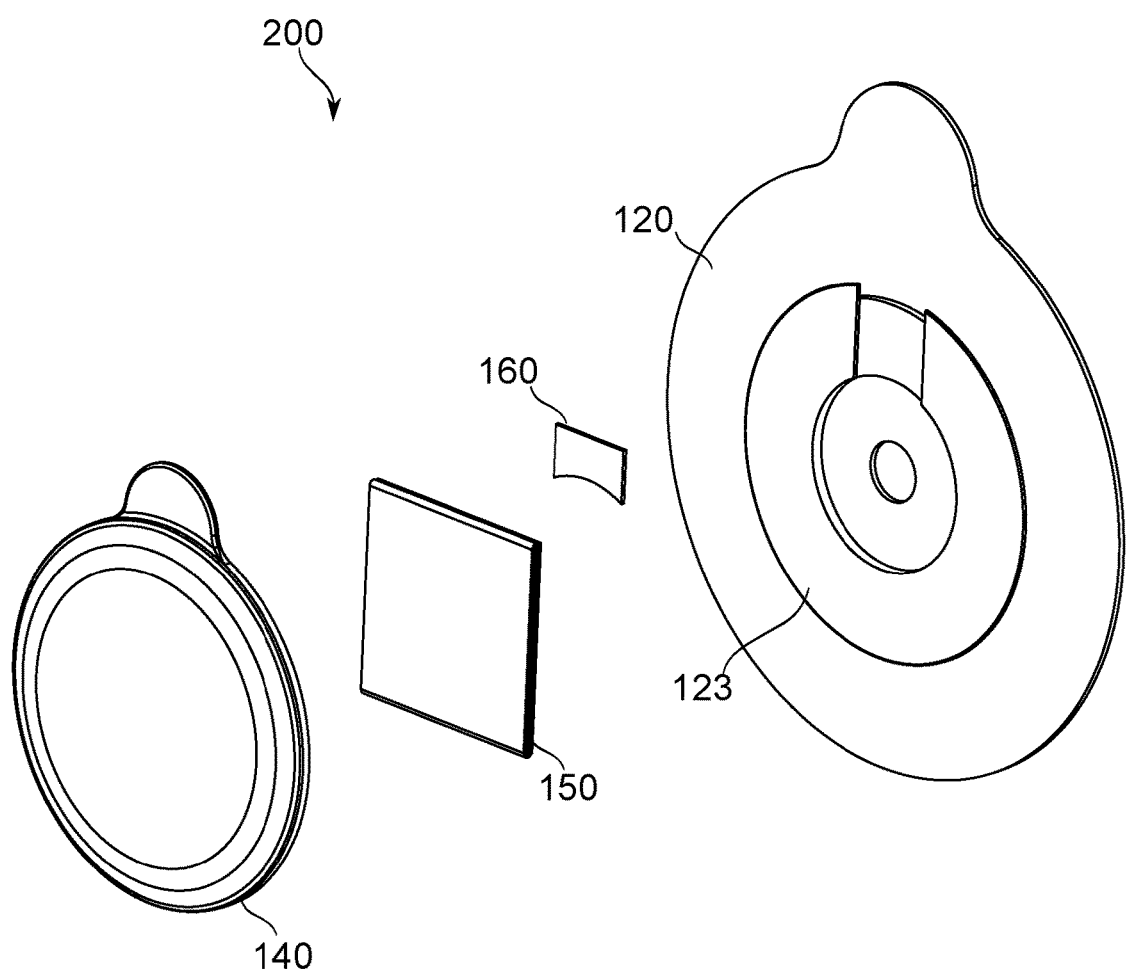
FIGS. 1A-1B schematically illustrate a flat, panel-folded ostomy waste collection pouch held in front of the waste containment compartment of an ostomy appliance, according to some exemplary embodiments of the invention.

The present invention, in some embodiments thereof, relates to the field of medical care for surgically created openings (stoma) in living subjects, and more particularly, to devices and methods for covering a stoma as may be used in the case of a colostomy, ileostomy or urostomy.

Overview

An aspect of some embodiments of the invention relates to panel folding to form a collapsed, restrained ostomy waste collection pouch that resides outside of a stomal compartment defined by an ostomy appliance, with which it is in fluid communication.

In some embodiments of the invention, a pouch for collecting waste from a surgical stoma is folded into a predefined package. In some embodiments, the package comprises a flat package (having a width and breadth larger than a depth in the direction of the stomal axis by a large factor, for example, 5× or greater, 10× or greater, 20× or greater, or another larger smaller or intermediate factor). In some embodiments, the package is folded into corrugations such that the depth in the direction of the stomal axis is nearer to and/or exceeding at least one of the package width and breadth, for example, having a ratio of width or breadth to depth which is less than 3, 2, 1, or another larger, smaller, or intermediate factor.

In some embodiments, the predefined package is situated in front of a proximal aperture of a waste containment compartment of an ostomy appliance. The pouch, in some embodiments, is worn initially restrained from deploying to fill with waste. In some embodiments, the waste collection pouch is folded around at least a first crease-line, and rolled up as part of completing the final package shape. In some embodiments, the waste collection pouch is folded around at least a first crease-line, and collapsed arbitrarily as a part of completing the final package shape. A characteristic, in some embodiments, of a predefined package is being sized for fitting containment by a receiving element, or otherwise to be constrained to occupy a predefined volume. Another characteristic, in some embodiments, of a predefined package is a controlled deployment and/or wear behavior; for example: a predicted pressure exerted on one side of the pouch upon another pressure being exerted on another side; a predicted opening pattern defined by the opening of folds upon deployment, or another feature related to the organized structure of the package.

In some embodiments of the invention, the pouch being folded comprises having a plurality of substantially parallel panels (regions delimited by pouch boundaries and/or fold boundaries) in the package, the number of panels being, for example, 4, 9, 12, 16, 18, 20, 40, or another larger, smaller, or intermediate number of panels. In some embodiments of the invention, the pouch being folded comprises having a plurality of crease regions, through which the orientation of the pouch material bends by about 180°, the number of creases being, for example, 1, 2, 3, 4, 5, 6, or a larger predefined number of folds. In some embodiments of the invention, one or more crease regions comprise a change in the orientation of the pouch material through about 90°, for example, comprising a box-like configuration, an accordion-like configuration wherein a first set of panels lies perpendicular to another set of panels, or another configuration.

In some embodiments, the predefined package is compact, for example, comprising less than 75%, 50%, 25%, or less than a larger, smaller, or intermediate amount of empty space compared to the volume of packaged pouch material. In some embodiments, compactness comprises being under compression relative to a folded but loosely held state, for example, compacted to 95% or less of the loose volume, 80% or less of the loose volume, or having another larger, smaller or intermediate compaction ratio. A pouch package is "compact", in some embodiments, if it lies within a thickness which is not more than 50% greater than the ply thickness alone required, or not more than 25%, 75%, or another greater, lesser, or intermediate package thickness. In an exemplary embodiment, two plies of 60 micron pouch film are used to make a pouch, and the pouch itself is folded in a 3×6 pattern of square panels. The overall thickness of the plies alone is thus about 2160 microns (2.16 mm); 150% of this thickness is about 3.24 mm. Considering compactness from another perspective, an exemplary package is 2 mm thick, fully compressed, but if released again, it springs to twice this thickness (due, for example, to inherent "springiness" of the material, bulking issues around folds, or another reason). In some embodiments, a compression ratio of 75% is reached when the package is reduced to a thickness of 3 mm.

In some embodiments, the relative largest single side surface area of the packaged pouch is less than the open (unfolded or unfurled) single side surface area of the pouch, having a relative surface are of, for example, <5%, <10%, <25%, <50%, <75%, <100%, and/or fraction of the unfolded surface area of the pouch which is intermediate, smaller, or larger.

It is to be understood that as used herein, "proximal" refers to the direction away from the body of an ostomate as an ostomy appliance or component thereof is normally worn. "Distal" refers to the direction toward an ostomate body. Thus, in some embodiments of the invention, an ostomy wafer, for example, occupies a more distal region of an ostomy appliance than a pouch cover, which occupies a proximal region of an appliance.

In some embodiments, the flat pouch package comprises a predetermined number of layered panels of pouch material lying substantially perpendicular to an axis projecting outward from the body through the stomal center. In some embodiments, the layered panels are formed by a sequence of crimped folds which create a square, rectangular, or other package outline.

A deployed pouch's function as a flexible, body-mounted waste container is potentially well-fulfilled by having a low profile, a large volume, and/or a shape that inherently hangs below the stoma to receive dropping waste. In some embodiments, the pre-deployed pouch is positioned outside the stomal compartment of an ostomy appliance, potentially avoiding space and/or shape constraints which an internal position could impose. A panel-folded shape is potentially well-suited to compartment-external storage, and/or with respect to other embodiment aspects described hereinbelow. In some embodiments of the invention, panel-folded means that at least one full fold is made in the course of packaging the pouch.

In some embodiments, some crease-lines along which folds are made run substantially parallel and/or substantially perpendicular to an axis of the bag running along the direction in which the bag hangs when fully deployed. In some embodiments, some crease-lines cross said axis at an angle substantially other than 0° or 90°, for example 30°, 45°, 60°, 72°, or another larger, smaller, or intermediate angle. A potential advantage of folds angled across the principle hanging axis of the pouch is that opening force acting downward may be transmitted transversely to open up panels to the sides.

In some embodiments of the invention, folds of the pouch create bounds between sub-chambers (potentially, collapsed sub-chambers) of the pouch such that the flow of waste among sub-chambers across said bounds is restricted. In some embodiments, the flow is restricted to by a resistance to flow which is 10× greater, 100× greater, 1000× greater, 10000× greater, or another intermediate, larger, or smaller relative resistance than flow into an intake aperture of said pouch. In some embodiments, the passage of waste is restricted to a volume which is not more than 0.1% of the maximum capacity of the fully deployed (unfolded) pouch. In some embodiments, the restriction of volume entering the pouch is to a fraction of the fully deployed pouch volume not more than 0.2%, 0.5%, 1%, 2%, 5%, or another greater, lesser, or intermediate fractional volume. In some embodiments, folds of the pouch create a barrier that substantially prevents the flow of solid or liquid waste while enabling the flow of gaseous waste. In some embodiments, a pouch restraint maintains the folded configuration such that the folded configuration can restrict the flow of waste. In some embodiments, the pouch restraint maintains the folded pouch in a substantially minimal and/or a compressed volume and prevents it from expanding. In some embodiments, said preventing the folded bag from expanding is realized while not preventing distortion of the panels, for example in response to elevation of pressure exerted on the folded pouch from within the abdominal cavity.

A potential advantage of a collapsed waste collection pouch panel-folded into multiple layers is an increase in the resistance to the diffusion of odor beyond the pouch. In some embodiments, odor molecules diffusing beyond a first ply of a waste pouch are potentially trapped within a confined space between plies. Diffusion from this space is either to a relatively small crack leading to the outside, or across a much larger surface area leading back into the pouch. Thus, a folded configuration presents a more substantial barrier to odor diffusion than an open configuration, in some embodiments of the invention. A pouch design, in some embodiments, is adjusted to take advantage of this property. For example, pouch engineering constraints representing a requirement for odor impermeability are reduced, allowing the choice of materials which are cheaper, stronger, and/or advantageous in some other parameter. In more particular examples: a thinner ply of pouch material is used, a pouch material which is mechanically strong but relatively permeable to odor is used, a secondary backing which is specifically odor resistant but mechanically weak and/or redundant is omitted, or another relative advantage in cost and/or material properties is obtained. In some embodiments, for example, a polyamide (PA) film is used, rather than a PVC or PVDC film (as is generally used in the art). This is despite PA having somewhat inferior barrier properties. PA is, however, potentially easier to manufacture into a pouch form. PA provides a potential environmental benefit in that it does not contain chlorides. In some embodiments of the invention, this benefit comes without requiring an increase in film thickness, and/or with a decrease in film thickness. For example, a typical PVC- or PVDC-based ostomy films has a thickness of 60-100 microns. The inventors have found success with using PA-based films of thickness 60 microns.

An aspect of some embodiments of the invention relates to control of a pouch release pressure by use of a panel-folded waste collection pouch for transmitting pressure to a releasable restraint mechanism.

In some embodiments, a flat pouch package is covered and/or held in place by a pouch restraint comprising, for example, a lid, a latch, and/or a strap. In some embodiments, the pouch restraint comprises a mechanism for releasing the restraint under a sufficient predetermined pressure exerted from within the abdominal cavity. Optionally, the predetermined pressure is a safety limit. Additionally or alternatively, the predetermined pressure is variable according to the preferences of a user. For example, a user intending a period of high exertion sets a relatively high threshold of deployment, potentially preventing deployment as a result of transiently generated internal pressures. In another example, a user intending to sleep sets a relatively low threshold of deployment, so that safe deployment occurs even though the device itself is unattended.

Potentially, a collapsed pouch transmits pressure irregularly and/or unpredictably to a pouch restraint mechanism, increasing the width of the range of actual deployment pressures. A pouch collapsed by panel folding potentially transmits pressure more dependably to a pressure-releasable restraint mechanism than some other configurations.

It is a potential advantage for the expected range of pressure sufficient to cause restraint removal to be relatively narrow. For a narrower range of predictable release pressure, a higher lowest release pressure is settable in some embodiments, without impairing consistency of release before exceeding a safe pressure limit. A higher self-deployment pressure provides the potential advantage of allowing an ostomate a longer and/or more predictable period of waste continence.

Notwithstanding that above, it is also a potential advantage for deployment to approach gradually in some situations. For example, a deployment prevention element is optionally configured, in some embodiments, to "peel" away from a restraining position over a range of pressures, and/or over an extended period. Potentially, the period is sufficiently extended to allow an ostomate to notice a change, and to take action to reverse the conditions leading to deployment. For example, the ostomate vents gas manually (in some embodiments, a valve is provided which allows this). Peeling, in some embodiments, comprises a protrusion (optionally, an irregular and/or abruptly-edged protrusion) from the pre-deployment configuration of the ostomy device. In some embodiments, the protrusion is, for example, up to 3 mm, 5 mm, 10 mm, or another larger, smaller, or intermediate distance from the pre-deployment configuration of the ostomy device.

Potentially, a partially-detached deployment prevention element, such as a cover, can be pressed back into place. Optionally—and to potential advantage particularly if venting is inappropriate and/or insufficient to reduce pressure— an ostomate that notices peeling holds the deployment prevention element in place by hand, allowing deployment to be postponed until it is possible to retire to an appropriate place for deployment and/or waste disposal. Potentially, the period is sufficiently extended to prevent full deployment as a result of a sudden and transient pressure elevation, as can occur for example upon sneezing or bending over. Peeling is noticed by an ostomate, for example, by the sensation of an irregularity interfering with the lie of clothing, and/or by directly reaching to touch the appliance (potentially through clothing, for example, to make an unobtrusive check after a sneeze). In some embodiments, the onset of peeling is noticed by a tactile and/or audible "click" experienced by the ostomate upon testing the cover by pressing on it. In some embodiments, peeling comprises peeling of the bag away from an adhesive restraint (for example, placed on a portion of the bag in contact with another ostomy component, and/or on two separate portions of the bag in contact with one another). In some embodiments, peeling from the adhesive is reversible, such that, for example, the pouch can be replaced on the adhesive region by pressing it back into place.

In some embodiments, sudden deployment is selectable. This is optionally preferred, for example, for sleeping, when the sudden opening of the pouch potentially provides a ready alarm indicating that waste should be urgently disposed of.

In some embodiments of the invention, alternative folding patterns yield predictable corresponding alternative deployment thresholds, deployment pressure ranges, and/or deployment behaviors. In some embodiments, folding in one pattern produces a relative lower deployment pressure range than folding in an alternative pattern. In some embodiments, a folding pattern results in gradual release of a deployment prevention device over a period of seconds or longer, and/or over a range of increasing pressures. In some embodiments, the range of pressures over which deployment occurs is 1-2 mmHg, 1.5-4 mmHg, 2-5 mmHg, 5-10 mmHg, or another range having the same, intermediate, larger and/or smaller bounds. Alternatively or additionally, another folding pattern results in automatic deployment which is substantially immediate upon the initiation of detachment of a deployment prevention device due to pressure transmitted from within the abdomen. In some embodiments, the deployment pressure is, for example, 50-80 mmHg, 70-100 mmHg, 80-120 mmHg, 100-150 mmHg, 140-200 mmHg, or another range of pressures having the same, intermediate, larger and/or smaller bounds. In some embodiments, the difference in lowest, highest, and/or average automatic deployment pressures between a first and a second folding pattern is, for example, 1-2 mmHg, 2-8 mmHg, 5-15 mmHg, 10-20 mmHg, or another range of pressures having the same, intermediate, larger or smaller bounds.

In some embodiments of the invention, alternative folding patterns comprise alternation of an overlaying and of an overlaid flap of a folded pouch. In some embodiments, for example, there is an upper pouch section folded down over the stomal device, and a lower pouch section folded up over the stomal device. A first alternative folding pattern then comprises, in some embodiments, folding the upper section first and then the lower section to overlay it. A second folding pattern optionally comprises folding the lower section first, and then the upper section to overlay it. In some embodiments of the invention, differences in deployment behavior between alternative folding patterns comprise different lower and/or upper ranges of deployment pressure, different range-widths of full deployment pressure, and/or different range-widths of pressure over which deployment proceeds from partial to full detachment of a deployment prevention device. In some embodiments, a free end of a folded flap (an end which is front-most, and/or not overlaid by another flap) comprises an initiation point from which deployment occurs.

In some embodiments, positioning of the free end relative to another part of the ostomy appliance (such as a deployment prevention element) changes the degree of leverage applied by the free end upon the application of pressure, relative to the distribution of attachment strengths preventing deployment. In some embodiments, the choice of free end position comprises a change in the order of folds made—and in particular, which fold is made last. In some embodiments, the relative positions of pouch segments (panels) relative to the number and/or sharpness of bends separating them from an intake aperture of the pouch determines the relative degree of pre-deployment inflation they receive from a given received pressure. In some embodiments, a free end panel which inflates more easily results in a greater concentration of pressure at a contact point than a free end panel which expands relatively little, and so transmits more nearly according to the "average" inflation distribution of the panels underlying it. In some embodiments, order of folding affects which fold creases are sharpest, potentially influencing relative propensities to inflate.

An aspect of some embodiments of the invention relates to structure of a deployment prevention element which comprises regions of relatively greater and lesser resistance to detachment.

In some embodiments, an attachment mechanism (for example, a snap-fit mechanism) for connecting a deployment prevention device to an ostomy appliance comprises differences in the sensitivity to detachment at different regions of the mechanism. In some embodiments, for example, a deployment prevention device comprises a cover attached around a perimeter of the housing of a stomal wafer, a stomal cap, or of another body to which it is mounted. Optionally, attachment around the housing perimeter comprises a region where attachment is broken. Optionally, attachment around the housing perimeter comprises a region where attachment is relatively weaker, for example because of a shorter flange and/or recess used in the attachment mechanism, a difference in an angle (measured with respect to the proximal-distal direction) of a face in a flange and/or recess used in the attachment mechanism, a difference in the thickness of constructing material, and/or a difference in material composition (reflected, for example, in varying rigidity). In some embodiments, an attachment region is made relatively stronger or weaker by an applied substance, for example, an adhesive (for strengthening), or a lubricant (for weakening). In some embodiments of the invention, a difference in detachment pressure at different points on the deployment prevention element allows partial and/or gradual detachment, for example, as a function of time and/or as a function of increasing pressure. In some embodiments, a relatively weak attachment area detaches first, with gradual detachment occurring with increasing pressure from within the abdominal cavity. In some embodiments, a relatively strong attachment area is positioned to detach first, for example, by arranging pressure conveyed to the deployment element such that it is highest in the region of strong attachment. Potentially, the cover detaches quickly after the strongest attachment is broken; for example, since a threshold for detachment of the other regions is already surpassed, and/or since pressure is conveyed differently to other regions of the deployment prevention element once the strongest region of attachment is broken. In some embodiments, the pressure is applied through an ostomy pouch.

An aspect of some embodiments of the invention relates to the interaction of an ostomy pouch and an ostomy pouch restraint to produce a plurality of deployment behaviors in an ostomy appliance assembly.

In some embodiments, alternative relative positions of an ostomy pouch and an ostomy pouch restraint produce different deployment behaviors. Deployment behaviors which alter include, for example: a threshold of deployment pressure, a threshold at which detachment begins, a width of a range of pressure within which full deployment occurs, and/or a width of a range of pressures through which detachment gradually occurs.

Configuration of deployment behavior is, for example, by bringing a relatively more weakly or more strongly attached region of a deployment prevention element into proximity with a first- and/or most-expanding region of the ostomy pouch (such as, for example, a free end of a fold flap, or a region to which gas has relatively free access under pressure). Optionally, configuration is by choosing a rotational orientation of the deployment prevention element when it is installed. In some embodiments, arrangement of the pouch is used to configure how a pouch interacts with a deployment prevention element having two or more regions configured to receive and respond differently to pouch pressure. It is to be understood that bringing pressure to bear first against a region of the deployment prevention element more resistant to detachment does not necessarily result in a higher threshold for automatic deployment.

An aspect of some embodiments of the invention relates to the configuration of a filtering element with an ostomy pouch, such that the filter is operable to release gas while the ostomy pouch is collapsed.

In some embodiments of the invention, a filter is placed in a defined region of an ostomy pouch. Optionally, the region is chosen such that it functions when the ostomy pouch is collapsed, for example, folded, more particularly, folded in creased panels, or still more particularly, folded in creased panels comprising a plurality of panels of substantially equivalent in size to the largest panel (for example 80%, 90%, or another fraction of the largest panel size).

In some embodiments of the invention, one or more creases between panels functions to restrict the passage of liquid and/or solid waste. In some embodiments, the passage is restricted by crimping of a fold across a crease. In some embodiments, resistance to passage through a fold is maintained by restriction of expansion space by a pouch restraint.

It is a potential advantage to restrict the access of solid and/or liquid waste to a filter, to reduce the occurrence and/or rate of filter blockage. In some embodiments, the filter is overlaid by a membrane that is permeable to gases but impermeable to liquids and solids, potentially reducing production complexity and cost. In some embodiments, flatus passes the one or more creases to reach the filter. In some embodiments of the invention, the filter is placed within a designated panel of the folded ostomy pouch. In some embodiments, the designated panel is located in a panel separated by one crease from an intake aperture of the ostomy bag. In some embodiments, the designated panel is above the intake aperture in the deployed bag. In some embodiments, the designated panel is folded over the region of the intake aperture, such that waste, in order to reach the filter, must flow upward for at least a portion of its journey, for example, upward to reach a crease, then downward; and/or downward, to reach a crease, and then upward.

In some embodiments, relative resistance to liquid as opposed to gaseous flow across a crease comprises straining based on the relative viscosities and/or surface tensions of the two material types. In some embodiments, the influence gravity reduces liquid flow through a fold region while gaseous flow is relatively unaffected. In some embodiments of the invention, a greater mobility of gas under pressure allows it to reach and fill voids before liquid. Potentially, this reduces the pressure differential driving the movement of material. In some embodiments, a crease region comprises a narrow channel which resists the flow of liquid along its length more than the flow of gas, for example, due to surface properties of the pouch (such as hydrophobicity) interacting differently with the liquid and the gas.

In some embodiments, the designated panel is chosen to achieve a desired pathway of access of flatus to the filter element from within the folded pouch, for example, across one crease, two creases, three creases, or more. Optionally, the choice of path length is based on a desired relative amount of resistance to flatus passage and/or solid/liquid waste passage. In some embodiments, the designated panel is chosen based on the position of a venting aperture of the filter within the folded stomal waste pouch package. For example, the venting aperture is placed to be positioned on the outermost surface of the package, with access to the exterior after passing directly to an open side of a fold, and/or with access to the exterior after passing around one or more fold regions of the pouch package. It is a potential advantage to arrange the filter so that its exit aperture remains unblocked during wear, even if the pouch becomes partially inflated. In some embodiments, a compartment containing the ostomy waste collection pouch comprises one or more vents to the outer atmosphere, preventing occlusion of the filter by a buildup of back-pressure. For example, a pouch restraint element (such as a cover for an ostomy cap) comprises one or more apertures, and/or one or more regions where attachment to the ostomy appliance is incomplete, and/or permits the passage of gas. In some embodiments, the pathway of access of flatus to the filter element is set such that gas flow through the filter is low, for example no more than 1-10 ml/min, 2-5 ml/min, 3-8 ml/min, or another range of flow rates having the same, intermediate, larger and/or smaller bounds. A low degassing rate provides a potential advantage by enabling more effective filtering. More effective filtering potentially reduces fecal odors and/or enables using less filter material to achieve a given filtering requirement.

In some embodiments of the invention, a filter is placed at a designated position and/or orientation within a panel, for example, at a region of the panel which occupies a higher position when the pouch is in its folded configuration. Positioning at a high point provides a potential advantage for reducing the opportunity for contact with solid and/or liquid waste. In some embodiments of the invention, the filter is placed sufficiently far from creases that it substantially does not interfere with folding: for example, at least 5-10 mm away. In some embodiments the filter is sized to avoid creases; for example, it is at least 5-10 mm away from all sides of the folded panel near a crease. This is a potential advantage for preventing pinching of the filter such that its exit aperture is sealed, preventing the exit of gas from the stoma through it. In some embodiments of the invention, the filter is sealed on sides most liable to come into contact with waste, for example, on the side facing the direction from which waste reaches the filter, and/or on sides adjoining that face. This is a potential advantage for avoiding contamination of the filter with waste. Another potential advantage of side-sealing is to allow an exit aperture of the filter to be nearer to one (sealed) edge of the filter, without shortening the minimum path from the filter inlet surface to the filter outlet. Potentially, this allows a longer path, increasing filtering efficacy. Additionally or alternatively, this potentially allows less filter material to be used. Use of less filter material potentially reduces a materials cost, and/or reduces the bulk of the folded pouch package.

In some embodiments of the invention, the overall configuration of the filter, pouch, pouch restraint, and/or other ostomy appliance components is designed to control the rate of filter flow, and/or the pressure at which flow through the filter initiates (effective crack pressure). In some embodiments, the minimum outflow pressure is set to, for example, 1-10 mmHg. In some embodiments, the minimum outflow pressure is, for example, 1-5 mmHg, 3-7 mmHg, 5-10 mmHg, 8-15 mmHg, 12-20 mmHg, 10-50 mmHg, 45-120 mmHg, or another range of pressures having the same, intermediate, higher, and/or lower bounds. A low effective crack pressure and/or high rate of flow is a potential advantage, for example, to reduce physiological bloating, and/or improve the durability of the sealing of the ostomy containment system (for example, sealing of a wafer against skin). A higher effective crack pressure and/or low rate of flow confers a potential advantage by allowing gas to partially pressurize pouch panel segments past the inlet panel, from where it resists pressurized filling with liquids or solids. Potentially, an effective filter life span is thereby increased. In some embodiments, a lower rate of flow allows use of a (potentially less expensive) filter which is less efficient at odor collection, while still providing sufficiently effective odor control. In some embodiments of the invention, the rate of flow through the filter is restricted by a component other than the filter itself, for example, a crimped fold of the pouch, a size and/or a shape of an outlet (exhaust) aperture of the filter, and/or a degree of compression (for example, by the pouch restraint) of the collapsed pouch.

Effective crack pressure and/or flow rate is regulated, in some embodiments, by (for example) the pattern of folding of a pouch, constraining containment placed on the pouch by a pouch restraint, and/or the design and/or positioning of the filter element itself.

An aspect of some embodiments of the invention relates to enclosure of a surgical stoma within a close-fitting volume defined in part by a region of a panel-folded waste collection pouch that is part of enclosing ostomy appliance.

In some embodiments, the pouch is folded and placed with its main body residing proximal to the flat region it exposes to an enclosed stoma. In some embodiments, the most interior region of the collapsed pouch is held at a position defined by a more rigid structure which defines an inner boundary of a pouch holding area proximal to the stoma. The more rigid structure is, for example, an end region of a rigid or semi-rigid ostomy appliance housing.

In some embodiments, the folded pouch is positionable near the stomal aperture without irregularities that could protrude to press and/or chafe stomal tissue. In some embodiments, the pouch is positioned close to the stoma, without exerting more than transitory and/or negligible pressure on it. Close positioning potentially restricts the volume of waste which can enter the stomal enclosure, which may result in lowered irritation of enclosed tissue. In some embodiments, the internally exposed pouch region is covered with a gel, for example, a petroleum jelly, which potentially contacts tissue of the aperture. Optionally, the contact comprises a barrier that resists the passage of waste to tissue beyond the stomal aperture. It is a potential advantage for the waste collection pouch to present a flat interior surface, such that a layer of gel can be spread that forms a consistent barrier around the stomal aperture.

It is a potential advantage for the close fitting of other stomal compartment elements (such as sealing elements and/or housing walls) if the collapsed pouch is held largely outside of the volume that directly encloses the stoma, so as not to interfere with their placement and/or sealing.

An aspect of some embodiments of the invention relates to the appearance and/or performance characteristics of a panel-folded bag incorporated into an ostomy appliance.

In some embodiments, the outer (most proximal) panel-folded bag surface is smooth. In some embodiments, a cover for the surface (such as a pouch restraint) comprises a relative thin and/or flexible material which tends to conform to the shape underneath. It is a potential advantage for the cover appearance if the underlying surface contains fewer irregularities (for example wrinkles and/or rumpling) which deform the outer covering of the stomal appliance than an arbitrarily collapsed pouch configuration. Optionally, an outer surface of a panel-folded pouch is exposed during wear. It is a potential advantage for such an outer surface to present a regular appearance, for example, for reasons of aesthetics. Control of the collapse pattern of a pouch potentially also allows control of conditions leading to material fatigue which may introduce holes and/or tears.

In some embodiments of the invention, a panel-folded pouch occupies a relative smaller distance in the proximal/distal axis of an ostomy appliance than a pouch collapsed by some other means and/or to some other geometry. It is a potential advantage for the axial distance occupied by the pouch to be small; as this allows, for example, a lower appliance profile. Additionally or alternatively, profile height is potentially freed for structures supporting other ostomy appliance functions such as attachment, sealing, filtering, and/or gas release.

An aspect of some embodiments of the invention relates to the manufacturing of a pouch which is panel-folded at the front of an ostomy appliance. In some embodiments, control of conditions leading to material fatigue allows the pouch to be safely manufactured with a relatively thinner pouch membrane material. A potential advantage of this is cost savings and/or an additional reduction in pouch package dimensions. Other potential advantages include is decreased costs for product liability and/or reduction of faulty units in production.

In some embodiments, machinery from an industry normally outside of ostomy appliance manufacture is adopted for folded ostomy pouch manufacture. Potentially, a panel-folded pouch package opens the possibility to manufacture with machinery adopted from, for example, an industry where automatic folding of paper stock, fabric and/or plastic film is performed. Potentially, this provides cost reduction in establishing and maintaining a manufacturing line.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Reference Embodiments

Figure 1B:
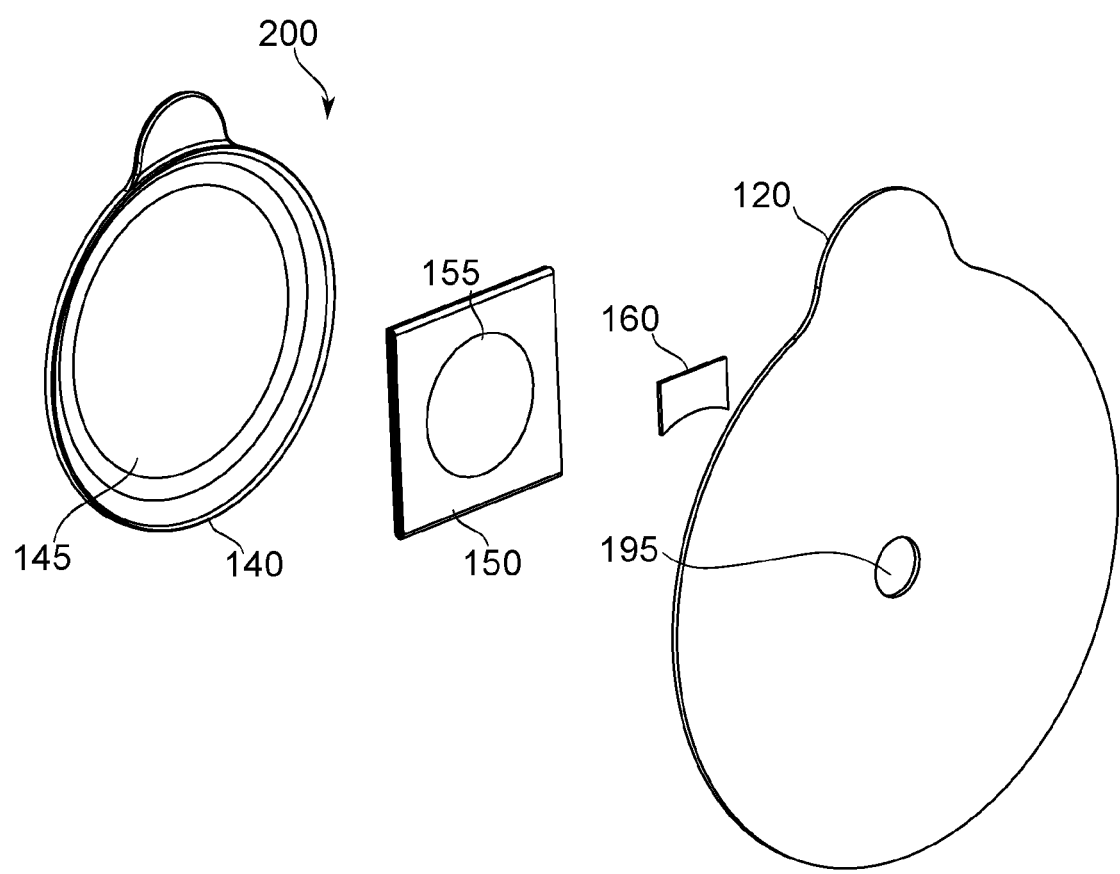

Reference is now made to FIGS. 1A-1B, which schematically illustrate a flat, panel-folded ostomy waste collection pouch 150 held in front of the waste containment compartment of an ostomy appliance 200, according to some exemplary embodiments of the invention. FIG. 1A presents an exploded view from a proximal direction, for example, as if looking toward an ostomate. FIG. 1B presents an exploded view from a distal direction.

In some embodiments of the invention, pouch 150 is kept in its collapsed (folded) state during wear of ostomy appliance 200 until there is a need for evacuation. In some embodiments, a pouch restraint 140 prevents deployment of the pouch until restraint is removed. Optionally, the restraint 140 is removable manually upon a user-determined need. Optionally, operation of restraint 140 is pressure-sensitive, such that a sufficient pressure from within the abdominal cavity (for example, due to flatus or solid/liquid waste) causes its removal.

In some embodiments of the invention, the pouch in its collapsed form is, for example, 40 mm×40 mm×2 mm. In some embodiments, the size is larger or smaller, depending, for example, on the pattern of folding, the unfolded size of the pouch, the thickness of the pouch material, and/or the degree of compression applied to the pouch for storage. In some embodiments, the width and/or length dimensions of the collapsed pouch are, for example, 25-30 mm, 28-35 mm, 33-40 mm, 35-45 mm, 40-50 mm, 45-60 mm, or another range of widths and/or lengths which is narrower, wider, or the same, having range limits which are the same, lower, higher, or intermediate. In some embodiments, the package thickness dimension is, for example, 1-3 mm, 2-5 mm, 3-6 mm, 4-8 mm, 5-10 mm, or another range of thicknesses which is narrower, wider, or of the same range width, the range having bounds which are the same, intermediate, lower, or higher.

It is a potential advantage for the ratio of collapsed volume to deployed volume to be large. Small volumes provide various potential advantages for a collapsed pouch (for example, relative unobtrusiveness, lower bulk, and/or smaller sizes of components required to house and or shield the pouch). Large volumes in contrast, provide a potential advantage for a deployed pouch; for example: larger amount of waste can be contained, a longer time can pass between evacuation events required due to waste containment capacity, and/or less risk of spillage during evacuation.

In some embodiments of the invention, a restrained pouch 150 (and/or for example, some embodiments of other pouches described herein, for example, pouches 400, 814B, 814, 1104, 815, 816, 1015, and/or 1025) is provided which comprises a body having two flat plies of membrane attached at the edges to form a container for waste. In some embodiments, the pouch has a flat-lying configuration against the body when deployed. This is a potential advantage relative to pouches which have a cylindrical or other shape adapted for restraint mechanisms (for example, pouch 1850), as, for a given volume of pouch, there is potentially a lesser distance of protrusion from the body and/or a less-noticeable profile. Another potential advantage is a pouch shape which is less awkward and/or more comfortable against the skin upon deployment and/or filling. Another potential advantage (over, for example, a cylindrical bag which is kept short), is a greater opening distance in a proximal direction for a given volume. Potentially, this provides a larger space for allowing waste entry between, for example, aperture 501 and an overlying ply of pouch membrane.

In some embodiments, pouch restraint 140 comprises a cover for pouch 150. In some embodiments, the pouch is completely covered. In some embodiments, the covering material is thin and/or flexible, such that a proximal portion of the shape of pouch 150 is discernible by vision and/or touch through the covering material. In some embodiments, a non- or partially-covering pouch restraint is used, for example as described hereinbelow in relation to FIGS. 15-17. Optionally, this allows a portion of the shape of pouch 150 to be discernible by vision and/or touch.

In some embodiments, pressure exerted from within the abdominal cavity acts upon pouch 150, potentially causing it to bulge, distend and/or partially inflate. In some embodiments, a resulting change in shape/and or tension is discernible visually and/or by touch. In some embodiments, the change is discernible through the material of restraint 140, for example through a thin cover region 145, or through an aperture of the restraint. Optionally, the change comprises an indication of pressure exerted from within the abdominal cavity. In some embodiments, exerted pressure is indicated relative to no elevation of pressure over atmospheric pressure, the threshold pressure elevation to produce a discernible indication being, for example, 20-30 mmHg, 25-40 mmHg, 30-50 mmHg, 40-60 mmHg, 50-100 mmHg, 75-125 mmHg, 100-150 mmHg, 125-200 mmHg, or another broader or narrower range of pressures having the same, intermediate, and/or higher or lower pressure range boundaries.

Indicating and/or sensing of elevated intra-abdominal pressure is a potential advantage for determining a need to relieve pressure, for example by waste evacuation and/or gas release. In some embodiments, it is a potential advantage for determining that automatic release of the pouch 150 from its restraint 140 is imminent. Sensing internal pressure through the material of a pouch is a potential advantage for a directness of sensing, and/or for simplicity and/or cost of manufacture. It is a potential advantage for a pouch to be configured so that pressure is transmitted regularly and predictably through its material, either to an outer surface of the ostomy appliance, or to a receiving surface of an indicator such as a cover region 145, and/or a restraint 140.

In some embodiments, triggering of automatic release of restraint 140 comprises shape distortion due to distension of restraint 140 under pressure from within the abdominal cavity. Pressure exerted on pouch 150, in some embodiments, is transmittable to the restraint 140 through the material of pouch 150. Optionally, this transmitted pressure causes shape distortion of restraint 140 leading to its release. In some embodiments, the release pressure is, for example, 40-60 mmHg, 50-100 mmHg, 75-125 mmHg, 100-150 mmHg, 125-200 mmHg, or another broader or narrower range of pressures having the same, intermediate, and/or higher or lower pressure range boundaries. It is a potential advantage for a restraint 140 to be automatically released under conditions of sufficiently elevated pressure, for example, for reasons of safety.

Reference is now made to FIGS. 3A-3D, which illustrate the appearance of arbitrarily- and pattern-folded pouches 351, 352 with and without a cover-restraint 340, according to some exemplary embodiments of the invention. In FIG. 3A, ostomy assembly 301 comprises an arbitrarily folded pouch 351 (uncovered in FIG. 3B) which deforms thin and flexible material of cover-restraint 340 so that it presents a wrinkled and disorganized surface to an observer. In FIGS. 3C and 3D, pouch 352 is folded into overlapping, approximately square panels, such that the underlying package appearance is more regular. It is a potential aesthetic advantage for the portion of pouch 150 which is discernible from a proximal side of the ostomy appliance 200 to present a regular surface.

It is a potential advantage for a pouch 150 to be packaged such that pressure is reliably transmitted to a restraint 140 for safety release. Potentially, a predetermined range of safety release pressures may be thereby reduced to a smaller tolerance. In an investigation by the Applicants—comparing release pressures for configurations similar to those of FIGS. 3A-3B and 3C-3D—the folding pattern of FIGS. 3C-3D was found to provide this advantage.

For example, for a given restraint design, an arbitrarily folded pouch was found to be released in some embodiments at an average of about 140 mmHg, with a standard deviation of about 30 mmHg (N=10). An exemplary square folded pouch, in contrast, was found to be released, in some embodiments, at about 120 mmHg, with a standard deviation of about 10 mmHg (N=10). In some embodiments, the relative standard deviation of deployment pressure to average deployment pressure is, for example, no more than 5%, no more than 10%, no more than 15%, no more that 20%, or no more than an intermediate, larger, or lesser relative standard deviation. It is a potential advantage for the release range to be narrower, for an improved reproducibility of release. Optionally, the release average is predetermined to a higher average level when there is more confidence that a safety limit will not be exceeded before release. This is a potential advantage to reduce unnecessarily early deployments by automatic release.

Returning now to FIGS. 1A-1B: in some embodiments of the invention, pouch 150 is attached to a housing 123 protruding from ostomy wafer 120. In some embodiments, an aperture 155 in the pouch 150 is configured to be in fluid communication with the stoma, which penetrates or is behind an opening 195 in the ostomy wafer 120. In some embodiments of the invention, the size of opening 195 is adjustable by a user to accommodate a stoma, for example by cutting away and/or deforming the material of the ostomy wafer.

In some embodiments of the invention, material of pouch 150 comprises a portion which is in contact with and/or attached to a filter element 160. It is a potential advantage for simplicity of construction for a pouch to be a portion of a filter holder. Aspects of pouch operation in association with a filter element are described, for example, in U.S. Provisional Application 61/884,256 by the Applicant.

Figure 2A:
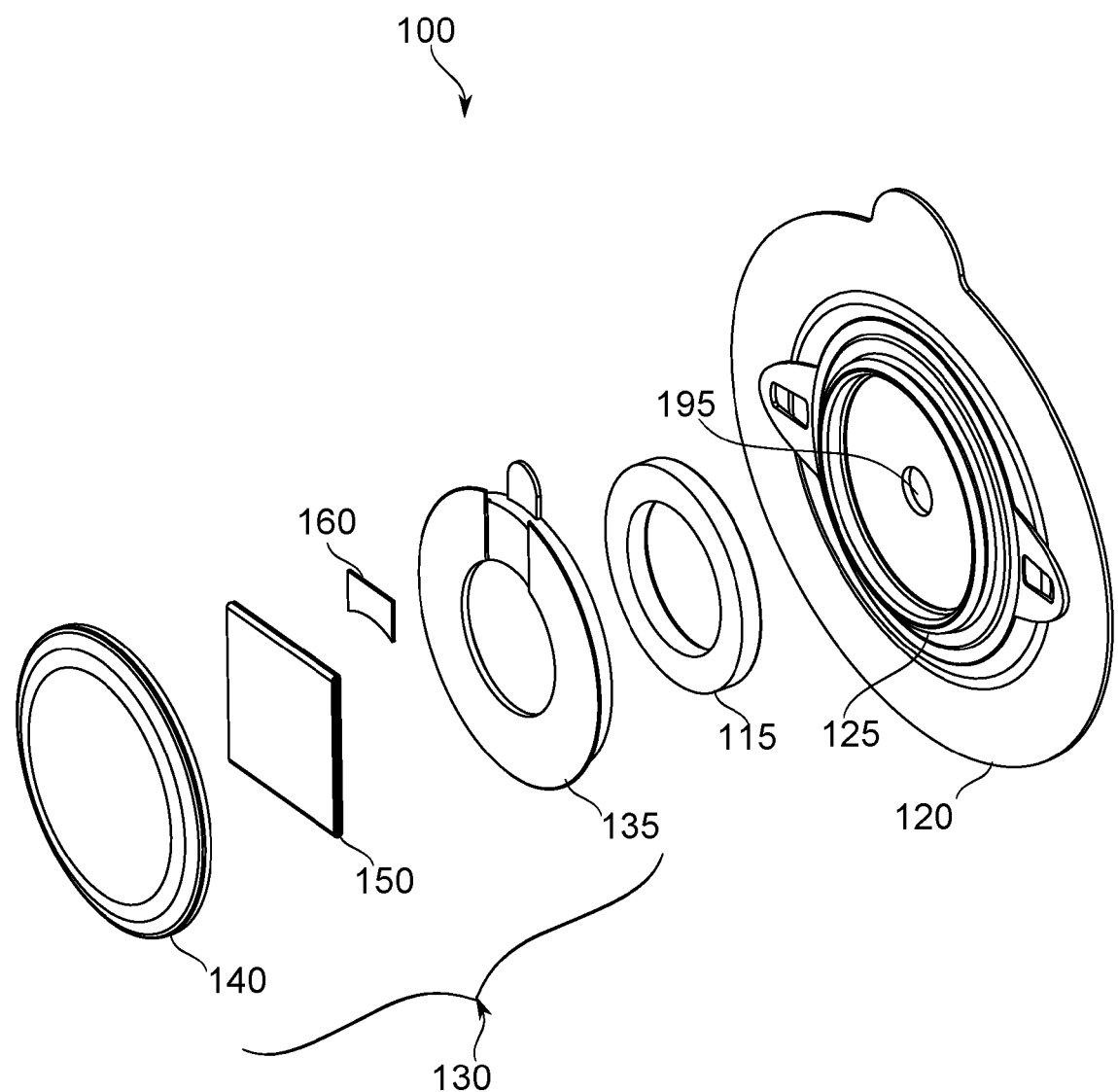
FIGS. 2A-2B illustrate an ostomy stack having a modular configuration and providing an internal chamber sized to accommodate various diameters of moderate to high stoma, according to some exemplary embodiments of the invention.
Figure 2B:
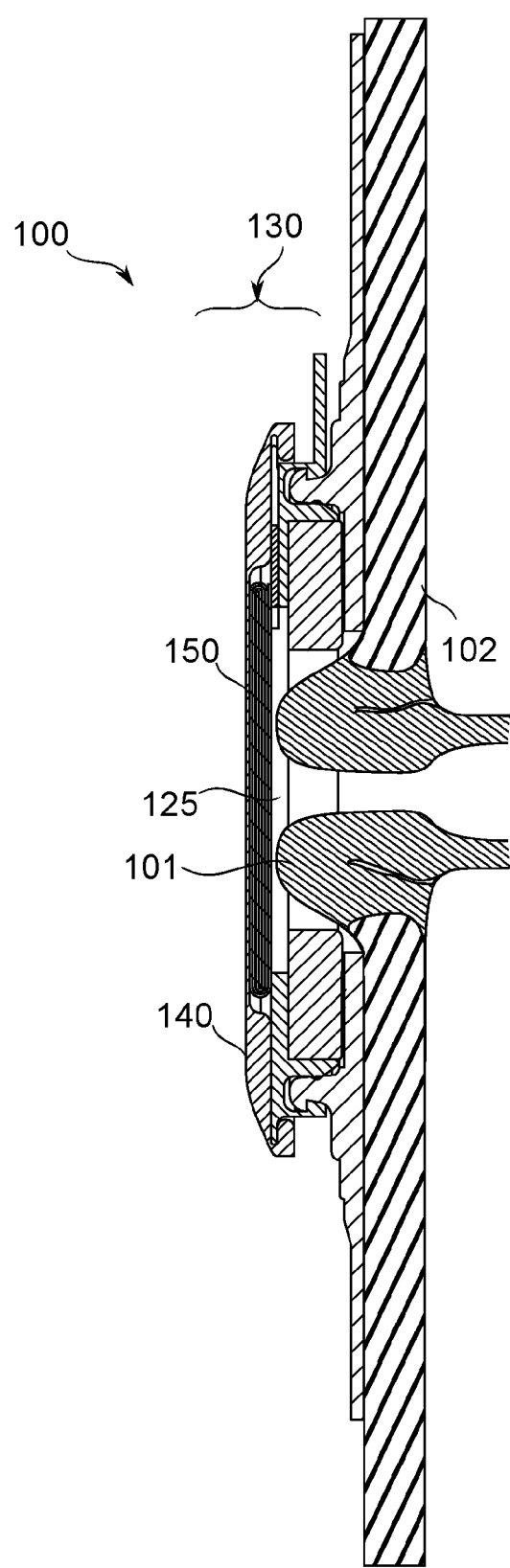

Reference is now made to FIGS. 2A-2B, which illustrate an ostomy stack 100 having a modular configuration and providing an internal chamber sized to accommodate various diameters of moderate to high stoma, according to some exemplary embodiments of the invention.

FIG. 2A, for some embodiments of the invention, illustrates an exploded schematic view of an ostomy stack sub-assembly 130 comprising restraint 140, pouch 150 and filter element 160; as well as ostomy adaptor housing 135. Housing 135, in some embodiments, attaches to ostomy wafer 120 at attachment element 125. Optionally, sealing element 115 is held between adaptor 135 and ostomy wafer 120. In some embodiments of the invention, sealing element 115 occupies space around wafer aperture 195, through which a stoma 101 may protrude when the ostomy appliance is in use. In some embodiments, a sealing element 115 reduces volume within a stoma-enclosing chamber, and/or comprises a barrier between waste exiting the stoma and tissue which is potentially irritated by the waste. A potential advantage of a sealing element 115 is improved hygiene within the stomal enclosure. Optionally, aperture 195 is adjustable as described hereinabove. In some embodiments, sealing element 115 is adjustable in size, for example, by selection from a range of available sealing elements, and/or by being inflatable, collapsible, and/or moldable. A potential advantage of an adjustable sealing element is an improved fit to a particular stomal anatomy, leading to improvements in sealing and/or waste exclusion.

In some embodiments of the invention, ostomy pouch 150 defines a proximal wall of the chamber 125 within which the stoma 101 is contained (for example, as in the cross-sectional schematic view of FIG. 2B). In some embodiments, pouch 150 is folded such that the body of the pouch 150 extends proximally away from a smooth inner wall. Optionally the pouch wall is flat. Optionally, the pouch wall adopts a curve along one or two axes of curvature to more closely enclose the stoma. In this case, the "substantial flatness" of the pouch is optionally considered as being relative to deviations from a configuration which is flat against the shape of a predetermined overall curvature having a radius, for example, >30 mm, >40 mm, >60 mm, or greater than another intermediate, smaller, or larger curvature. It is a potential advantage for a pouch to be collapsible with sufficient consistency that it can be positioned to occupy a volume at and/or outside of a clearly defined inner boundary of the stoma-enclosing chamber. In some embodiments, a consistently formed collapsed pouch package is brought close to the stoma to restrict the volume into which waste can be discharged. Potentially, the package proximity is determined to approach the stoma within a near predefined distance, without chafing and/or pressing against it during wear. It is a potential advantage to avoid chafing and/or pressing, to reduce injury to the stomal tissue. In some embodiments, the distance between stoma and pouch wall is, for example, 0.5-1 mm, 0.8-1.5 mm, 1-2 mm, 1.5-3 mm, 2-5 mm, 3-7 mm, a range comprising another larger or smaller distance, and/or a range comprising a wider, narrower, or intermediate extent of distances.

It should be noted that stoma height varies from ostomate to ostomate. It is a potential advantage to make available a range of positioning heights for pouch 150, for example by adjustment of the adaptor or wafer height, and/or by making available different adaptor and/or wafer sizes for selection according to need. A clearly defined proximal position for ostomy pouch 150 potentially allows more accurate specification and/or determination of the internal height which a given ostomy appliance configuration is appropriate for.

Optionally, a biocompatible gel or other filling material—such as petroleum jelly—is spread within chamber 125. Optionally, it is spread, for example, on the inner surface of pouch 150. Optionally, it is spread thickly enough to form a bridge which seals between pouch 150 and stomal tissue 101. Potentially, the filling material protects against occasional contacts with pouch 150, such as may occur from time to time due to motions during use. It is a potential advantage to provide a seal between the stoma and the pouch, as this may serve to resist the intrusion of waste into portions of the stoma-enclosing chamber 125 which lead to tissue which waste may irritate, such as skin 102. It should be noted that chamber 125 is ordinarily filled by gas (for example air and/or flatus), which must be displaced in order for waste to intrude into the stoma-enclosing chamber 125. It is a potential advantage to restrict the freedom with which this gas moves within the chamber, as this assists in preventing the intrusion of waste irritants.

A potential advantage of retaining a pouch in a collapsed configuration is that the material of the pouch need not be in prolonged contact with the skin during wear, as, for example, may be the case with bag that ordinarily hangs open from the stoma. Benefits potentially associated with this are reduced chafing and/or removal of a need to cover a pouch material with an outer lining for reducing chafing.

In some embodiments, pouch film material is made of a commercially available polymer film. In some embodiments, the film is opaque to prevent waste content from being visible. In some embodiments, the pouch is colored, for example, to blend in with skin tones and/or clothing. In some embodiments, the thickness of the pouch film material is, for example 20-40 µm, 30-60 µm, 40-100 µm, 80-200 µm, or another wider or narrower thickness range, having bounds the same, intermediate, lower, or higher. The pouch material, in some embodiments, comprises, for example: ethylene-vinyl acetate copolymer, polyurethane, polyamide, polyvinylidene chloride, and/or stacked layers of such polymers made, for example by co-extrusion, and/or another polymeric composition suitable in properties such as strength, flexibility, and manufacturability for use as an ostomy waste collection pouch.

In some embodiments of the invention, most of the waste pouch material is protected from contact with waste until after a deployment event for waste evacuation. In some embodiments, protected pouch material comprises material which is biodegradable, compostable, and/or degrading in water (the degrading being slow enough to permit time for evacuated waste disposal). This provides a potential advantage for allowing a degradable and/or compostable portion of a pouch and its waste contents to be disposed of directly to a sewage system.

In some embodiments, for example, portions of the pouch in direct contact with waste during wear comprise a relatively tough (for example, thick and/or non-reactive) polymer film. In some embodiments, pouch portions—for example, portions which are normally in contact with waste for a relatively short time before disposal, but potentially the entire pouch—comprise a degradable polymer. The degradable polymer is, for example, an additive-modified polythene, and/or a starch-based polymer such as polylactic acid, polyvinyl alcohol, polycaprolactone; and/or another material which is degradable in the environment in minutes, hours, days and/or months. Optionally, an outer film layer providing initial mechanical strength is rapidly degradable in water. Optionally, a thin inner film is more resistant to degrading by contact with waste. Potentially, the inner film protects the outer film from degrading before disposal in a sewage system. Upon disposal, in some embodiments, the outer film degrades in water, leaving a relatively insubstantial inner film which is susceptible to mechanical breakage and/or later slower degradation in the environment. A sewage-system compatible pouch film is a potential advantage for easier disposal of evacuated waste together with a portion of the pouch that contains it.

Folding

Reference is now made to FIGS. 4A-4F, which illustrate a method of pouch folding, according to some exemplary embodiments of the invention.

Figure 4A:
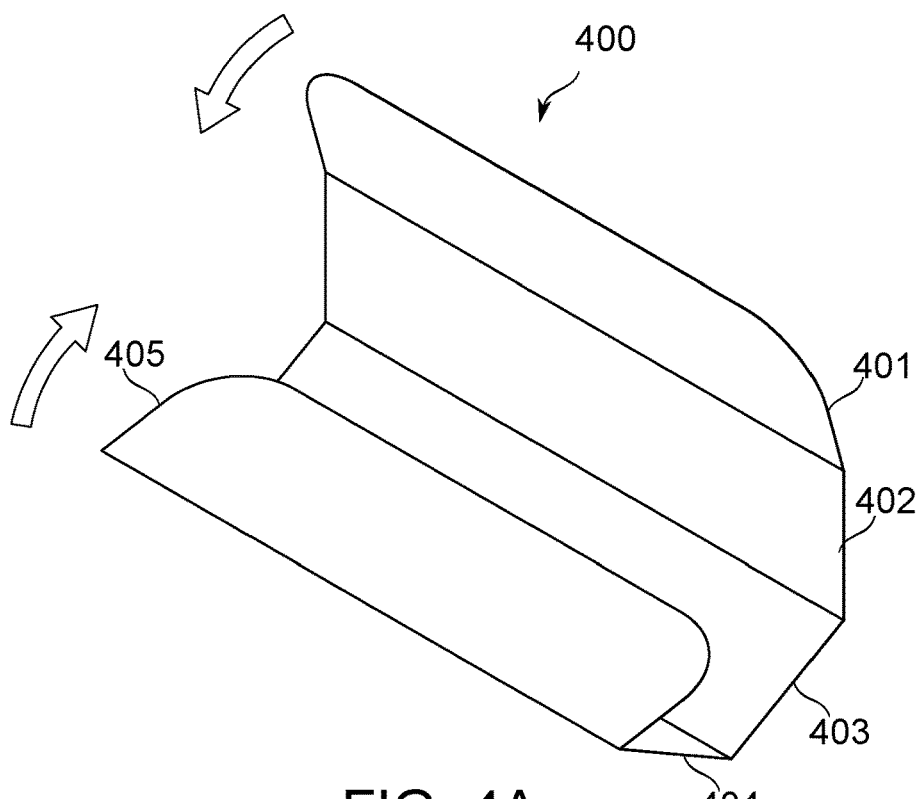
FIGS. 4A-4F illustrate a method of pouch folding, according to some exemplary embodiments of the invention.
Figure 4B:
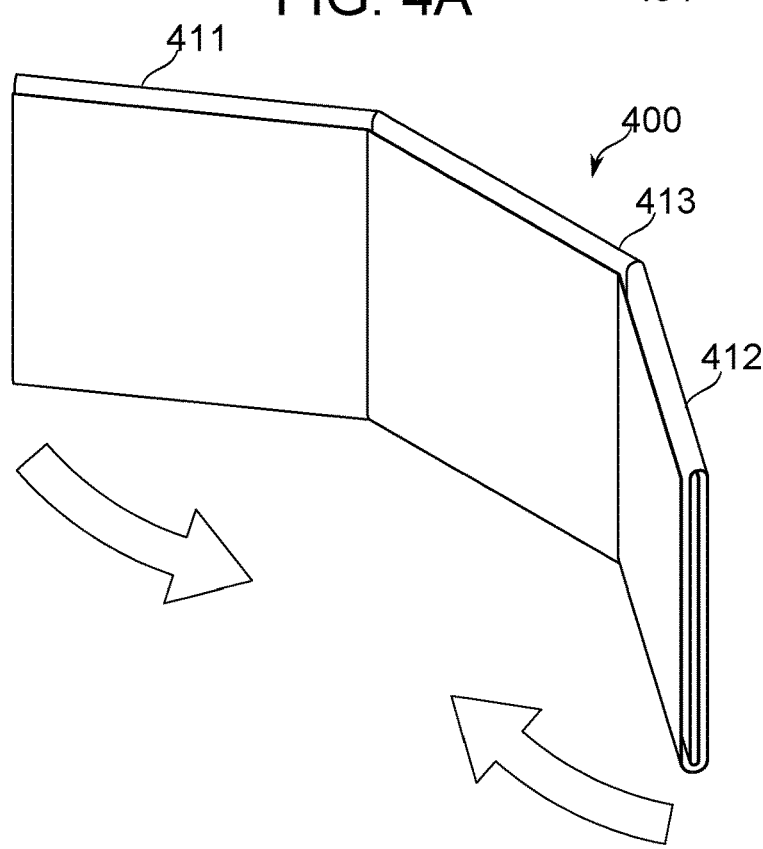
Figure 4C:
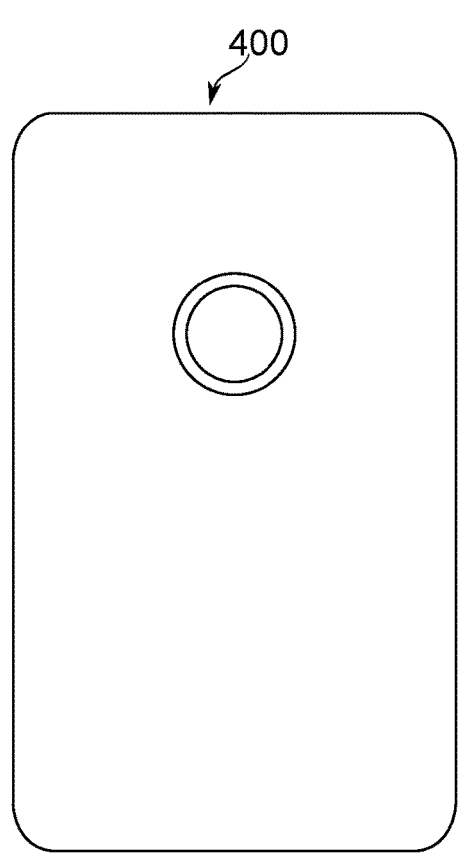
Figure 4D:
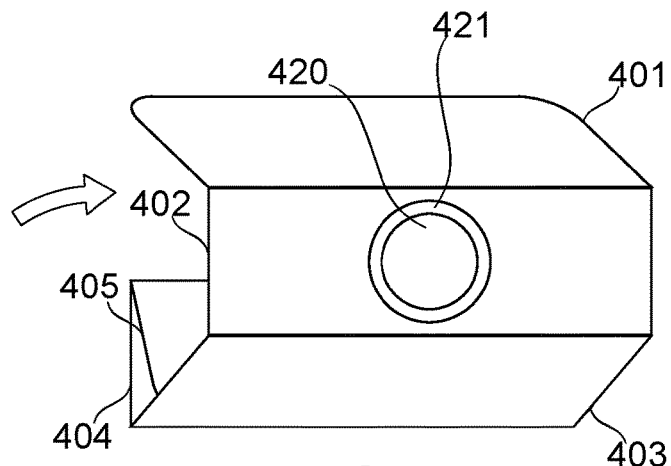

FIGS. 4A and 4D, for some embodiments, illustrate from both distal and proximal views folds made perpendicular to the length of a pouch 400 (FIG. 4C), which in this example is sized in a ratio of about 5:3 length:width. In some embodiments, a top panel 401 is folded down over the panel 402 comprising the pouch intake aperture 420. Panels 403, 404, 405 are folded up over panel 401 from below.

Figure 4E:
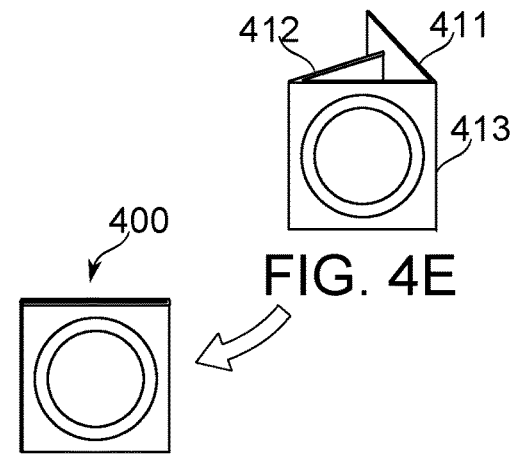
Figure 4F:

FIGS. 4B and 4E, for some embodiments, illustrate folding the wing panels 411, 412 inward to central panel 413 after the folds of FIG. 4A are made. FIG. 4F illustrates the final package from a distal viewpoint.

Aperture 420, in some embodiments, is sized to receive waste from a stoma so that it freely enters pouch 400 (or any other pouch as described herein) when said pouch is in a deployed configuration. The smallest distance across of aperture 400 is, for example, 18-24 mm, 20-25 mm, 24-30 mm, 25-40 mm, or another wider or narrower range of diameters having the same, intermediate, larger, or smaller boundaries. In some embodiments, the longest distance across of aperture 400 is the same as the smallest distance across, or larger by up to 5 mm, 10 mm, 15 mm, 20 mm or another larger, smaller, or intermediate length. The shape of aperture 400 is, for example, circular, oval, quadrilateral, or another shape. In some embodiments of the invention, aperture 420 is larger than an aperture of the housing to which it attaches. In some embodiments, aperture 420 is smaller than an aperture of the housing to which it attaches. In some embodiments, the difference in aperture sizes across the aperture opening is, for example, ±0-1 mm, ±1-3 mm, ±2-5 mm, ±4-7 mm, ±0-14 mm, or another wider, narrower, or same-width range of relative sizes having boundaries the same, intermediate, larger, or smaller.

In some embodiments, the relative area of the aperture package cross-section perpendicular to the distal-proximal axis, and/or the surface area of the folded panel which comprises the aperture, is, for example, no more than 50% larger than the aperture surface area. In some embodiments, the difference in said surface areas is, for example, <5%, <10%, <25%, <50%, <75%, <100%, and/or no more than another surface area size difference which is intermediate, smaller, or larger.

Aperture 420, in some embodiments, is associated with mounting frame 421. In some embodiments, mounting frame 421 allows pouch 400 (or another pouch, for example, as described herein) to be worn attached to an ostomy appliance. Attachment is, for example, by adhesion, mechanical restraint and/or welding.

In some embodiments, mounting frame 421 allows pouch 400 (for example) to be supplied independently of an ostomy appliance to which it is attachable and/or optionally detachable. In some embodiments, mounting frame 421 is a ring attached to the membrane of pouch 400. While frame 421 is schematically depicted as a ring, it should be understood that in some embodiments, mounting frame 421 has a non-circular shape. In some embodiments, mounting frame 421 is a different size and/or shape than aperture 420. In some embodiments, the outer edges of mounting frame 421 comprise the outer edges of panel 413. In some embodiments, mounting frame 421 is larger than panel 413 in at least one dimension. Optionally, frame 421 is omitted and attachment is made directly, for example, to an ostomy appliance housing such as an adaptor, wafer, or ostomy appliance cap.

Reference is now made to FIGS. 5A-5F, which illustrate variations on the folding pattern described in reference to FIGS. 4A-4F, according to some exemplary embodiments of the invention.

In some embodiments, aperture 501 is located near the top-center of a pouch 814 (FIG. 5A), such that it is folded into a panel at an edge of the pouch. In some embodiments, aperture 501 is located on an interior panel of a pouch 814B (FIG. 5B).

It is a potential advantage for the aperture to be near the top of the pouch, as more of the volume is then located below the stoma, available for filling by gravity. The waste is potentially further from the opening after filling, and this in turn may reduce a risk of spillage and/or back-flow through aperture 501. Alternatively, a mid-seated aperture 501 potentially allows a greater opening distance in a proximal direction (larger space between aperture 501 and the pouch membrane that overlies it). Additionally or alternatively, a shorter down-hanging length is potentially more manageable for an ostomate with a relatively low-situated stoma, while maintaining the same total pouch volume. It is to be understood that, except as indicated herein, pouch patterns represent folds and/or creases to be made on pouches comprising two plies of a membranous material, secured to one another at the edges to create a sealed receptacle for receiving waste. In general, the cut-out shapes of the two plies may be considered as identical (but this should not be taken as limiting), with modifications for the inlet aperture in one ply as necessary.

In some embodiments, the progression from unfolded to folded configuration goes through the three-panel configuration 503, described in relation to FIGS. 4A-4F (FIG. 5E), and then to the folded configuration 504. In some embodiments, folding is first across the width of the pouch (502A, 502B). From these configurations, folding of panels such as end panel 510 may proceed in different ways to the final folded configuration 5F.

A length-first, width-second folding scheme has a potential advantage for transmitting pressure to the proximal side of the pouch, since pressure transmitted by gas potentially need only pass into one folded chamber before it directly presses against the most proximal ply of the folded waste collection pouch.

A potential advantage of a width-first, length-second folding scheme is that a reduced number of plies need to be folded at each panel junction (for example, 6 instead of 10), potentially reducing fold bulk and/or allowing a neater folding package to be formed.

Reference is now made to FIGS. 5G-5P, which illustrate variations on a 3×6 panel folding pattern, according to some exemplary embodiments of the invention.

In some embodiments of the invention, an ostomy pouch 520 (FIG. 6G), configured to be folded into multiple panels 521, is provided for receiving ostomy waste. In some embodiments, the panels 521 comprise a 3-panel wide, 6-panel high configuration of substantially square panels. Relative differences in panel size are understood to occur, for example, due to the selection of the dimensions of the pouch, the use of some pouch material extent in folding panels over each other, and/or minor irregularities in the folding of the pouch. Differences in the number and arrangement of panels are understood to be comprised in alternative embodiments of the invention; the 3×6 panel embodiment is exemplary. The location of the inlet panel 501 of ostomy pouch 520 (shown centered left-right and spaced one panel away from the top of the pouch) is similarly exemplary.

In some embodiments of the invention, the pouch is folded with a first fold (FIG. 5H) around a crease line 522C, such that equal-sized fold panels 522A and 522B are brought to face against one another. From this point, two alternative fold pathways are illustrated. In the first pathway (FIGS. 5I-5L), the next fold is made around vertical crease line 524C, to bring fold panels 524B and 524A to face each other. Folding around parallel crease line 526C brings fold panels 526B and 526A to face one another, resulting in a 1×3 panel intermediate package. In some embodiments, the package is reduced in lateral dimensions to a 1×1 panel package by a fold around horizontal crease line 528C to bring fold panels 528B and 528A to face each other, and then by a fold around parallel crease line 530C to bring fold panels 530B and 530A to face each other. Properties of the fold pattern of FIGS. 5K and 5L (and its reversal), in some embodiments, are also described in relation to FIGS. 5Q-5Y, hereinbelow.

In the second pathway (FIGS. 5M-5P), the next fold is made around horizontal crease line 532C, to bring fold panels 532B and 532A to face each other. Folding around parallel crease line 534C brings fold panels 534B and 534A to face one another, resulting in a 3×1 panel intermediate package. In some embodiments, the package is reduced in lateral dimensions to a 1×1 panel package by a fold around vertical crease line 536C to bring fold panels 536B and 536A to face each other, and then by a fold around parallel crease line 538C to bring fold panels 538B and 538A to face each other. It should be understood that the two fold pathways are substantially 90° rotations of one another, apart from the first fold. They are somewhat different in operation, however. In particular, the direction of the last fold helps to control how the pouch interacts with the rest of the ostomy appliance, as described also in relation to FIGS. 5Q-5Y. There is also some difference of behavior with respect to gravity, and the pathway of solid-liquid waste through the pouch. This is of particular relevance, for example, when a flatus filter element is provided in the pouch, as described also in relation to FIGS. 21A-21E and 22A-22D.

Functional Effects of Folding Variations

Reference is now made to FIGS. 5Q-5X, which illustrate the effects of two alternative pouch folding configuration on the function of the folded pouch, according to some exemplary embodiments of the invention. Reference is also made to FIG. 5Y, which shows a pouch deployment restraint having regions of different attachment strength, according to some exemplary embodiments of the invention.

In some embodiments, a partially folded pouch (for example, one folded according to the drawings 5G-5J) is folded alternatively into one of a plurality of final configurations. FIGS. 5Q-5X show two alternates, one with a top fold panel or flap 542 folded over a lower fold panel or flap 544 (FIGS. 5R-5T), and one where the top flap 542 is tucked underneath lower flap 544 (FIGS. 5S-5U). These drawings shown both face-on views, and thin-section side views of the pouch as it is folded. In the thin-section views, side wings are omitted for clarity, and horizontal scale is exaggerated to show folding detail. An attachment element 540 is shown schematically to provide a reference indicating the position of the attaching body of a stomal appliance, for example, used in mounting the bag to a stoma. In some embodiments, the lower flap 544 comprises a U-shaped bend of the pouch, while the upper flap 542 terminates in two ends of the pouch.

FIG. 5V illustrates how the different pouch folding patterns bring pouch sections into different relationships with the overall package. Folding pattern 546 corresponds to the situation of FIG. 5T, with horizontal scale exaggerated still more. Panel lettering from A-E represents the relative distance of each panel from the pouch intake aperture. Attention is drawn in particular to the outermost two panels in each case. In folding pattern 546, the outermost elements are as unrelated to one other as the pouch configuration allows. Folding pattern 548, on the other hand, puts two adjacent segments outermost. The crimping orders and distances that crimps span are also different. These features yield differing pouch-expansion properties. In some embodiments, those properties are taken advantage of in relation to setting the detachment properties of a deployment prevention element 560 (FIG. 5Y).

Another difference in the exemplary folding patterns (FIGS. 5W-5X) relates to where the free end of the folded pouch package is positioned. In FIG. 5W, the terminal of top flap 542 end ups located at the bottom-outside of the pouch package. In FIG. 5X, the terminal of bottom flap 544 ends up at the top-outside of the pouch package. In some embodiments, free ends comprise the largest initial inflation volume as flatus enters a pouch. In some embodiments of the invention, portions of the pouch are mutually constrained as each inflates to impinge upon the others. Optionally, relative inflation is controlled by changing the creasing pattern. In some embodiments, a difference in geometry between two folding patterns as a result of partial, pre-deployment inflation leads to differences in deployment behavior. In some embodiments, differences are subject to amplification by the arrangement of other components. For example, a top/bottom differentiated deployment prevention element such as cap cover 560 is provided, with different fold configurations providing pre-deployment leverage focused on different places relative to the differentiated parts of the cap cover 560.

Cap cover 560, in some embodiments, comprises a region of no attachment 556 at one side (optionally, the top side) which comprises a break in a region of attachment 552 located around a periphery. When installed on an ostomy appliance, region 554 corresponds to the position of a folded pouch. Other cap cover embodiments comprise regions of greater or lesser attachment, graded or stepped. Attachment is controlled, for example, by changes in the depth, thickness, and/or flexibility of material used in a provided attachment mechanism.

Figures 5G, 5H:
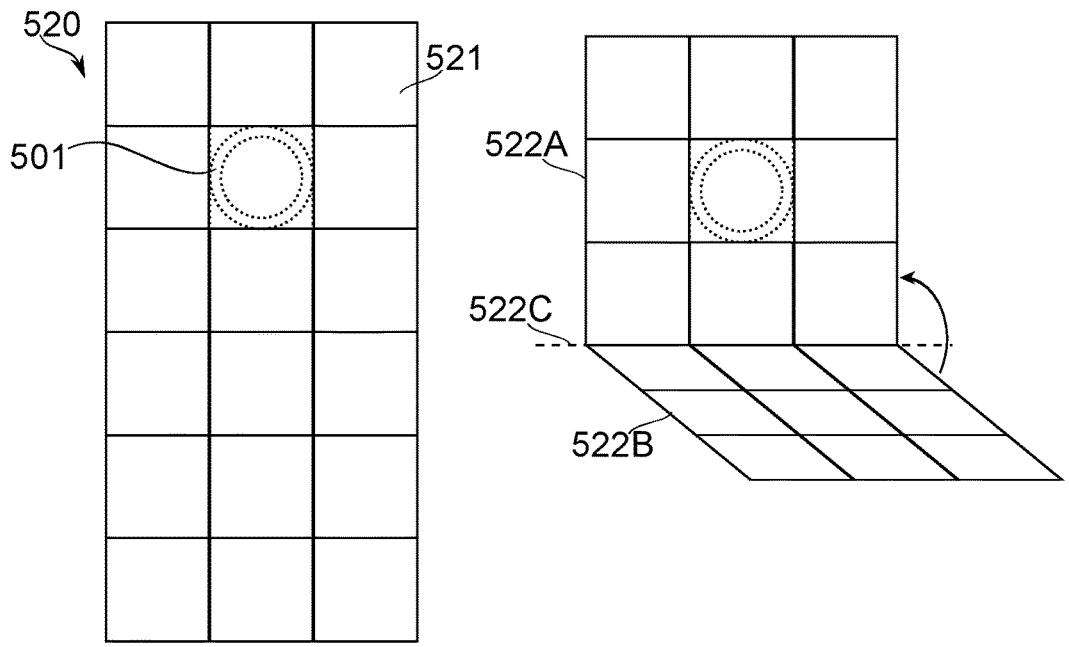
FIGS. 5G-5P illustrate variations on a 3×6 panel folding pattern, according to some exemplary embodiments of the invention.
Figures 5I, 5J:
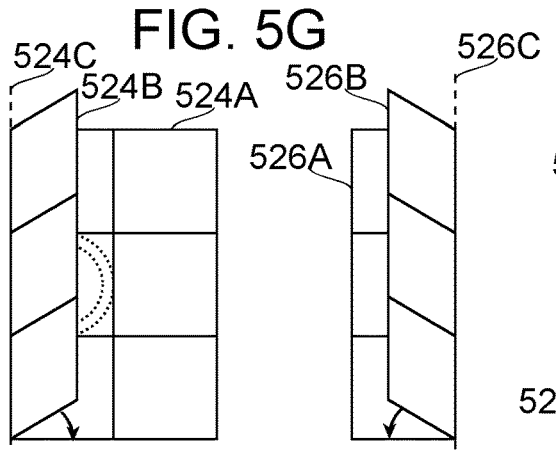
Figures 5K, 5L:
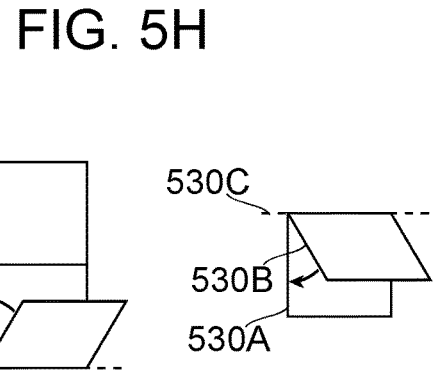
Figures 5M, 5N, 5O, 5P:
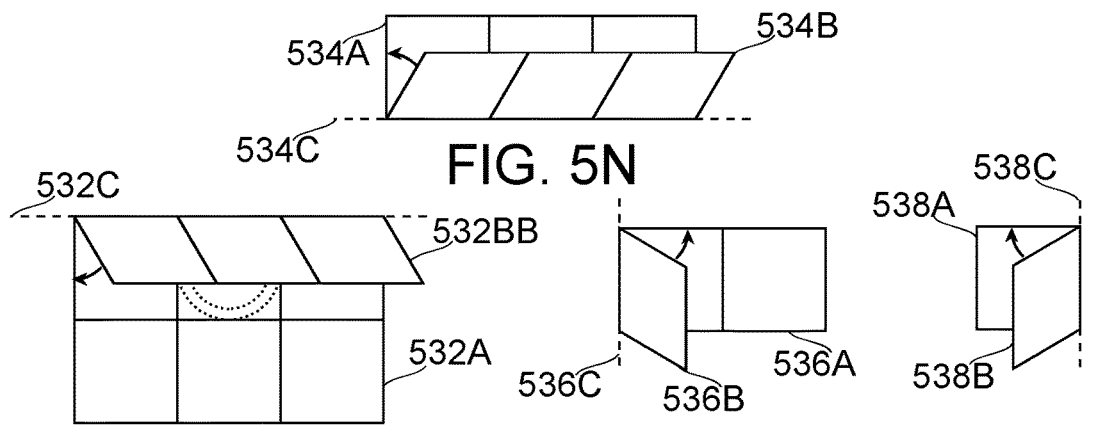
Figure 5Z:
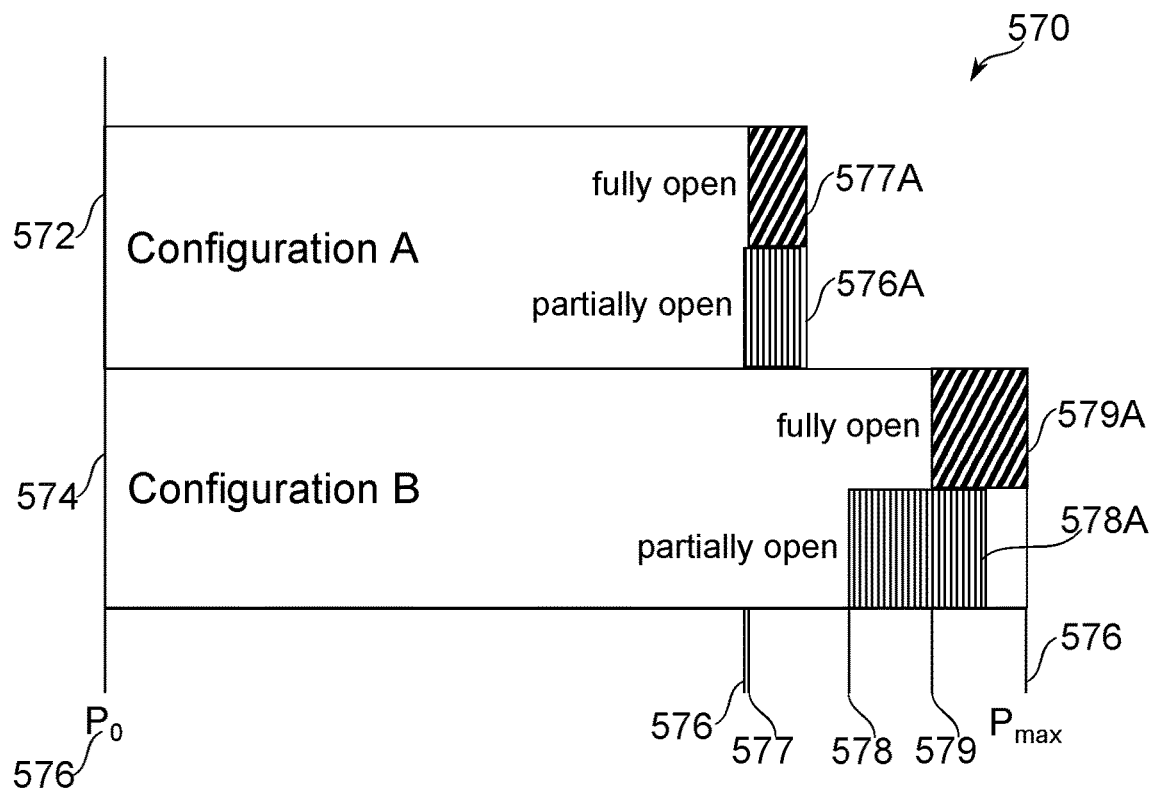
FIG. 5Z is a schematic graph of pressure behaviors resulting from two different configurations of a pouch in combination with a deployment element, according to some exemplary embodiments of the invention.

Reference is now made to FIG. 5Z, which is a schematic graph 570 of pressure behaviors resulting from two different configurations of a pouch in combination with a deployment element, according to some exemplary embodiments of the invention.

The inventors have found a surprising, potentially advantageous array of deployment behaviors associated with providing a pouch configured as shown in FIG. 5W—and different deployment behaviors associated with the configuration of FIG. 5X—in combination with a deployment prevention element such as that of FIG. 5Y. "Configuration A" and "Configuration B" of graph 570 should be understood as relating to configurations comprising a group of behaviors, although they relate as well to the just-mentioned, and potentially to other, device configurations, as described hereinbelow.

The graphed behaviors 572, 574 of Configuration A relative to Configuration B may be described as (1) a relative small difference in time and/or pressure between the beginning of deployment prevention element detachment and full detachment, (2) a relatively narrow range of pressure within which full detachment reproducibly occurs, and (3) a relatively low pressure threshold for automatic deployment. The pressures within which full deployment occurs are indicated by bars 577A, 579A; the pressures within which deployment element detachment begins are indicated by bars 576A, 578A. Tick marks 576, 577, 578, 579 indicate the onset of each of these bars as pressure 576 increases from an initial pressure $P_0$ to a maximum pressure $P_{max}$. A difference between Condition A and Condition B which is implied but not fully captured by the graph is that deployment in Configuration B comprises a "peeling" behavior, in which the deployment prevention element gradually releases from the cap, while deployment in Configuration B comprises a "popping" behavior, in which the deployment prevention element releases suddenly.

In some embodiments of the invention, Configuration A corresponds to behavior in a configuration where the pouch is folded as in FIG. 5W, and Condition B corresponds to behavior in a configuration where the pouch is folded as in FIG. 5X. In each configuration, the cap cover 560 (serving as a deployment prevention element) is oriented with the region of reduced attachment oriented to the top.

While several points of difference have been noted between FIG. 5W and FIG. 5X, it is of particular note that deployment "peels" when the free end is closest to the region of low attachment of cover 560, and "pops" when the free end is away from this region. In some embodiments, peeling comprises a progressive detachment along an extent of attachment, wherein a given abdominal pressure is sufficient to cause detachment along a particular region of the extent, that region increasing as abdominal pressure increases, up to a point of full detachment. In some embodiments, any weakening of attachment near regions already pressure-detached is insufficient for further detachment to proceed, until a further increase in abdominal pressure occurs. In some embodiments, peeling begins from a region of weakest attachment, and proceeds to a region of stronger attachment. In some embodiments, peeling begins from a region most directly receiving abdominal pressure, and continues to regions receiving less direct pressure (and/or less torque due to pressure) as maximum pressure increases.

In some embodiments, popping comprises sudden detachment, wherein a given abdominal pressure, upon dislodging attachment of a restraint at one point, leads catastrophically to the loss of attachment at other points. For example, loss of attachment at the first point weakens adjoining attachment, such that it also falls below the strength needed to withstand the current pressure.

Other observed deployment properties, however, are not obviously and/or unambiguously related to this or another specific difference. Insofar as this is the case, the behavior configuration overall may be regarded as surprising. It is nevertheless to be understood that, on the basis of this initial suggestion, other configuration behaviors related to deployment are obtainable, in some embodiments of the invention, by varying one or more of the pouch folding pattern, the orientation of the deployment prevention element, and/or aspects of the construction of the pouch, and/or deployment prevention element. The configuration behaviors potentially include both intermediate and relatively more extreme versions of the behaviors schematically indicated in FIG. 5Z.

"Peeling" deployment is potentially reversible, especially during its initial phases. Advantages of "peeling" deployment include being a last-ditch warning to an ostomate that full deployment is imminent. The relatively slow opening time allows the ostomate to take responses including gas venting (allowing potential reversal), addition of counteracting hand pressure (allowing potential delay), and/or withdrawal to a more private location (mitigating the embarrassment of a sudden deployment). It should be noted that this potentially restores to the ostomate a function of the rectum, which not only indicates that there is a need for evacuation, but also indicates this with increasing urgency according to the level of the need.

Advantages of putting automatic deployment off to a higher pressure are potentially realized for an ostomate undertaking strenuous activity. Internal pressure is potentially variable as a function of exertion, leading to an advantage for pushing the pressure of automatic deployment to a high level that avoids some pressure spikes. "Peeling" behavior is also potentially advantageous in such situations, where an additional action potentially available to the ostomate is to reduce the level of activity. It thus a potential benefit for "peeling" deployment and a higher threshold of automatic deployment to be linked.

In contrast, it sometimes is a potential advantage to reduce a need for self-monitoring, for example, during sleep. A lowered automatic deployment threshold potentially increases safety, for example, to mitigate the effects of sleeping in a position where bed pressure tends to hold a cover in place. Furthermore, sleeping is typically private, and the risk of a sudden pressure spike is less due to lowered activity, so added safety comes at a lowered price. The "pop" behavior potentially serves, by its suddenness, as an alert to a somnolent ostomate to evacuate their waste bag. Linkage of the two deployment behaviors is thus again a potential benefit, as they have potential benefits under similar conditions.

Reference is now made to FIGS. 6A-6F, which illustrate cross-sectional views of various folded configurations of the pouch, according to some exemplary embodiments of the invention.

Figure 6A:
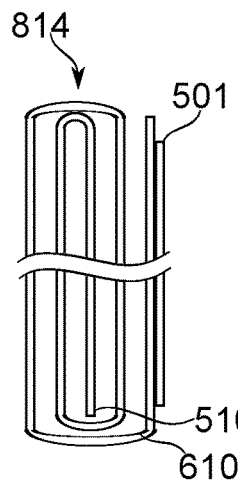
FIGS. 6A-6F illustrate cross-sectional views of various folded configurations of the pouch, according to some exemplary embodiments of the invention.
Figure 6B:
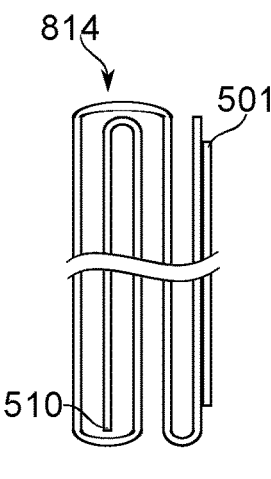
Figure 6C:
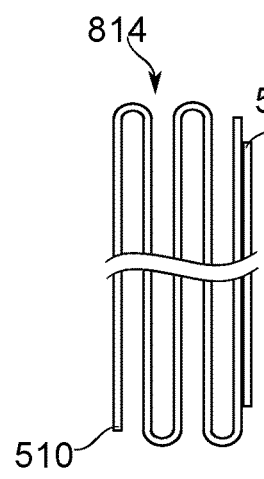

FIGS. 6A-6C show folded configurations along a 5-paneled section of pouch 814, with different relative performance characteristics, depending on the depth order and/or direction of panel folding. The cross-sectional view of FIGS. 6A-6D is, for example, as if from the side of the appliance as worn. All panels of FIG. 6A-6F are shown with the mid-regions of pouch packages removed, in order to emphasize details of the folding arrangements near the package edges.

The panel folding configuration of FIG. 6A, for example, includes a connecting region 610 which connects the second panel, positioned as the proximal surface of the package, to the distal-most aperture panel 501. This configuration allows the first unfurling of the package to carry the whole bag downward with an outward swing, potentially impelled by the weight of waste entering the bag. Subsequent unfurling continues to unroll outward from the ostomate body up to the last panel 510. The result, in some embodiments, is that full deployment is relatively unobstructed by the body of the ostomate. Furthermore, pressure, particularly gaseous pressure, which enters the bag is relatively easily conducted (through just one connecting segment) to the most proximal portion of the folded pouch, where it can exert pressure against a deployment restraint and/or pressure indicating surface.

FIG. 6C, in contrast, folds each panel against the previous one in distal to proximal order, top-to-bottom. The bulk of a large spanning segment is thereby avoided, and the resulting package is more nearly symmetrical near the top and bottom edges. However, pressure sensing is now conveyed through each intermediate segment before it reaches the most proximal part of the pouch package at the pouch end 510. This may be an advantage for allowing deployment to be delayed when this is desired. It should be noted that in a length-first, width-second folding pattern, the most proximal panel may by a laterally-entered panel in any case. Unfolding is in a different pattern, encouraging "snaking" downward, rather than unrolling; this may be preferred, for example, by an ostomate wearing tighter clothing, as it potentially simplifies the operation of ensuring full deployment.

FIG. 6B comprises an intermediate configuration between those of FIGS. 6A and 6C.

Figure 6D:
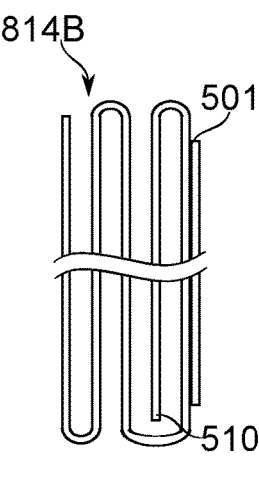

FIG. 6D comprises a configuration of pouch 814B, wherein the aperture panel 501 is in a mid-situated panel along the pouch length. The folding pattern example shown is of the "snaking" type, but a similar range of configuration possibilities exists in this case as for pouch 814. It should be noted that FIGS. 6A-6D, although they show only one pair of plies (as though the pouch were originally folded length-first, width-second), also apply to width-first folded pouch package configurations in some embodiments of the invention.

Figure 6E:
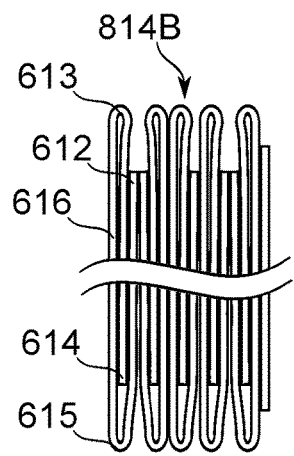
Figure 6F:
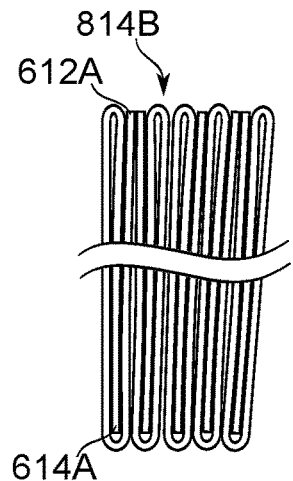

FIGS. 6E-6F show comparative details of two width-first, length-second folded package configurations where all pouch plies are shown in cross-section. Here, the cross-sectional angle is, for example, as if from above the appliance as worn.

In FIG. 6E, the initial trifold is shown with the wing panels 612, 614 being slightly shorter than the central panel 616. Potentially, the use of shortened wing panels leaves an unoccupied space for crimped fold regions of the pouch 613, 615 to expand into. Potentially, this reduces fatigue on the pouch material, which, in some embodiments, potentially allows a thinner membrane to be used without increased risk of pouch rupture.

Comparison of FIG. 6E with FIG. 6F illustrates another potential advantage of using shortened wings, which is that the stacking of the pouch package plies is potentially straighter. A tucked end 614A and an overlying end 612A interact with the crimp regions to affect the thickness of the package differently, an effect which is multiplied, in some embodiments, when several layers are folded together (note the deviation from vertical for the rightmost panels of the figure). It should be understood that the off-center effect is somewhat exaggerated in the drawings due to the abbreviation in vertical scale.

Reference is now made to FIGS. 6G-6L, which illustrate an exemplary shape and folding pattern of a waste collection pouch 1104, according to some exemplary embodiments of the invention.

In some embodiments, the waste collection pouch shape and/or its pattern of folding and/or creasing comprises elements which contribute to the function of the pouch during deployment. It is a potential advantage for pouch deployment from its folded configuration to a fully expanded configuration to occur rapidly and with few steps for the ostomate to perform. The pouch is generally held under clothing, so that a relatively low-profile unfolding sequence is also a potential advantage.

The exemplary pouch 1104 shown unfolded in FIG. 6G is about 11 cm wide by 22.5 cm long (about a 1:2 aspect ratio). In some embodiments, pouch 1104 is collapsed using a width-first (wings-first), length-second folding pattern. The length-wise panel configuration, in some embodiments, is similar to that of FIG. 6C. This is a potential advantage for deployment, as a simple downward tug on the exposed panel end allows "snaking" deployment of the pouch length. Optionally, the wing panels 1116, 1117 are shorter than the central panel, for example as described in relation to FIG. 6E.

In some embodiments, the lower corners of pouch 1104 are cropped, so that diagonal 1110, for example, comprises a portion of the pouch lower border. With the lateral pouch wings 1116, 1117 flat-folded over one another, as in FIG. 6H, a region 1112 comprising only one panel thickness of the pouch remains visible. This is a potential advantage during deployment, as it allows an ostomate to grip the lower end of the pouch without pinching the wings closed at the pouch bottom.

In some embodiments, the folding pattern comprises diagonal creases 1111, which allow triangular sub-panels to be formed in panel 1117. FIGS. 6I-6K illustrate (for example, for a portion of pouch 1104) how triangular sub-panels may be arranged during folding so that wings 1116 and 1117 cross over one another—in one part of the length extent, wing 1116 is exposed over wing 1117, and in another, the exposure is reversed. During deployment, the folding sequence is potentially reversed, such that triangular panel 1114 lifts panel 1116 away from the central panel. This is a potential advantage to make the pouch wings 1116, 1117, "self-deploy" at least partially in response to lengthwise deployment of the collapsed pouch. Potentially, this makes it easier to fully open the wings. Potentially, filling pressure more easily expands the wings 1116, 1117 to their fully open position once partial self-deployment has occurred.

In some embodiments of the invention, crease-lines 1113 are imposed on the pouch, for example by temporary folding and/or by a creasing iron. In some embodiments, these create half-panels. Optionally, the half-panels are not folded over each other during packaging, but come into use, rather, during deployment. FIG. 6L represents deployment of a half-panel 1118 (along arc 1121) relative to a notional unhinged panel (along wider arc 1123). The proximal direction in the drawing is to the right, where, for example, clothing might be present, restricting freedom of movement. It is a potential advantage for the crease-lines 1113 to act as a hinge during deployment, so that a relatively smaller space and/or force is needed to complete the deployment of the pouch 1104. It should be noted that the pouch material, in some embodiments, distorts during deployment so that it does not literally follow the arcs shown; the hinge nevertheless potentially reduces interference with motion and/or reduced proximal extent during deployment.

Relating now to a method of deployment of collapsed pouch 1104 utilizing several of the features just described: after the end of pouch 1104 is exposed (for example, by removing a restraint and/or cover), the ostomate grips region 1112 and pulls downward. During the downward pull, crease 1113 acts as a hinge, potentially reducing the force needed to displace clothing and/or the outward distance that the pouch extends. As regions comprising the triangular panels formed beyond creases 1111 are reached, the wings 1116, 1117 interact to push one another open. Potentially, pressure from within the stoma is then sufficient to complete deployment, as the bag is at least partially inflated by flatus and/or filled by solid and/or liquid waste.

Reference is now made to FIG. 7, which illustrates the relative sizes of different regular polygon shapes relative to a circumscribing circle and a central aperture, according to some exemplary embodiments of the invention.

Folding in FIGS. 4A-6L is described hereinabove with reference to square 704 and/or rectangular collapsed shapes and/or panels. In some embodiments, another polygon shape is used as the basis of the folding pattern. For example, the folded panels comprise pentagonal 705, hexagonal 706, and/or other regular or irregular shapes.

A package polygon with more sides provides a potential advantage by allowing more room (for a given diameter of circumscribing circle 700) to enclose an aperture 710 therein. For a fixed-size circumscribing circle 700 and aperture 710, this potentially makes more space available for securing the pouch material to another component of the ostomy stack. For a fixed-size aperture 710, a smaller circumscribing circle 700 may be used with a polygon having more sides. This potentially allows a smaller overall diameter for the ostomy appliance, without restricting the size of the filling aperture of the ostomy pouch.

Reference is now made to FIGS. 8A-8C, which show different folding patterns superimposed on pouches of varying shapes, according to some exemplary embodiments of the invention.

FIG. 8B, in some embodiments, shows again an exemplary square-paneled 804 folding pattern for a 5:3 aspect ratio ostomy waste collection pouch 814. To collapse a pouch according to this pattern, in some embodiments of the invention, two substantially parallel length-wise crease lines are fully folded over, and four crease lines perpendicular to these crease lines are fully folded over. Herein, "fully folded", "fully folded over", "full fold", "pinched fold", "pinched-over fold", "doubled-over fold" and the like indicate a fold along a crease region such that surfaces on each side of the crease which are substantially in parallel planes before the folding are brought into a face-to-face configuration by the fold such that they are again substantially parallel. Additionally or alternatively, a full fold comprises a substantially 180° rotation around a crease-line (deviations due to factors such as thickness of material and intervening layers are treated as insignificant for purposes of this definition). In general a "fold" as such should be understood to be a full fold, except as indicated in text or by a drawing. Where a "bend" occurs around a crease line, it may be a fold through an angle substantially smaller than 180°; about, for example, 135°, 90°, 45°, 30°, or another intermediate, larger, or smaller angle. A "crease line" is not necessarily associated with a present fold; for example, it can be a line that defines where a full or bent fold is to occur, and/or has occurred.

A "folding pattern" should be understood as a template for making full and/or bent folds (or the folds themselves), potentially along with unfolded creases as indicated. For a pouch to be "flat-folded" comprises having one or more full folds which double-over two portions of pouch (typically comprising a plurality of plies) around a crease line. Optionally, a "pleat" or "pleated fold" comprises one or more plies of pouch material fully folded around a crease-line. A "panel", as the word is used herein, should be understood as a region of a pouch bounded by pouch edges and/or crease-lines, except as modified hereinbelow. The extent of a panel may be over a full package surface and/or cross-section (for example, over a full distal or proximal surface of the collapsed pouch package), or over a portion of a package surface and/or cross-section.

In some embodiments of the invention (which may correspond to any of the pouches disclosed herein), a panel itself comprises substantially parallel portions of a plurality of membranous plies—for example a distal ply and a proximal ply—the plies being joined, for example at their edges, to create a sealed container for evacuated waste. In some embodiments, the distal ply and proximal ply portions are coextensive.

In some embodiments, the volume between two plies of a panel comprises a sub-compartment of the pouch. In some embodiments, the sub-compartment is collapsed while the pouch is in a folded configuration. In some embodiments, sub-compartment volumes are at least partially enclosed by bends (which may be comprised in full folds) at crease-lines which define panel boundaries. In some embodiments, sub-compartment volumes are at least partially enclosed by joins between plies.

It should be understood that the number of lines in each direction of a square or rectangular folding pattern may be any number suited to form the desired package size, for example, 1, 2, 3, 4, 5 or more lines substantially parallel to a first pouch direction, such as but not limited to the length or width of the pouch; and/or, for example, 1, 2, 3, 4, 5 or more lines substantially perpendicular to first pouch direction. It should be understood that the orientation of crease lines relative to the pouch overall dimensions may be selected to be any orientation. For example, a folding pattern composed of squares may be rotated 45° to form diamond-shaped panels. In some embodiments of the invention, irrespective of fold angle and/or overall pouch shape, the number of folded panels is, for example, 2, 4, 6, 8, 12, 20, 30, 34, 50, 54, 100, or another intermediate or larger number of folded panels. The number of layers into which panels are folded is, for example, 2, 3, 4, 5, 6, or a larger number of folded layers. In some embodiments, the number of layers is larger by a factor of 2, 3, 4 or more, depending, for example, on the number of mutually orthogonal and/or cross-angled folds made, and/or on the number of plies in each folded panel.

Herein the terms "substantially perpendicular", "substantially parallel", and "substantially at an angle of X°" are used in describing the direction of fold lines in a folding pattern, where X is, for example, 45°, 60°, 72°, 90°, 108°, 120°, or another angle. The meaning of "substantially" in this context indicates that the angle is characteristic of a particular folding pattern, and is followed with the tolerances typical of a folded sheet of thin material to form an intended shape after a fold. The tolerances of edge position after a fold which is "substantially" according to some canonical angle are, for example, ±1 mm, ±1.5 mm, ±2 mm, ±2.5 mm, ±3 mm, ±4 mm, ±5 mm, or another intermediate, greater, or smaller tolerance consistent with the formation and function of an intended folded shape. Additionally or alternatively, the tolerances of an angle for folding which is "substantially" according to some canonical angle are, for example, ±1°, ±1.5°, ±2°, ±3°, ±5°, or another intermediate, greater, or smaller tolerance consistent with the formation and function of an intended folded shape. Characteristically, relative angles of crease lines in a folding pattern which is based on a right quadrilateral shape follow the right angle (90°), its multiples (for example 180°), and divisions (for example 45°).

Herein, the term "substantially flat" is used in a first sense to describe the three-dimensional structure of a pouch, for example in the context of a "substantially flat package". In this sense, "substantially flat" indicates a package which is much shorter in one dimension (thickness) than in two other dimensions (length and width). For example, the thickness may be <3%, <5%, <8%, <10%, <15%, or less than an intermediate, smaller, or larger fraction of the shortest dimension in the length/width plane of the folded pouch package.

The term "substantially flat", in the sense of a surface region (for example, a "substantially flat wall"), indicates a surface region of the collapsed pouch package which runs within a geometrical plane, deviating above or below the plane by, for example, <1 mm, <2 mm, <4 mm, <7 mm, or less than another intermediate, smaller, or larger distance. Alternatively or additionally, "substantially flat" indicates a surface having a radius of curvature in any direction at any point away from the edge of the surface which is greater than, for example, 30 mm, 40 mm, 70 mm, 100 mm, or another intermediate, larger, or smaller radius of curvature.

Furthermore, a "substantially flat" surface region is contiguous (made up of a continuous region of a single fold panel), or made up of continuous regions of a relatively small number of partially overlapping and/or adjacent fold panels, for example, 2, 3, 4 or 5 fold panels. A substantially flat surface region moreover comprises a smooth surface region. A smooth surface region, for example, has no sharp wrinkles or creases oriented and/or exposed such that they could cause injury or chafing to tissue of a stoma when positioned for wear.

Herein, "flat" should be understood to mean "substantially flat" as defined hereinabove according to the sense appropriate for the context, except as explicitly modified hereinbelow.

FIG. 8A shows a folding pattern for a pouch 815 having a package shape which comprises a pentagonal panel 805. Characteristically, relative angles of crease lines in a folding pattern which is based on a regular pentagon shape substantially follow the angles associated with the pentagon-108° for inner angles, 72° for outer angles, and various multiples, divisions (for example, 36°), and combinations thereof. FIG. 8C shows a folding pattern for a pouch 816 having a package shape which comprises a hexagonal panel 806. Characteristically, relative angles of crease lines in a folding pattern which is based on a regular hexagonal shape substantially follow the angles associated with the hexagon—120° for inner angles, 60° for outer angles, and various multiples, divisions, and combinations thereof.

It should be understood that these patterns are exemplary and not exhaustive of all possible embodiments of the invention. Other package shapes, sizes, and panel numbers comprise embodiments of the invention as well, as apparent to one skilled in the art working based on the descriptions provided herein. In particular, the basis of a folding pattern need not be a regular polyhedron. Indeed, there need not be a particular characteristic basis shape at all; this is a convenient concept for purposes of exposition.

In general, pouches contemplated as embodiments of the invention have flattened areas comprised within notional smallest-bounding rectangles having several possible widths and lengths. In some embodiments, the pouch smallest bounding rectangle width is about, for example, 2-4 cm, 3-10 cm, 8-13 cm, 10-12 cm, 10-15 cm, 13-20 cm—or a broader or narrower range, having the same, intermediate, and/or greater or lesser width range boundaries. In some embodiments, the pouch length is about, for example, 2-10 cm, 10-17 cm, 15-25 cm, 20-23 cm, 20-30 cm—or a broader or narrower range, having the same, intermediate, and/or greater or lesser length range boundaries. The ratio, in some embodiments, of a pouch's maximum width:maximum length is about, for example, 2:3, 3:5, 1:2, 2:5, 1:3—or another larger, smaller, or intermediate ratio. The pouch capacity for waste and/or flatus, in some embodiments of the invention, is about, for example, 100-200 ml, 150-400 ml, 300-600 ml, 500-800 ml, 700-1200 ml, 1000-1500 ml—or another larger, smaller, or intermediate capacity. In some embodiments, the pouch capacity is about 550 ml.

In some embodiments, amendments to the pouch shape within a minimum bounding rectangle are made. These may comprise, for example, removal and/or rounding of corner regions, contouring to accommodate a folding pattern, and/or another variation from a basic rectangular pouch shape.

Selecting a pouch size potentially comprises weighing of one or more of several considerations, including, for example:

Height of the stoma on the body.

Distance of the stoma to a waistline, belt, lower shirt hem, or other boundary which potentially limits a lower extent of a deployed ostomy pouch.

Weight of contained waste, relative to the security of the means by which the pouch is ultimately attached to the ostomate (for example, adhesive and/or ostomy belt).

Targeted duration and conditions of wear after deployment. For example, brief wear in a private location after deployment potentially permits a length which is more visible under clothing than a deployment which is expected to occur in public.

Targeted amount of waste to be contained by a single evacuation event. Where continence can be kept longer, a larger pouch size may be indicated.

Reference is now made to FIGS. 9A-9F, which demonstrate folding of the pentagonal fold pattern of the pouch 815 of FIG. 8A, according to some exemplary embodiments of the invention. Directions (up, down, behind, forward) and the exact order of folds should be understood as exemplary of one way of creating the package of FIG. 9F; other ways of achieving the same package configuration, or one near to it, also comprise embodiments of the invention, based on the descriptions provided herein.

Figures 9A, 9B:
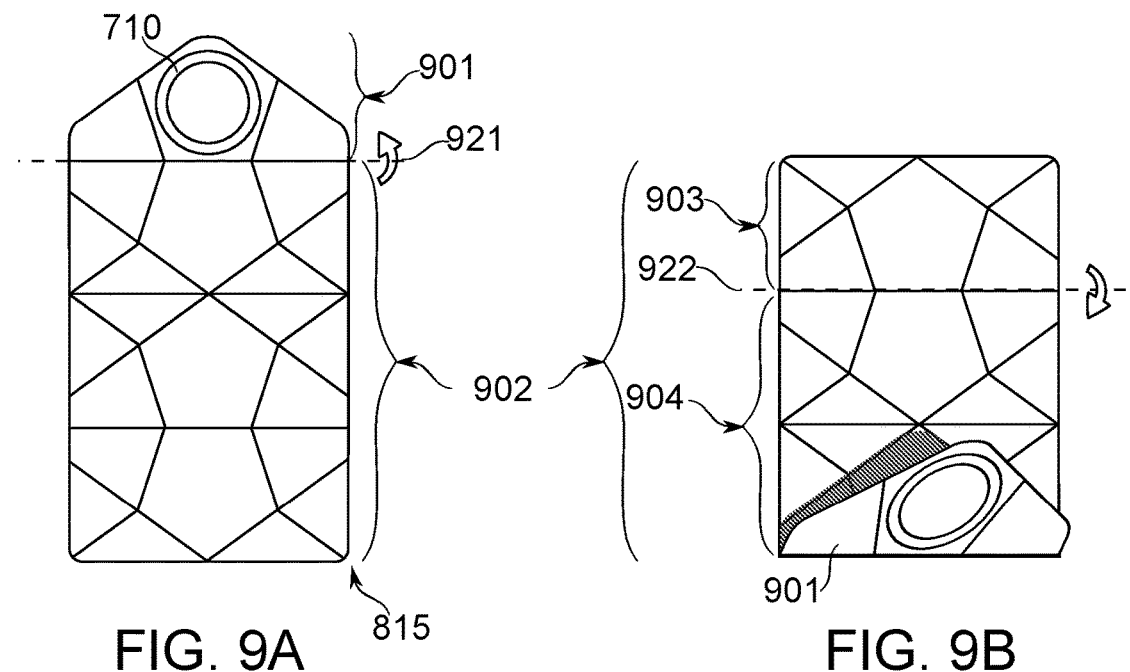
FIGS. 9A-9F demonstrate folding of the pentagonal fold pattern of the pouch of FIG. 8A, according to some exemplary embodiments of the invention.
Figures 9C, 9D:
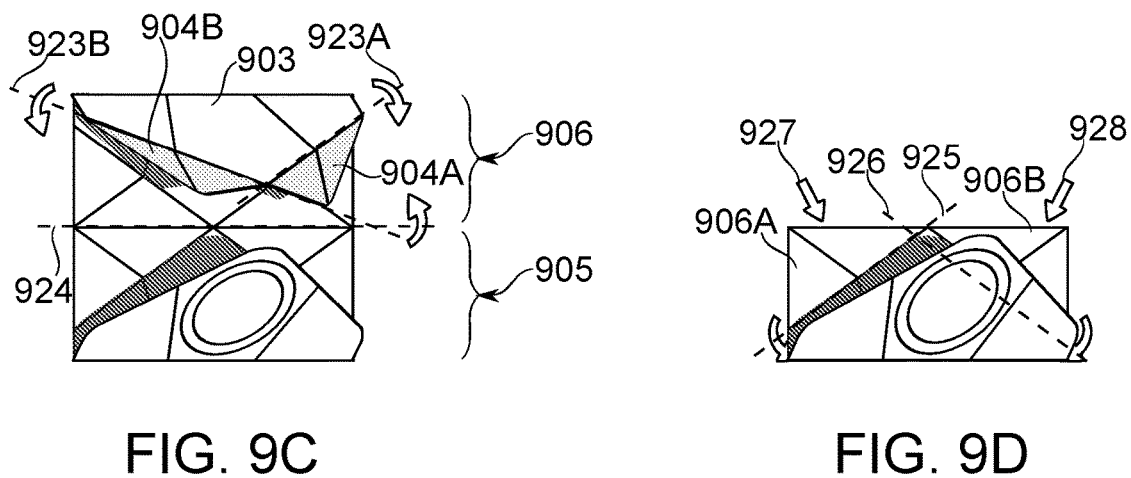
Figures 9E, 9F:
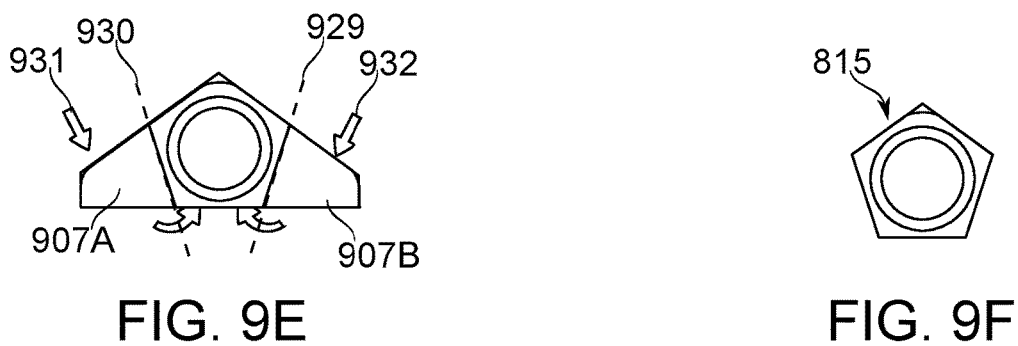

In some embodiments (FIG. 9A), a first fold for forming a pentagonal folded pouch package is made around axis 921, bringing region 902 behind and extending upward from region 901 to form the configuration of FIG. 9B. At FIG. 9B, region 903 is folded forward and down around axis 922 to overlie a portion of region 904. FIG. 9C illustrates three more folds—folds of corner regions 904A, 904B down around axes 923A, 923B, respectively; and the fold of region 906 downward and behind region 905 around axis 924. In some embodiments, these folds bring about the configuration of FIG. 9D.

In FIG. 9D, in some embodiments, corner regions 906A, 906B are tucked inward around axes 925 and 926, respectively, directly along the directions of arrows 927, 928. In some embodiments, further corner-region tucking (this time of corner regions 907A, 907B) is performed around axes 930, 929, beginning in directions 931, 932. The result, in some embodiments, is the pentagonal package shape for pouch 815 illustrated in FIG. 9F.

Figure 9G:
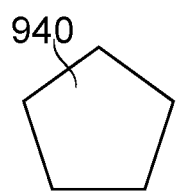
FIGS. 9G-9J illustrate variations on the pentagonal package folding pattern of FIGS. 9A-9F, according to some exemplary embodiments of the invention.

FIG. 9G illustrates a proximal-side view of the resulting package. Following the folding pattern described in relation to FIGS. 9A-9E, in some embodiments, yields a flat, smooth proximal surface 940 comprised of a single panel. Compared, for example, to the folding patterns of FIGS. 5A-5F, the folding pattern for a pentagonal pouch package potentially creates a self-locking property, where the pouch unfolds with relative difficulty (for example, due to the tucks of FIGS. 9D and 9E). This is a potential advantage, in some embodiments, in that the pouch, folded in the above-illustrated, or another way, achieves a self-restraining configuration. A self-restraining fold pattern potentially reduces a complexity and/or expense of manufacture by allowing removal or simplification of a separate pouch deployment restraint.

A self-locking property, in some embodiments, comprises a first fold which is restricted from opening (flattening across its crease) before a second fold opens sufficiently. This can occur, for example, with two folds having intersecting creases, where a second intersecting crease is folded after a first intersecting crease. In some embodiments, a first fold is self-locked because the non-zero forces acting in a direction to expand the fold are insufficient (in a direction of opening) to overcome forces acting in an opposing direction. Unlocking potentially occurs when the balance of forces shifts (for example, if a remote fold opens sufficiently to change a direction of pushing or pulling), and/or if a panel near a locked fold begins to warp, changing the dynamic force balance. During pouch deployment due to automatic release, the balance of forces is potentially affected by the ability of pressurized gas from within the stoma to reach and/or exert leverage from within one or more folded segments (panels) of the folded pouch. During manual deployment, the balance of forces is potentially affected by a main axis along which the user is pulling in order to release the pouch.

In some self-restraining pouch embodiments, tuning of the deployment pressure comprises changing the extent to which corners are "tucked in". For example, the corner regions 907A, 907B, in the embodiment shown, do not come fully to a point. If the pouch were made wider, the corner regions 907A, 907B would be longer, potentially providing greater self-locking stability. If the pouch were made narrower, the locking potential would be potentially decreased. A degree of self-locking, in some embodiments, also depends on a stiffness of the pouch material. In some embodiments, a range of pressure ranges within which deployment from self-restraint occurs corresponds to one of the ranges described hereinabove in relation to deployment upon removal of a separate pouch restraint, for example, in reference to FIGS. 1A-1B.

In some embodiments, opening force—for example, acting along an axis parallel to the top-bottom axis of the deployed pouch—may be transmitted along a transverse axis (for example, along the pouch width) by the configuration of the folding pattern. In particular, a folding pattern that comprises crease-lines which cross the force axis at an angle substantially other than 0° or 90° potentially transmits force transversely which acts to open up panels to the sides. The folding patterns of FIGS. 8A and 8C are potentially such folding patterns. A diamond-shaped folding pattern (potentially including triangular panels as well as quadrilateral panels) is another such pattern.

Figure 9H:
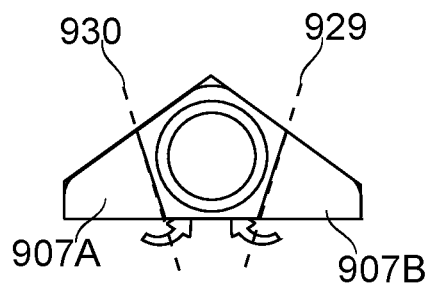
Figure 9I:
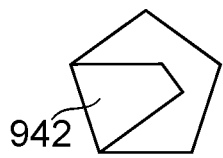
Figure 9J:
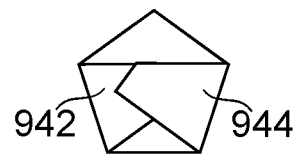

Reference is now made to FIGS. 9H-9J, which illustrate variations on the pentagonal package folding pattern of FIGS. 9A-9F, according to some exemplary embodiments of the invention.

In some embodiments, instead of tucking corners 907A, 907B in, one or both of the corners are folded back around axes 930, 929 (FIG. 9H). In some embodiments, one corner 942 is folded back around (for example, FIG. 9I). In some embodiments, two corners 942, 944 are folded back (FIG. 9J, for example). Other panels, in some embodiments, are also wrapped instead of being tucked. Potentially, wrap-around instead of tuck-in reduces self-restraint against deployment. These examples also demonstrate how variations of a basic pattern may be made for some different embodiments of the invention. For example, variations of the same basic ostomy appliance are, in some embodiments, tuned to different average self-deployment pressures by changing the specifics of the folding pattern used in manufacture.

Figure 9K:
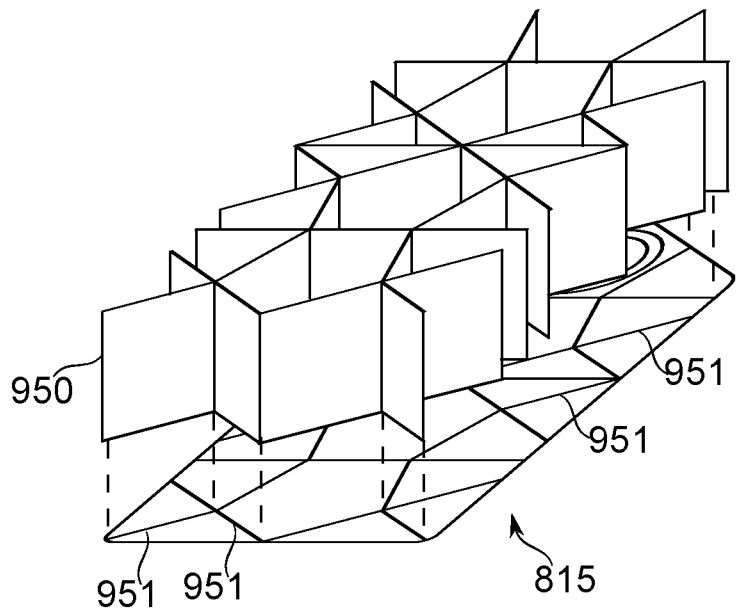
FIG. 9K illustrates a method of patterning a pouch for folding, according to some exemplary embodiments of the invention.

Reference is now made to FIG. 9K, which illustrates a method of patterning a pouch for folding, according to some exemplary embodiments of the invention.

In some embodiments, a patterning iron 950 is pressed to a pouch 815 in order to impress upon it indications 951 for following in folding the pouch into a collapsed package of predefined shape. In some embodiments, the indications are creases. In some embodiments, the patterning iron contains creasing surfaces corresponding to all creases for the pattern. In some embodiments, one iron is used on each side of the pouch. Optionally, one iron is used to impress folds which will bend in a first direction (relative to the plane of the unfolded pouch), and the other to impress folds which bend in the opposite direction. In some embodiments, the patterning comprises marks (such as by ink) which indicate fold directions. In some embodiments, the iron is pressed against the pouch material together with heat, which partially melts and/or deforms the pouch material. Potentially, this causes the material to assume a predetermined creasing pattern more markedly and/or more permanently. Potential advantages of this are easier, more rapid, and or more reproducible folding for packaging.

It should be understood that any of the folding patterns described herein, or otherwise indicated as being comprised in embodiments of the invention, may likewise be impressed upon the material of a pouch as an operation during manufacture. Similarly, a crease—such as creases 1113—used as a hinge or for another purpose, may be impressed upon pouch material using a patterning iron. The patterning iron may be fully shaped, as in the example 950, or it may be simple, for example, a single edge repeatedly applied. In some embodiments, pre-creasing is accomplished by another means, for example a laser, a tool drawn across the crease line, and/or a folding jig.

Figure 10A:
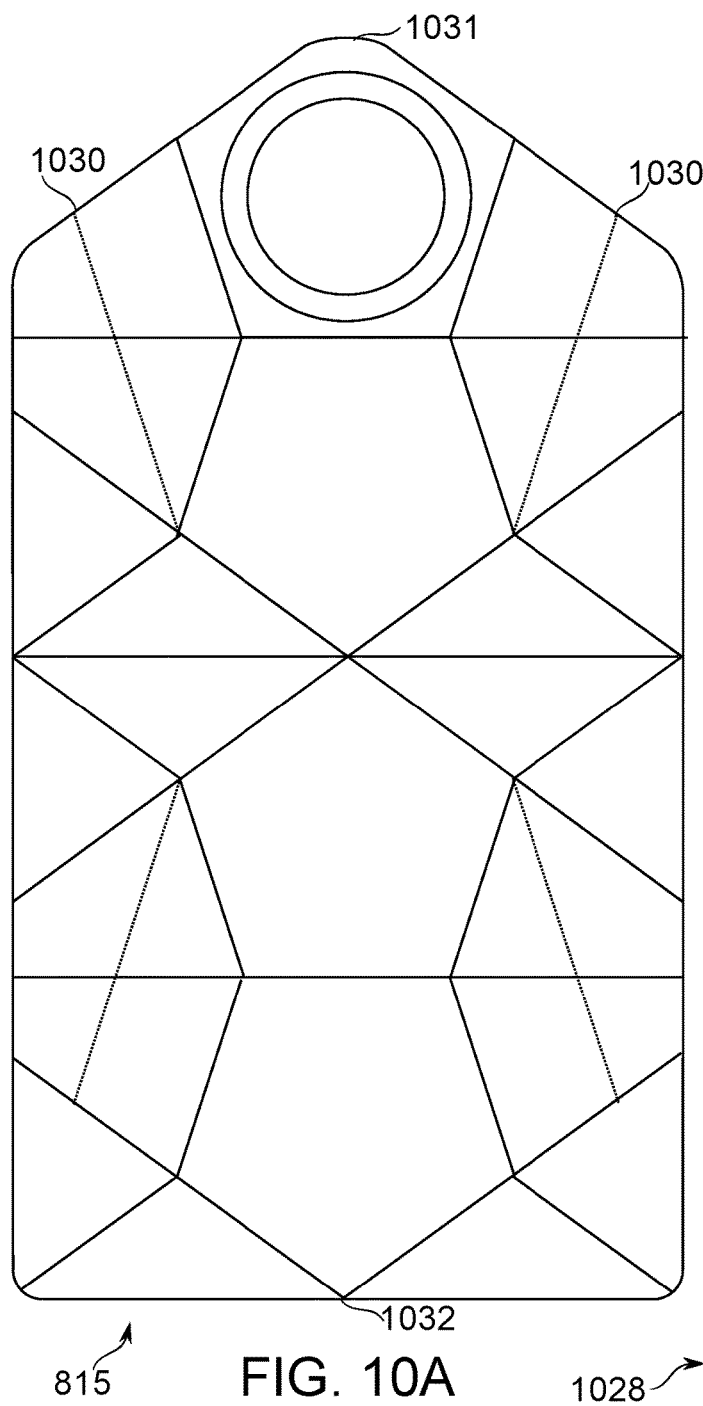
FIGS. 10A-10C illustrate the pentagonal folding pattern of a pouch and variations thereof, according to some exemplary embodiments of the invention.
Figure 10B:
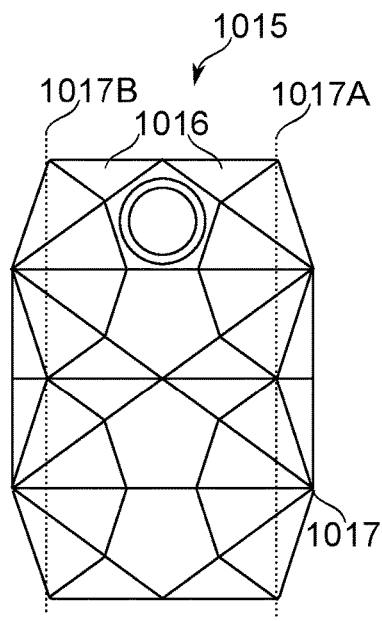
Figure 10C:
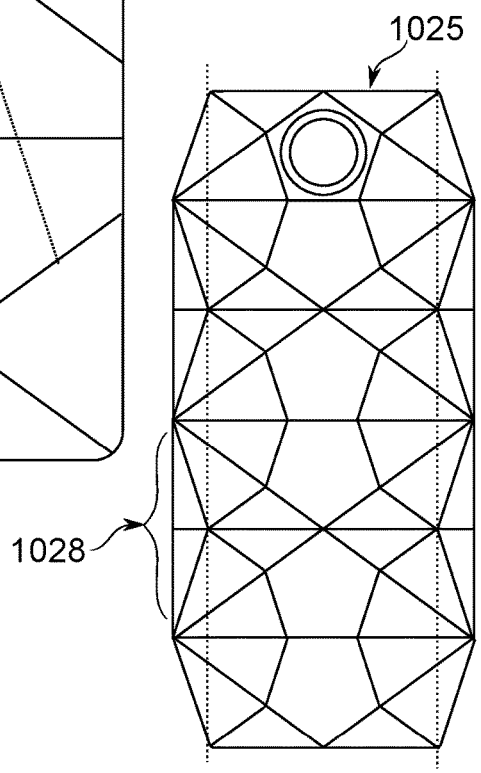

Reference is now made to FIGS. 10A-10C, which illustrate the pentagonal folding pattern of pouch 815 and variations thereof, according to some exemplary embodiments of the invention.

In some embodiments, FIG. 10A illustrates the pentagonal folding pattern which has been described hereinabove in relation, for example, to FIGS. 9A-9J. In some embodiments (FIG. 10B), the width of the pouch 1015 is extended beyond lines 1017A, 1017B (which represent the width of pouch 815). The fold lines are similarly extended, for example, to points such as vertex 1017. In some embodiments, top corners 1016 are added as well, potentially providing extra volume for receiving waste. In some embodiments (FIG. 10C), additional length is provided to pouch 1025 by adding the indicated panels 1028.

A potential advantage of adding additional panels is an increased volume for waste collection. In some embodiments, a self-locking pattern of folding is separately unlockable for different portions of the folded waste collection pouch. In some embodiments, this allows stages of pouch deployment. In a partial deployment stage, sufficient waste is received for fulfilling a need to evacuate, without the bag extending into view or otherwise becoming an intolerable burden. In a full deployment stage, the bag is further extended (for example, in privacy), to allow more convenient pouch handling and/or a fuller evacuation. As a potential advantage, a longer pouch may allow waste to drop further from a receiving aperture, reducing a risk of spilling. Additionally or alternatively, sufficient volume is extendable to allow sealing the pouch at a point above the waste mass, but proximal to the receiving aperture, as an operation during disposal.

It should be noted that some folds and/or crease lines create more potential risk of fatigue failure than others. For example, the multiple converging lines at vertex 1017 potentially weaken the pouch at this point. In some embodiments, such as pouch 815, it is a potential advantage to choose the pouch dimensions relative to the panel size such that creases potentially prone to material fatigue are reduced.

In some embodiments of the invention, one or more panels comprise a non-folded crease line created during manufacture, for example, crease-lines 1030. Potentially, lines 1030 act as break lines to redistribute forces during pouch deployment. For example, in some embodiments, manual pouch deployment which comprises a force acting to pull end region 1032 away from appliance-affixed region 1031 potentially experiences less self-interference if panels are creased to encourage temporary flexing around crease-lines 1030. With this modification, a potentially self-restraining fold pattern is convertible into a configuration which potentially opens fully both along its length and across its width by a single smooth downward pull.

For any general fold configuration, candidate locations which could potentially be freed from self-interference during deployment by this pre-creasing mechanism are identifiable by noting a tendency for a panel to buckle under opening forces, rather than open smoothly.

Figure 11A:
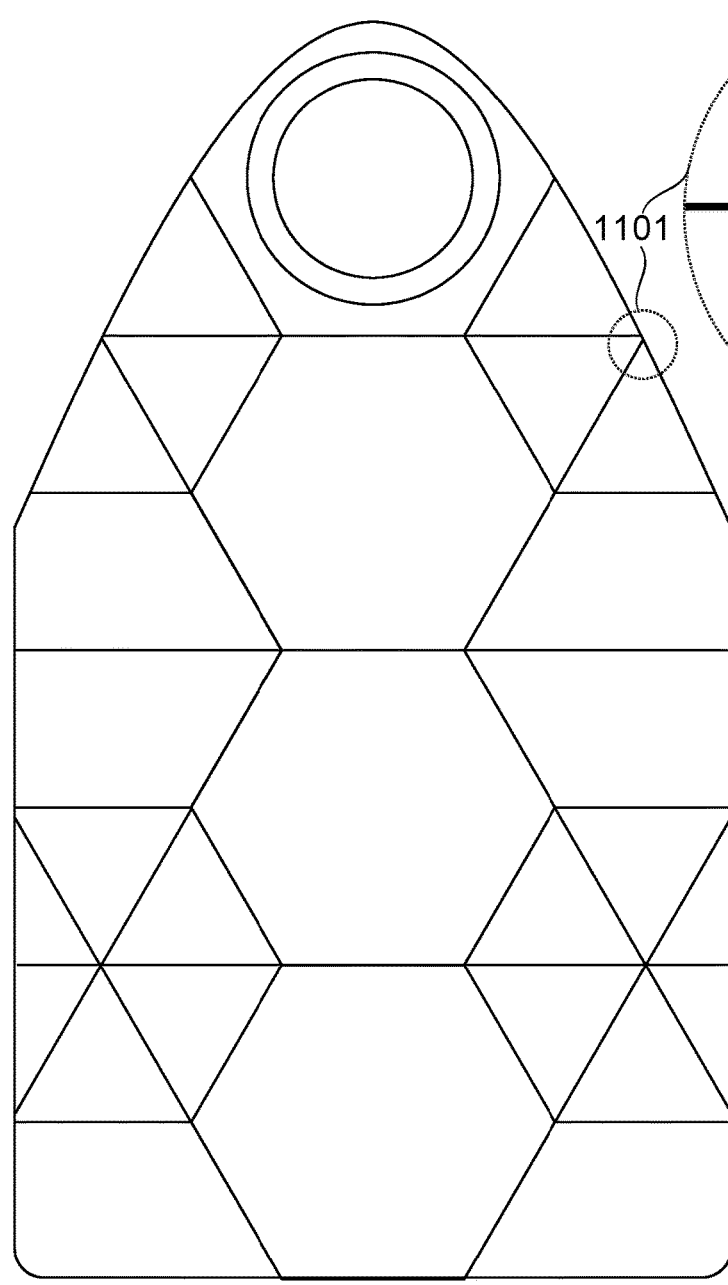
FIGS. 11A-11C illustrate the hexagonal folding pattern of a pouch and variations thereof, according to some exemplary embodiments of the invention.
Figure 11C:
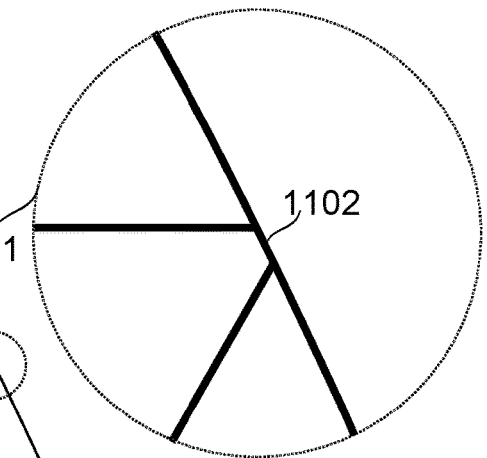
Figure 11B:
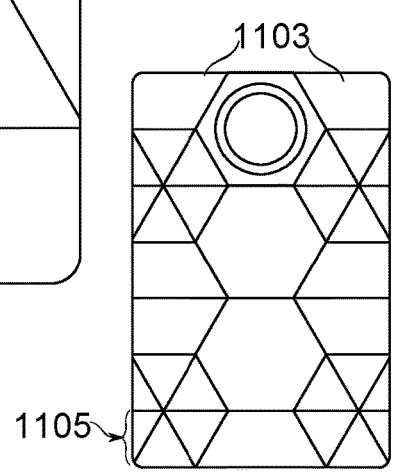

Reference is now made to FIGS. 11A-11C, which illustrate the hexagonal folding pattern of pouch 816, and variations thereof, according to some exemplary embodiments of the invention.

In some embodiments, FIG. 11A illustrates the hexagonal folding pattern which has been described hereinabove in relation, for example, to FIG. 8C. In some embodiments of the invention, as has been described in relation to FIGS. 10A-10C, the outer boundaries of pouch 816 are chosen in some places to avoid multiple converging crease points where possible, as shown at 1102 in magnified inset 1101. In some embodiments, FIG. 11B illustrates a variant of a hexagonally folded pouch package, comprising corners 1103 which are added relative to the shape of pouch 816. It is to be understood that, for some embodiments, properties such as self-restraining folding and folding pattern extendibility are also present, adjustable by one skilled in the art based on descriptions given herein. In some embodiments, an end panel region 1105 of a pouch comprises a truncated polygon, for example, a rectangle, partial pentagon, or partial hexagon, such that the proximal-most panel presents an end in a mid-region of the folded package, as shown and described, for example, in relation to FIG. 17.

Pouch-Holding Recesses

Figure 12A:
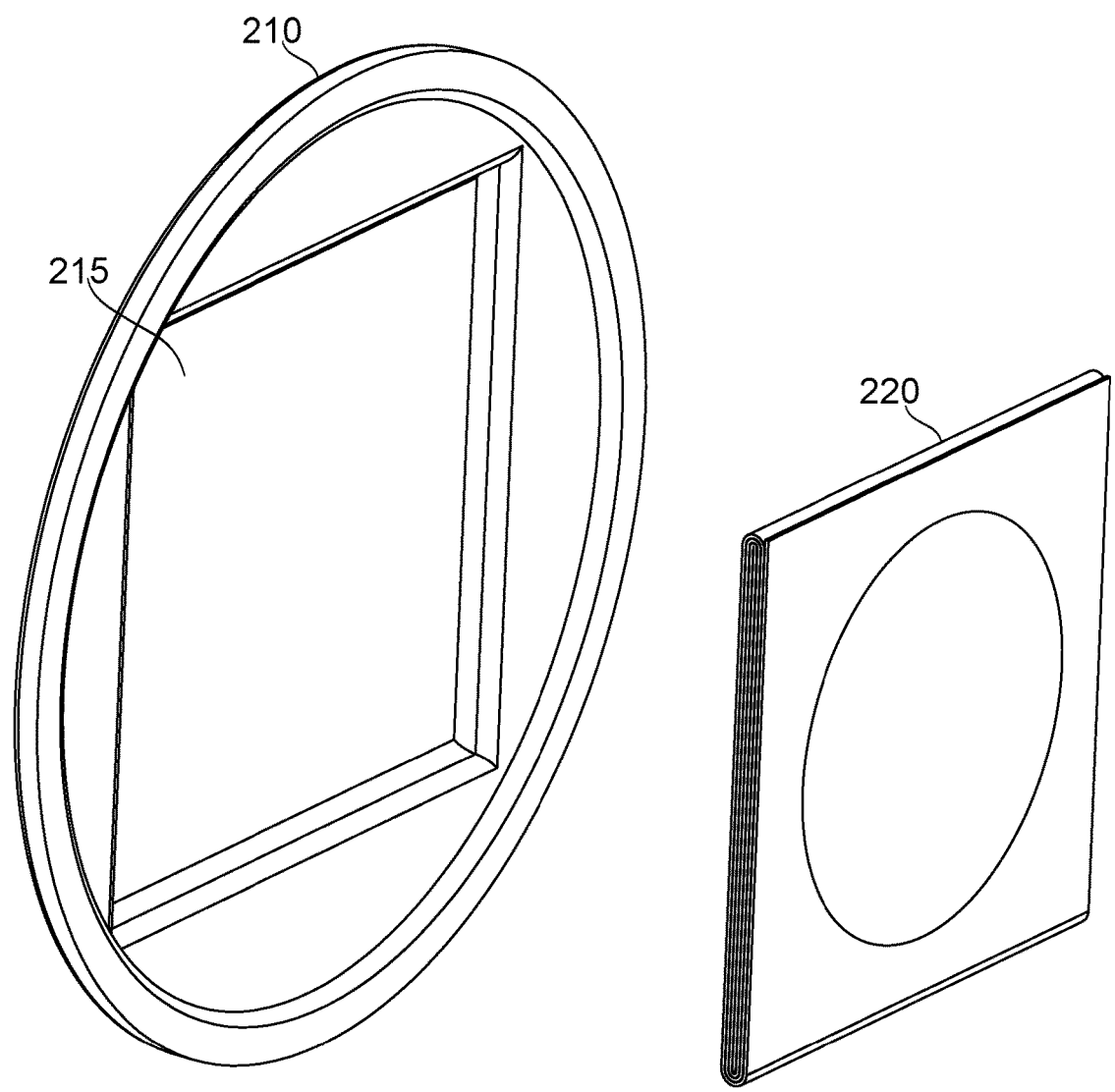
FIGS. 12A-12B illustrate an exploded view of pouch restraints comprising a cover having a recessed region for containing a flat-folded pouch, according to some exemplary embodiments of the invention.
Figure 12B:
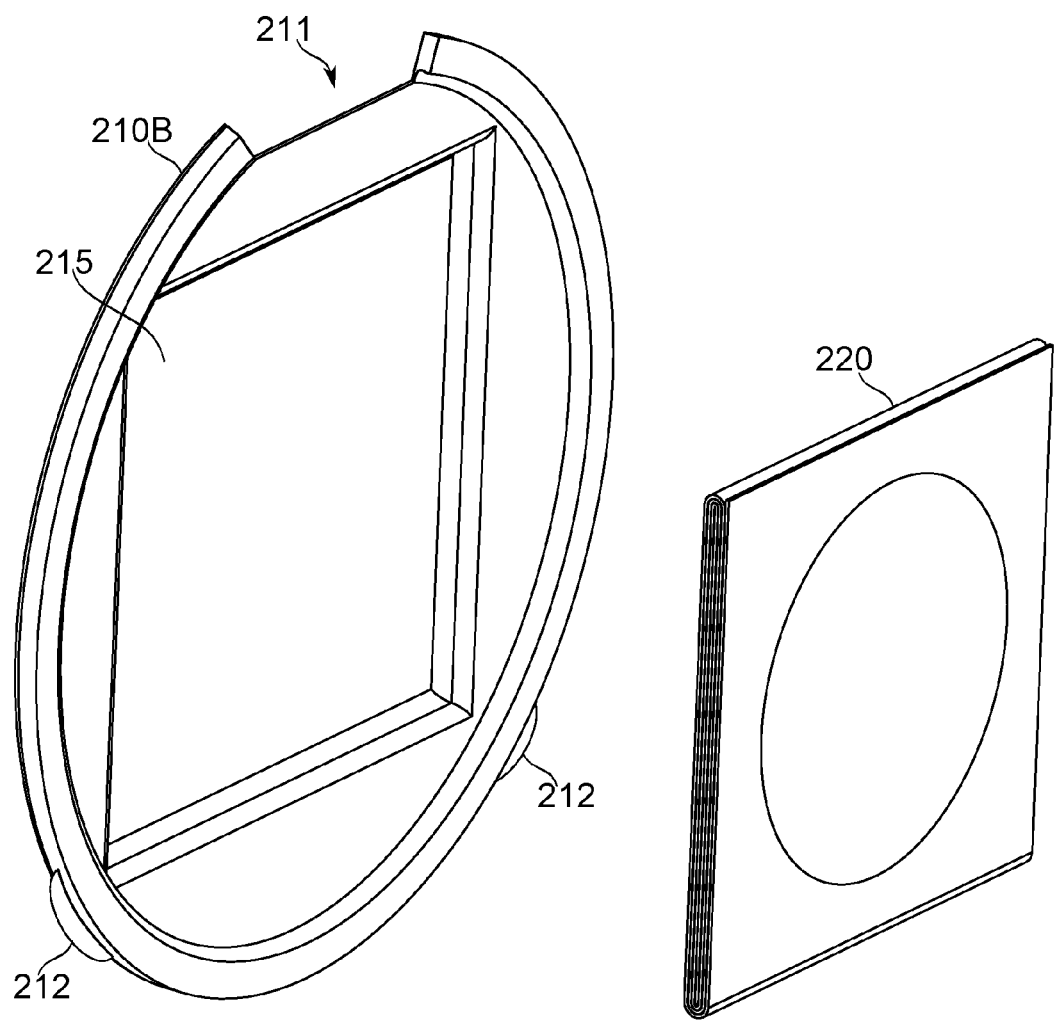
Figure 13:
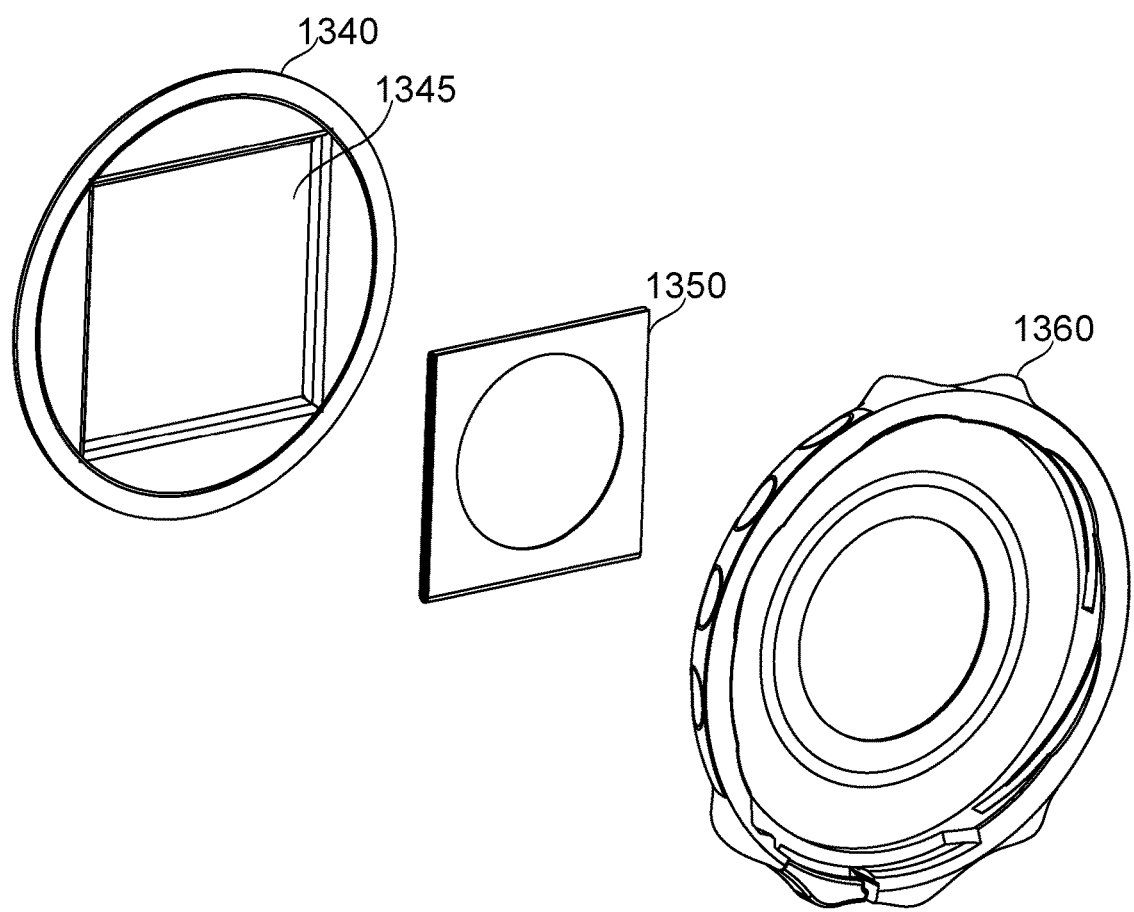
FIG. 13 illustrates an exploded view of a pouch restraint which comprises a cover having a recessed region for containing a flat-folded pouch, according to some exemplary embodiments of the invention.
Figure 14:
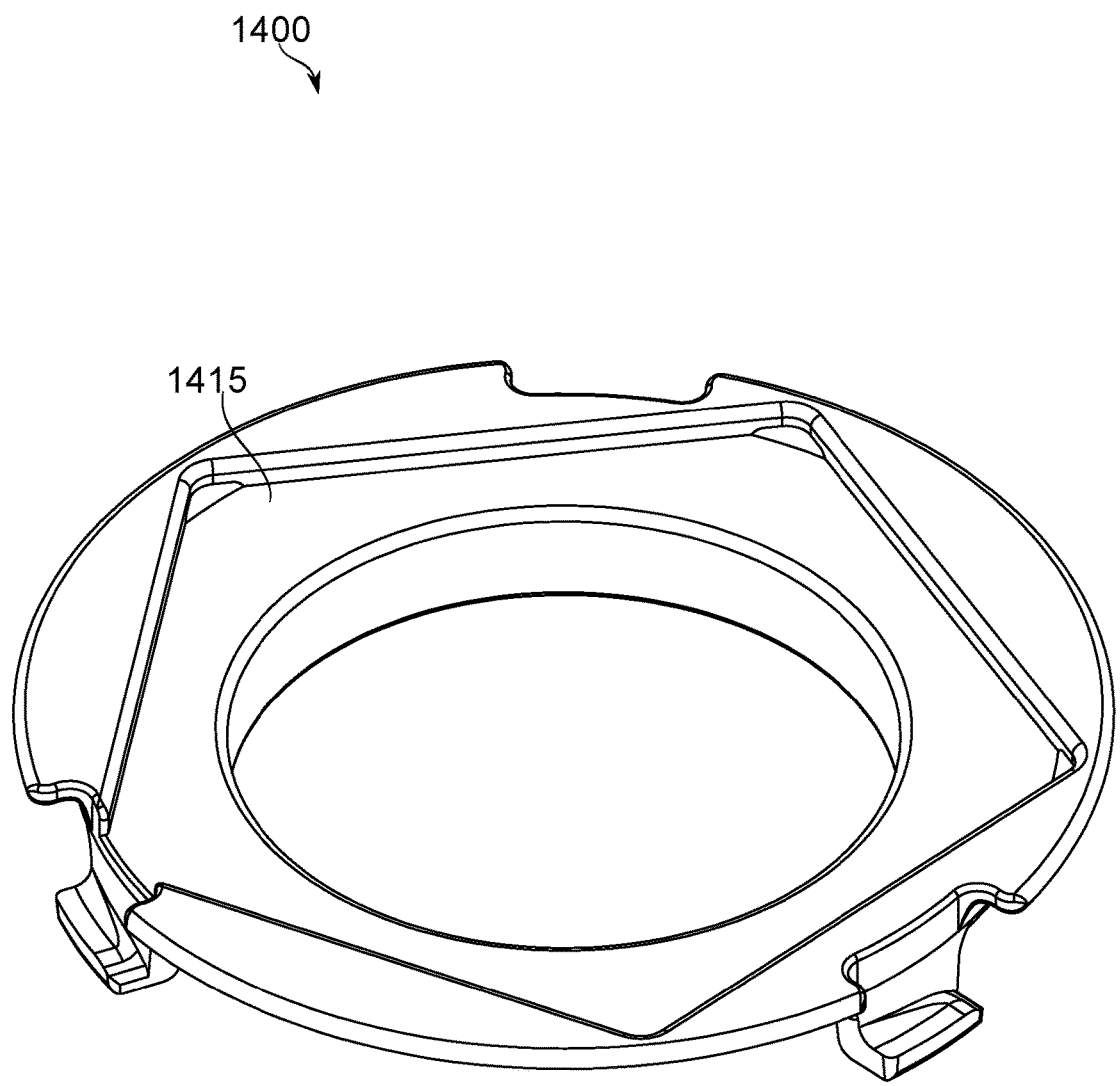
FIG. 14 illustrates an ostomy cap housing which comprises a pentagonal recess for holding a flat-folded pentagonal pouch, according to some exemplary embodiments of the invention.

Reference is now made to FIGS. 12A, 12B and 13, which each illustrate exploded views of a pouch restraint 210, 210B, 1340 which comprises a cover having a recessed region 215, 1345 for containing a flat-folded pouch 220, 1350, according to some exemplary embodiments of the invention. Reference is also made to FIG. 14, which illustrates an ostomy cap housing 400 which comprises a pentagonal recess 415 for holding a flat-folded pentagonal pouch, for example, as described in relation to FIGS. 9A-10C, according to some exemplary embodiments of the invention.

In some embodiments of the invention, a pouch restraint 210, 210B, 1340 is provided with a recessed region 215, 1345 sized to fittingly receive a portion of the bulk of a collapsed, flat-folded pouch 220, 1350. The recess provides a potential advantage for reducing an overall height of the ostomy appliance, for example, allowing more structurally substantial portions of a pouch restraint 210, 210B, 1340 to be positioned around the collapsed pouch 220, 1350, while a region extending over the pouch in region 215, 1345 is relatively thin. Potentially, the recess also allows the ostomy appliance to present a relatively flat surface appearance from a proximal-side view.

A potential advantage of a fitting containment and restraint of a flat-folded pouch is the maintenance of features which take advantage of functional aspects of a flat folded bag. For example, resistance to waste passage by creases in the bag is maintained, in some embodiments, such that fluid and/or solid waste pressing against the bag is prevented from freely entering its folded-over panel segments.

The pouch restraint of FIG. 12B additionally comprises a cutaway region 211. In some embodiments, a cutaway region 211 comprises a region of non- or reduced attachment to an ostomy cap or other ostomy appliance. This comprises a potential benefit for configuring deployment behaviors, for example as described in relation to FIG. 5Z hereinabove. Additionally or alternatively, the region allows for the escape of gasses which are released into the bag-holding chamber in some embodiments. Optionally, release is through a filter. In some embodiments, the filter is built into an ostomy pouch, for example as described in relation to FIGS. 21A-22D hereinbelow. In some embodiments, the filter is built into a housing of an ostomy cap or other appliance, with a vent leading to the bag housing chamber, but outside the bag itself.

In some embodiments of the invention, pry-tabs 212 are provided on the pouch restraint 210B (or any other pouch restraint). The pry-tabs 212 comprise protrusions which assist in the manual removal of a pouch restraint/cap cover/deployment prevention device. Optionally, they protrude far enough to be gripped. In some embodiments, the pry-tabs are shorter, but provide a purchase for a finger or implement to pluck at, and/or be wedged underneath. In some embodiments of the invention, pry tabs 212 comprise a long extension, adapted by its length and/or flexibility to be gripped in a fist, twisted around a finger, or otherwise grossly manipulated. This is a potential advantage for a patient with difficulties performing fine motor tasks. In some embodiments of the invention, pry tab 212 comprises one or more apertures, to which an extension such as a string is optionally attachable, in order to facilitate removal. In some embodiments, pry tab 212 comprises a rim which extends over a relatively large section of the device perimeter, for example, 20%, 40%, 50%, 90%, all the way around, and/or, any intermediate or smaller circumferential extent. In some embodiments, pry tab 212 comprises a flexible flap which lies flat against another surface of the device, configured to be picked away from the surface by prying, for example with a finger.

It should be noted in connection with FIG. 13 that a panel-folded pouch, in some embodiments of the invention, is attached to a housing other than a fixed housing, for example, rotatable housing 1360. Descriptions of functions associated with rotatable housing 1360 are described, for example, in International Patent Application No. IL2013/050401, by the Applicant, which is included herein by reference.

In FIG. 14, a pentagonal recess 1415 is shown in a cap body 1400, adapted to receive, for example, a pentagonally packaged pouch, such as pouch 815. Another difference between, for example, recessed region 1345 and recessed region 1415 is that the pouch is configured, in some embodiments to be held proximal to the recessed surface of recessed region 1415, while it is held distal to the recessed surface of region 1345. Optionally, the recess is deep enough to receive the entire thickness of the pouch package. Optionally, the recess receives a portion of the pouch packaged depth. Optionally, both proximal and distal recesses are provided (for example, one in a distal housing, and one in a proximal cover or cover-restraint). In some embodiments, the recess comprises a curvature, such that the pouch conforms to a non-planar shape approximately conforming to said curvature.

It is to be understood that the recess shape in general is adapted in some embodiments to the form of the collapsed pouch package which it contains. It is to be understood that the proximal or distal positioning of the pouch relative to the recess is adaptable for different recess shapes, depending on the components of the ostomy stack with which the pouch is provided.

Pouch Restraint Deployment Behavior

Reference is now made to FIGS. 12B-12F, which illustrate modes of deployment prevention element 210B detachment, according to some exemplary embodiments of the invention.

Figures 12C, 12D, 12E:
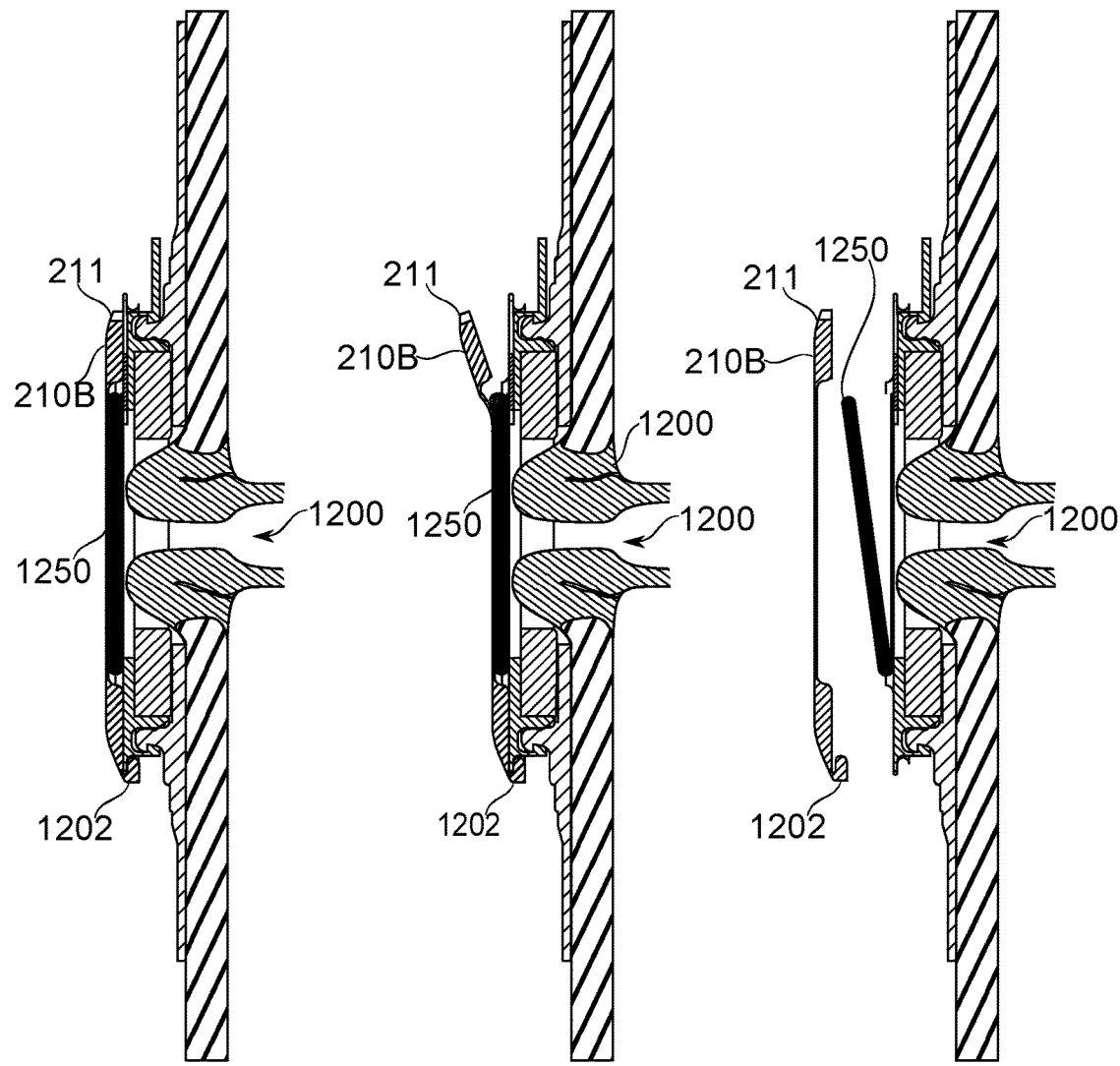
FIGS. 12C-12F illustrate modes of deployment prevention element detachment, according to some exemplary embodiments of the invention.

In some embodiments, a folded bag 1250 is positioned to cover a stoma 1200, and retained in place by a restraint 210B. In some embodiments, restraint 210B is a cap covering. In some embodiments, restraint 210B comprises a non- or reduced-attachment portion 211, and an attaching portion 1202. In some embodiments, more than two attachment strengths are provided, for example, three or more discreet attachment strengths, and/or graded attachment strengths. In some embodiments of the invention, the detachment behavior of restraint 210B as a function of time and/or pressure is affected by its configuration relative to pouch 1250. FIG. 12C represents a fully attached state of restraint 210B. In FIG. 12D, pouch 1250 is slightly distended, for example, due to accumulated flatus pressure. In some embodiments, the distension acts to pry non-attached portion 210 away from the stomal appliance, optionally producing a "peeling" behavior. As pressure increases, so does detachment, until, at FIG. 12E, detachment is complete. From this point, full pouch deployment proceeds without limitation by restraint 210B. In FIG. 12E, pouch 1250 is shown as having a free end which is oriented to non-attached region 211. It is to be understood however, that other features of a pouch configuration potentially affect and/or direct pressure to a non-attached region 211, and that the depicted free end orientation is a visual indicator of any such feature.

Figure 12F:
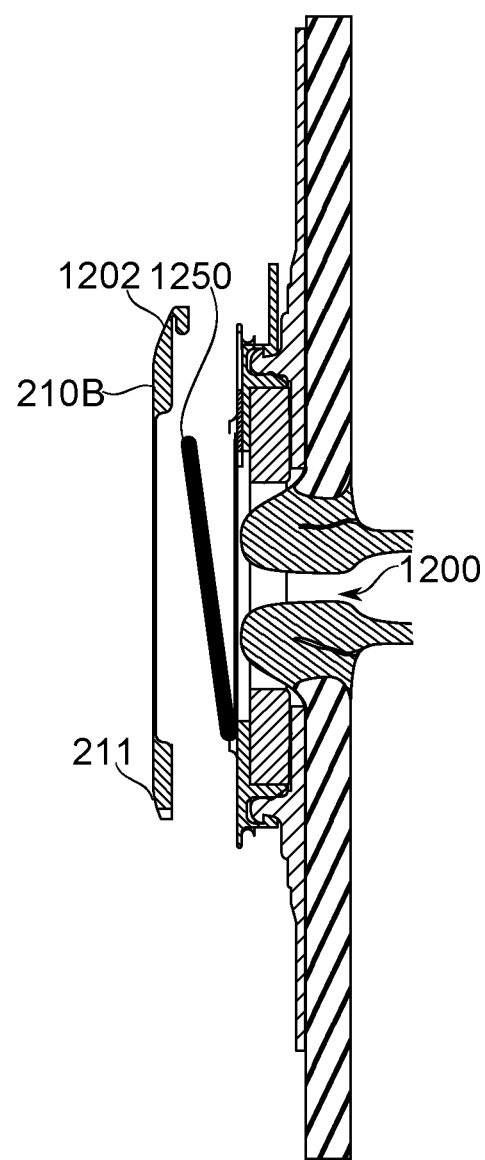

In FIG. 12F, restraint 210B is shown inverted relative to pouch 1250. In some embodiments of the invention, deployment behavior is regulated by choosing an orientation of a restraint relative to a pouch. Optionally, the pouch configuration is also selectable.

In some embodiments, putting a well-attached region 1202 near the "free end" (pressure point) of pouch 1250 changes the deployment characteristics of the device. The configuration of FIG. 12F, for example, optionally produces a "pop" behavior, wherein pressure is directed against the most securely attached region until it increase enough to force detachment. After that, in some embodiments, no remaining region of attachment is strong enough to resist further detachment. According to details of the embodiment, the changes comprise one or more of the following: (1) higher or lower full release pressure, (2) larger or narrower range of full release pressures, (3) higher or lower first-detachment pressure, and/or (4) larger or narrower range of time and/or pressures between first-detachment, and full release.

Pouch Restraints

Figure 15:
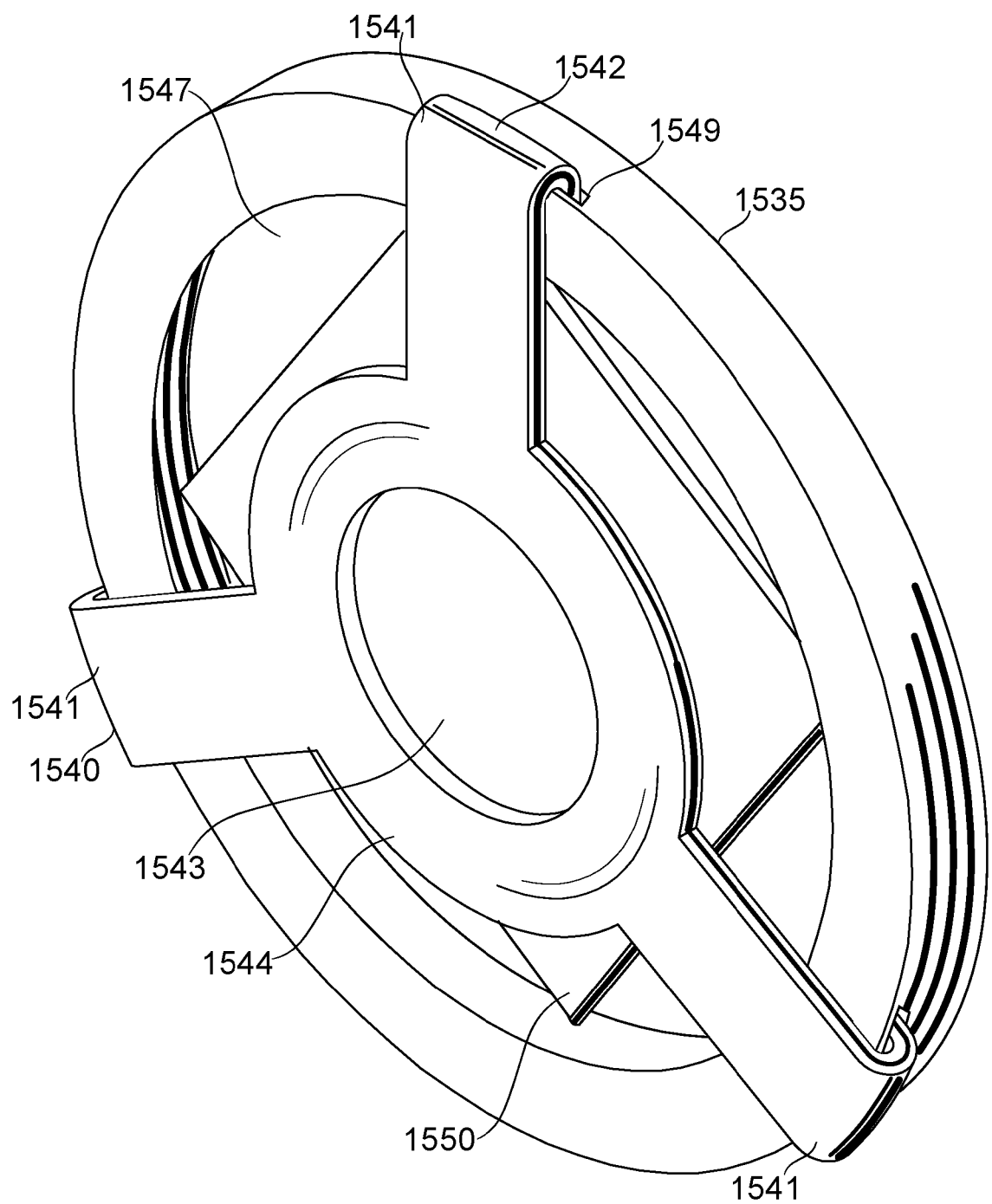
FIG. 15 illustrates an apertured, pouch-spanning pouch restraint, according to some exemplary embodiments of the invention.

Reference is now made to FIG. 15, which illustrates an apertured, pouch-spanning pouch restraint, according to some exemplary embodiments of the invention.

In some embodiments of the invention, a pouch restraint 1540 comprises one or more apertures 1543, 1547, through which a collapsed pouch 1550 is potentially viewable and/or touchable. In some embodiments, an ostomy component housing 1535 (which is, for example, of an adaptor, cap, or wafer) is provided with attachment structures 1542 which receive mating attachment structures 1549 of the restraint. The pouch restraint 1540 may be provided with a variable number of attachment structures, which are optionally held, for example, on two, three, four or more arms 1541. Optionally, the arms are joined to each other by a base structure 1544, which may comprise a ring, disk, polygon, or other shape. In some embodiments, a central aperture 1543 is provided. In some embodiments, pouch restraint 1540 is released above a predetermined pressure or range of pressures, for example as described in relation to FIGS. 1A-1B. In some embodiments, pressure-triggered release forces are communicated to the restraint by pressure from the pouch 1550 upon the pouch restraint 1540.

It is a potential advantage for the pouch restraint to comprise an aperture, for example, such that the material of the pouch is available to directly provide an indication of internal pressure by viewing of a degree of distension, and/or by touching to sense a degree of tautness.

The restraint attachment structures 1549 and/or housing attachment structures 1542 are optionally set with variable depths, such that different orientations of the restraint 1540 result in different deployment behaviors, for example as described hereinabove. For example, an attachment structure 1549 is configured to extend further into (or less-far into) a mating structure 1542 by, for example, 0.25 mm, 0.5 mm, 1 mm, or another larger, smaller, or intermediate extent. Additionally or alternatively, an ostomy appliance housing attachment structure is configured to have a depth which is less than the depth of another such attachment structure by, for example, 0.25 m, 0.5 mm, 1 mm, or another larger, smaller, or intermediate extent. In some embodiments, the difference in depth is sufficient to at least partially exclude an attachment structure 1549 from fully engaging into position, weakening the attachment thereof.

Figure 16:
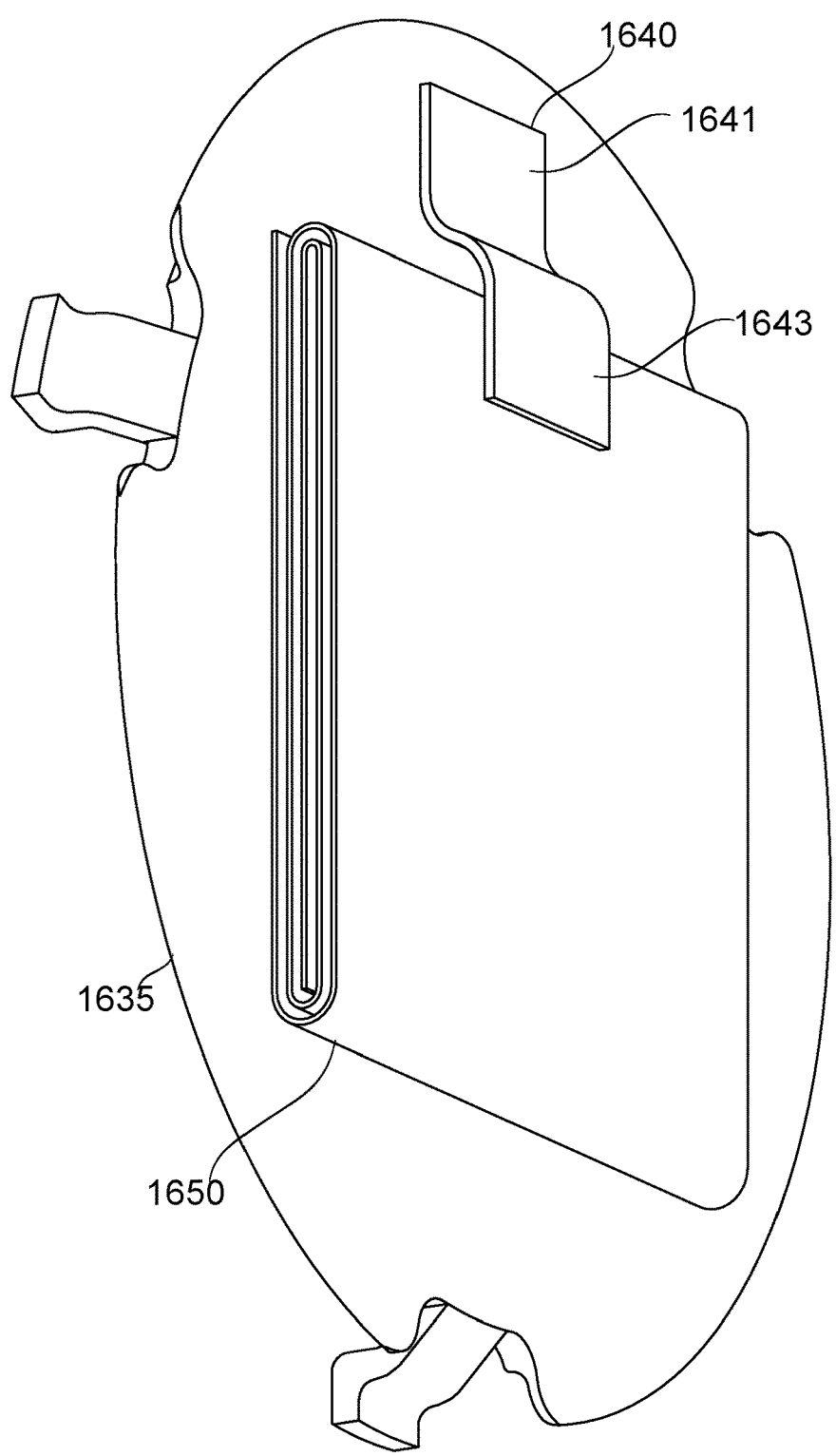
FIG. 16 illustrates a pouch restraint comprising an extended member spanning a plurality of attachment regions, according to some exemplary embodiments of the invention.

Reference is now made to FIG. 16, which illustrates a pouch restraint comprising an extended member 1640 spanning a plurality of attachment regions, according to some exemplary embodiments of the invention.

In some embodiments, a restraint for a pouch 1650 comprises an extended member 1640 which spans a plurality of regions of attachment 1641, 1642. In some embodiments, pouch restraint 1640 comprises a strap. In some embodiments, restraint 1640 comprises a region of attachment 1643 to the pouch material. In some embodiments, restraint 1640 comprises a region of attachment 1641 to an ostomy component housing 1635 (which is, for example, of an adaptor, cap or wafer). In some embodiments, attachment is between regions of the pouch material (for example, between a proximal end of the pouch, and a distal region of the pouch which is more directly affixed to an ostomy component housing). In some embodiments, attachment is between regions of an adaptor housing 1635 or other ostomy component, and the restraint extends over pouch 1650 to restrain it.

In some embodiments, restraint 1640 comprises attachment which is configured to release above a predetermined pressure threshold, for example as described in relation to FIGS. 1A-1B hereinabove. In some embodiments, release allows complete deployment of the pouch 1650. In some embodiments, the ostomy appliance comprises a second, partial restraint, such that a first stage of pouch deployment is potentially followed by a second deployment stage, for example as described hereinabove in relation to FIG. 10C.

In some embodiments, pouch restraint 1640 comprises a strip of polymer plastic, fabric, an extended member such as a string, or another member which spans between two regions of attachment. In some embodiments, pouch restraint 1640 is attached by an adhesive. Optionally, the adhesive comprises an adhesive backing. In some embodiments of the invention, attachment to one or both regions of attachment is by weld-bonding, for example using heat, laser, ultrasound, pressure, and/or another source of welding energy.

In some embodiments of the invention, two of the regions of attachment of pouch restraint 1640 are located within 3-5 mm of each other. In some embodiments, the distance between attachment regions is 0-1 mm, 0.5-3 mm, 2-5 mm, 4-8 mm, 5-10 mm, 8-20 mm, 10-40 mm, or another narrower, broader, or equivalent-breadth range of lengths ranging between the same, intermediate, shorter or longer lengths.

Figure 17:
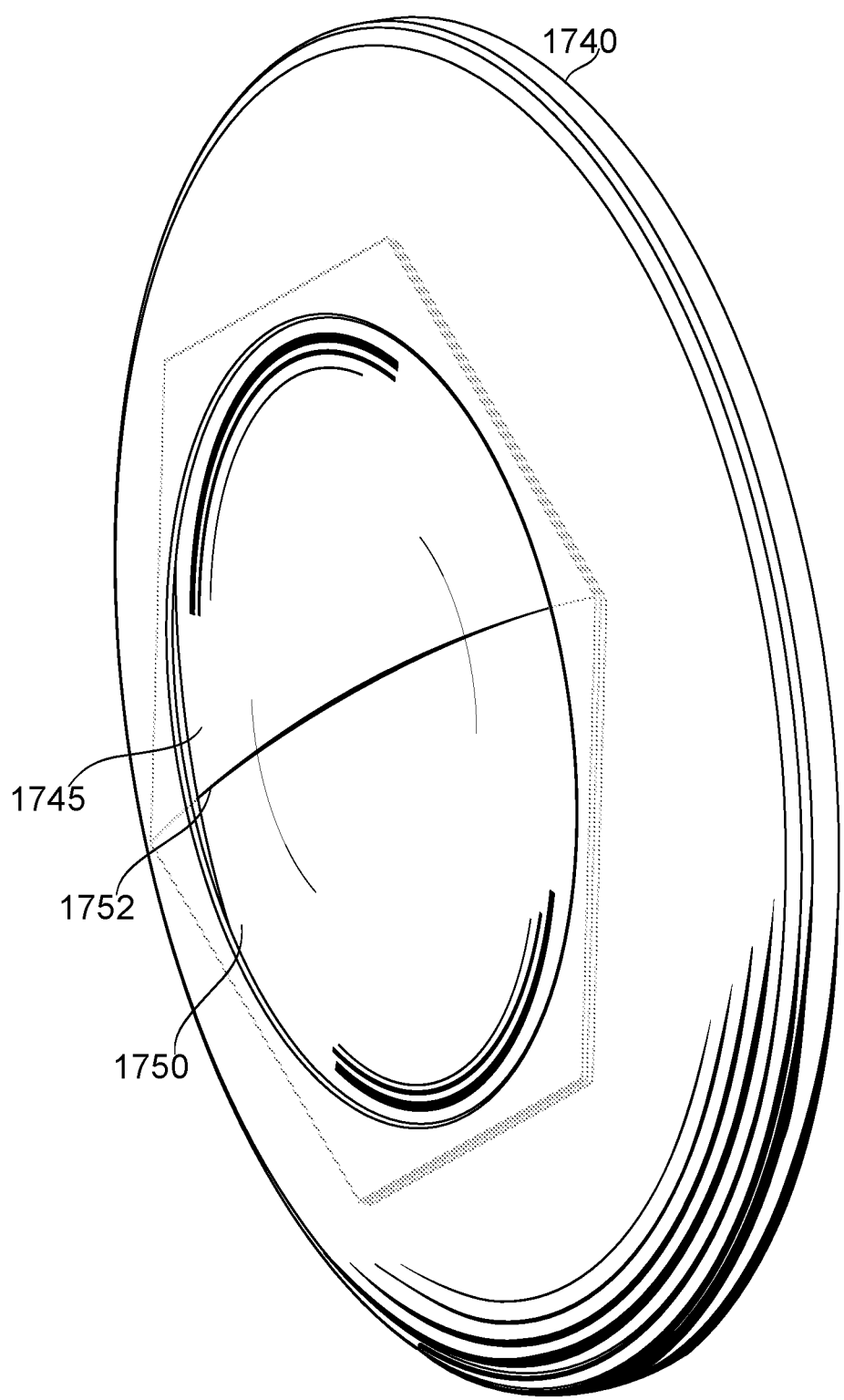
FIG. 17 illustrates a pouch restraint comprising a central aperture through which a pouch is viewable and/or touchable, according to some exemplary embodiments of the invention.

Reference is now made to FIG. 17, which illustrates a pouch restraint 1740 comprising a central aperture 1745 through which a pouch 1750 is viewable and/or touchable, according to some exemplary embodiments of the invention.

In some embodiments, restraint of pouch 1750 is by a restraint 1740 which comprises a circumferential ring with a central aperture 1745 over a region of the pouch. In some embodiments, the pouch restraint 1740 is configured to release from its edges under a predetermined pressure from within an ostomy appliance, for example as described in relation to FIGS. 1A-1B. In some embodiments, the aperture is sized so that such a sufficient predetermined pressure causes the pouch 1750 to deploy through aperture 1745. Optionally, determination of the predetermined pressure comprises setting a diameter for aperture 1745, such that a smaller diameter holds to a higher pressure than a wider diameter.

It is a potential advantage of apertured restraint 1740 to allow pouch 1750 to be sensed (viewed/touched) as an indication of the pressure behind it, according to a degree of distension and/or tautness.

In some embodiments of the invention, the folding pattern of pouch 1750 provides an end region 1752 which can be gripped by inserting a finger underneath it. Potentially, this allows manual deployment of the pouch without a previous step to release a pouch restraint. The folding pattern, in some embodiments, comprises a partially-covering last panel region, for example as described in relation to FIG. 11B hereinabove. It should be understood that the pouch package is not limited to a hexagon, as shown in FIG. 17; it may be another shape described herein, and/or selectable by one skilled in the art based on the descriptions herein.

Pleated Folds

Figure 18A:
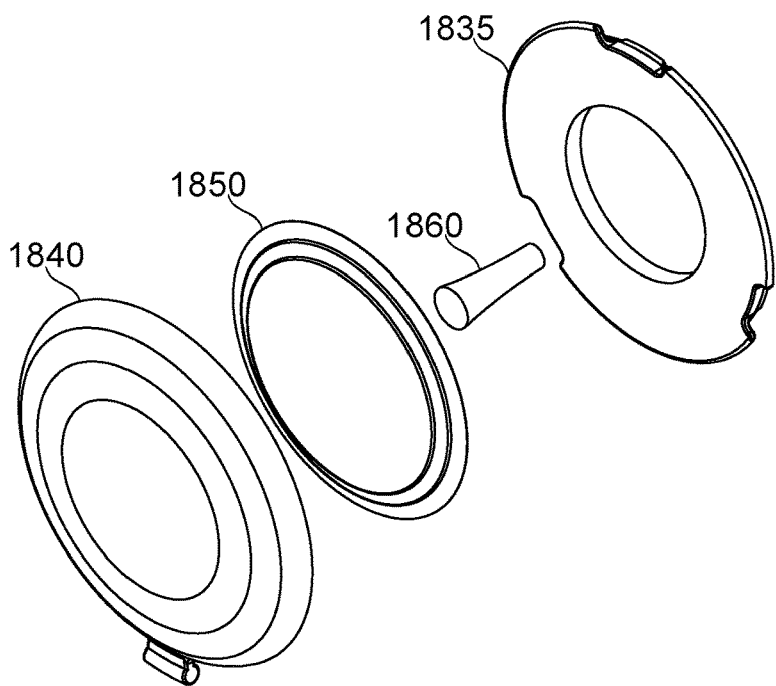
FIGS. 18A-18C illustrate a pleated pouch comprising a stomal plug insert, according to some exemplary embodiments of the invention.
Figures 18B, 18C:
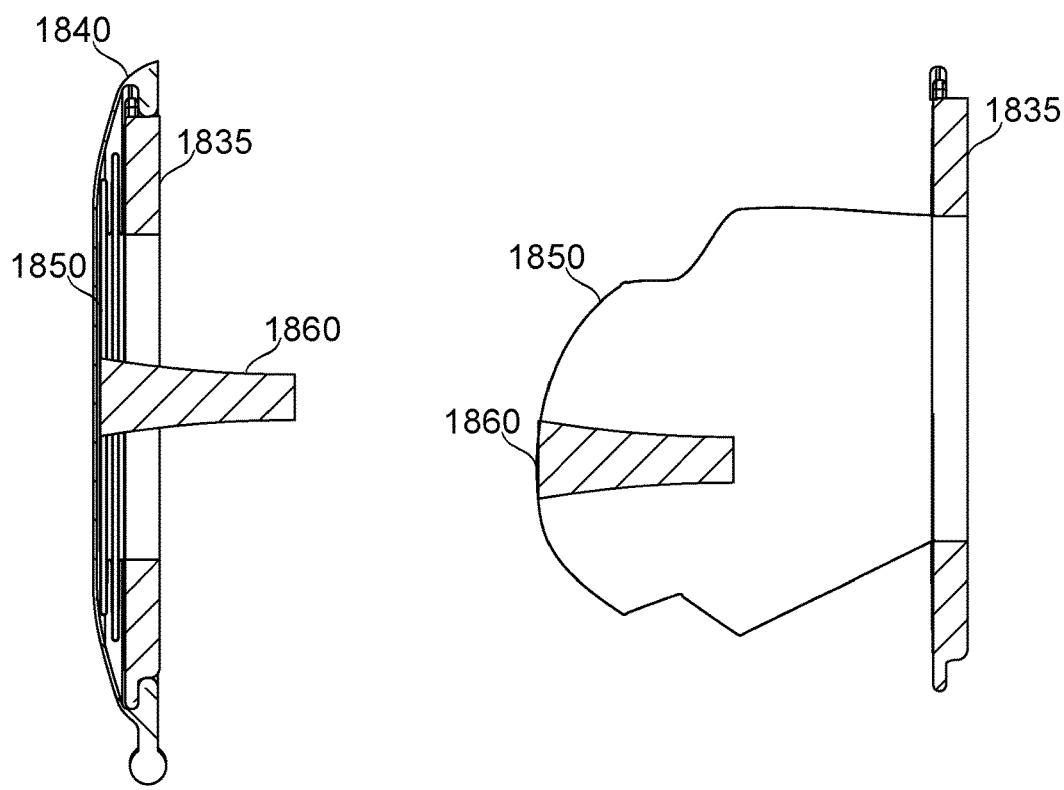

Reference is now made to FIGS. 18A-18C, which illustrate a pleated pouch comprising a stomal plug insert, according to some exemplary embodiments of the invention.

In some embodiments, the pouch material comprises a pleated pouch wall. In some embodiments, pouch material is formed to assume a pleated collapsed configuration 1850, for example, a series of concentric folds or another pleated shape. This configuration, in some embodiments, is attached to an ostomy appliance housing 1835. In some embodiments, the pouch is restrained from deployment by a pouch restraint 1840 which may be a cover or another pouch restraint as described hereinabove.

Figure 19A:
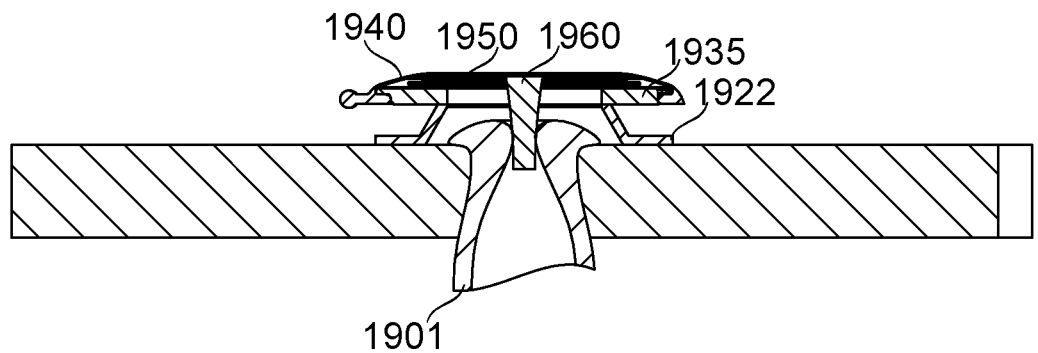
FIGS. 19A-19B illustrate alternative embodiments of an ostomy appliance comprising a pleated pouch and an inserting stomal plug according to some exemplary embodiments of the invention.

In some embodiments, the pouch 1850 is attached to a plug 1860, which is insertable in its folded configuration into a stoma, for example as illustrated in the exploded schematic view of FIG. 19A. FIG. 18B shows an exemplary configuration when the pouch is still restrained in a collapsed configuration. After release, the expanding pouch, in some embodiments, brings the plug 1860 with it.

Use of a plug provides a potential advantage for reducing the inflow of stomal waste during a deployment-restrained phase of stomal appliance wear. In some embodiments, the plug is made of a soft and/or absorbent material, such as cotton or a polymer foam. Stomal plugs configurable for use with the collapsed pouch shown here are described also in U.S. patent application Ser. No. 13/890,433 by the Applicant, which is included herein by reference.

Figure 19B:
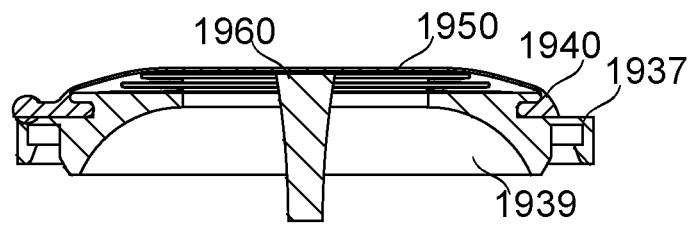
Figure 19B:
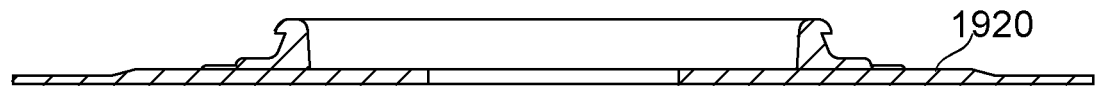

Reference is now made to FIGS. 19A-19B, which illustrate alternative embodiments of an ostomy appliance comprising a pleated pouch 1950 and an inserting stomal plug 1960, according to some exemplary embodiments of the invention.

In some embodiments, stomal plug 1960 is attached to collapsed pouch 1850, and configured to be held, when pouch 1950 is collapsed, such that inserts into a stoma 1901. Removing pouch restraint 1940 allows pouch 1950 to expand, as described, for example, in relation to FIG. 18C. In some embodiments, a relatively thin cap and/or adaptor 1935 is mountable above a stoma at a distance determined largely by the height of a mating ostomy wafer 1922 (for example, as in the schematic view of FIG. 19A). In some embodiments, a cap and/or adaptor comprise a deeper depression 1939 which is held in place over a low-rising ostomy wafer 1920 (for example, as in the partially-exploded schematic view of FIG. 19B).

Box-Pleating

Reference is now made to FIGS. 20A-20D, which illustrate a box-pleated ostomy pouch, according to some exemplary embodiments of the invention.

In some embodiments, a potentially greater proximal-distal extent is provided to a folded ostomy pouch by using box pleats to give it additional depth. FIG. 20A illustrates a one-piece folding pattern for an exemplary box-pleated pouch 2000, which in some embodiments folds to form a 1:5 (width:length) pouch. The resulting pouch potentially has a smaller carrying capacity than other embodiments described herein, although it may be made wider, deeper, and/or longer, as necessary. The long, thin configuration (seen from the front in FIG. 20B and from the side in FIG. 20C) has a potential advantage in approximating an artificial external rectum.

In the assembled configuration of the pouch, ends are brought together and sealed (for example, along the column of small "x" marks at 2010A to the column of dot marks 2010B). Sealing is, for example by adhesive, welding, and/or a clamp. Although a clamp potentially interferes with full packaging of the appliance, it potentially allows draining of waste from pouch end 2002, and then resealing pouch 2000. In some embodiments, initial sealing is by welding or adhesion, such that an ostomate can open the end by cutting, tearing and/or pulling at the pouch end 2002. After evacuation, an ostomate, optionally, can continue to wear the pouch in a relatively expanded condition by re-sealing the end with a clamp or by another re-sealing means. Optionally, it is sufficient to simply re-fold and re-package the pouch, the convolutions of the folding being adequate to prevent leakage for a period (though potentially not adequate to withstand leakage during a safety-enforced automatic deployment event).

Potentially, this allows an ostomate to delay exchanging ostomy appliance components until a more convenient time and/or place. Potentially, this provides an advantage by reducing the amount of medical waste which the ostomate must manage at the time of an evacuation event.

Sealing is also made in some embodiments at the large "x" marks 2011A in rows at right, matching to corresponding dots 2011B in rows at left, marks 2012A matching to dots 2012B.

In some embodiments, the pouch is initially fully collapsed, including collapsing the pleats along the length of the pouch, and then panel folding again to create a shorter package, as in FIG. 20D, and/or corresponding to the top square region in FIG. 20B, containing the pouch inlet aperture 2050 (FIG. 20B shows dotted lines for some hidden fold-panel boundaries, and dashed lines for inlet aperture 2050 and stomal plug 2060). Upon deployment, the pouch is optionally removable, and/or openable at end 2002 for the discharge of waste. In some embodiments corresponding to FIGS. 20A-20D, the pouch end 2002 is directable by an ostomate to empty into a sewage receptacle such as a toilet.

In some embodiments, one or both of manual and automatic deployment are possible (previous restraint and automatic release being based, for example, on restraint mechanisms described herein, or another mechanism). Deployment, however, is not necessarily sufficient to contain all waste that is ready to be discharged. Automatic deployment potentially releases enough built-up pressure to relieve an unsafe pressure condition, and alert an ostomate that waste discharge is urgently required. However, the pouch is potentially relatively unobtrusive and non-burdensome, even when deployed.

In some embodiments of the invention, the pouch further comprises a stomal plug 2060. Mark 2062 on the folding template of FIG. 20A indicates an optional point of attachment on for a stomal plug. Compared to some embodiments of a flat two-ply pouch, the box-pleated shape of the pouch is potentially advantageous for use with a stomal plug by allowing a larger proximal distance of expansion, which withdraws the plug fully from the stoma. Potentially, the well-defined folding pattern of the pouch allows the plug to be easily replaced after evacuation, in cases where the ostomate decides to continue wear until a more convenient time for replacement.

It is to be understood that a tubular, down-hanging pouch may be realized in other ways, including folded-sheet and non-folded sheet configurations. For example, a simple tube, with suitably arranged closures and apertures, is potentially deployable as an artificial external rectum. Potential advantages of a box-pleated pouch over a simple collapsed tube include a naturally downward-directed exit aperture, large but collapsible proximal clearance near the pouch entry aperture, and/or a readiness to be easily reset to a packaged condition after an evacuation event for a period of further wear.

Pouch-Attached Filter Elements

Reference is now made to FIG. 21A, which schematically shows a filter element 2103 positioned to vent through the material of an ostomy pouch 2100, according to some exemplary embodiments of the invention.

In some embodiments, a filter element 2013 is attached to an ostomy pouch 2100, at a position selected to allow ventilation therethrough even when the pouch is folded into a collapsed configuration. In some embodiments, a ventilation outlet 2105 comprises one or more slits in the pouch material, over which the filter element 2013 is sealed. In some embodiments, the position is defined by one or more of the following: (1) a side of the pouch toward or away from an ostomate, (2) the choice of a particular sub-panel 2108, and/or, more particularly, choice of a pouch sub-panel 2108 in relation to the sub-panel comprising an inlet aperture to the pouch 2101, and/or (3) a particular position and/or orientation within the selected sub-panel.

Reference is now made to FIG. 21B, which schematically shows structural detail of a filter element 2103, according to some exemplary embodiments of the invention.

In some embodiments, a filter element 2103 comprises fixed attachment to a portion of an ostomy pouch, for example, a sub-panel 2108. In some embodiments, attachment is to the inside of the pouch. Optionally, attachment is outside, in which case the "vent" and "inlet" portions of the filter are reversed relative to the rest of the discussion. In some embodiments, one or more surfaces of the filter body 2102 are sealed against the entry of gas by a sealing element 2104. In some embodiments, gas enters only through one or more defined inlet regions 2107. In some embodiments, gas exits through one or more outlets 2105. In some embodiments, the shortest distance between any given inlet 2107 and any given outlet 2105 is configured to ensure a desired level of odor clearance by the material of filter body 2102.

In some embodiments, the body 2102 of filter 2103 is of a construction such as felt, cloth, foam, lattice, or cake. In some embodiments, the body 2102 of gas filter 2013 comprises an odor-absorbing material which filters odorants from outflowing gasses. Potentially, filtered odorants are noxious odorants, for example, fecal odors. According to the embodiment, odor absorption is, for example, by the use of activated charcoal, silica gel, zeolites, and/or carbide-derived carbon. In some embodiments, the filter is preloaded with perfumes and/or odor neutralizing substances, for absorbing gasses passing through the filter to render them less noxious. Potentially, filtering slows the release of gasses so that external concentrations of odorants are less noticeable to the ostomate and/or to others.

Reference is now made to FIGS. 21C-21E, which schematically illustrate positioning of a filter 2103 relative to folded structure of an ostomy pouch 2150, according to some exemplary embodiments of the invention.

In some embodiments, a nearly folded ostomy pouch 2150 comprises a remaining first flap 2110, and second flap 2112 (for example, a top flap and a bottom flap), foldable over a central panel region attached to a mounting element 2109 to complete the folding of the package. In some embodiments of the invention, filter element 2103 is attached to one of the walls of the material comprised in the pouch. As shown, the filter element is attached to the wall nearest to the ostomate in the pouch-deployed configuration, to the panel immediately above the mounting element-attached panel, near the bottom of that panel, but spaced from the panel fold-crease edges by, for example, 2-4 mm, 3-6 mm, 5-10 mm, or a distance in another range having the same, intermediate, larger and/or smaller bounds.

In some embodiments of the invention, folding flap 2110 over (FIG. 21D) results in the filter being brought to the front of the package, and positioned near its top. Optionally, this is done after flap 2112 is folded over. As shown, flap 2112 is folded (optionally) up over flap 2110. The resulting package (FIG. 21E) positions the filter close to a surface of flap 2112 which potentially occludes vent aperture 2105. In some embodiments, the risk of occlusion is reduced by the positioning of the filter 2103 (and thus vent aperture 2105) near the free end of flap 2112. In some embodiments, a crimp region 2120 is formed by the folding over of region 2110. In some embodiments, the crimp comprises an at least partial barrier to the intrusion of solid and/or fluid waste to the pouch compartment comprised in the panel containing the filter 2103. Barrier properties of some embodiments of the crimp region 2120 include, for example, that it comprises a restriction, and that it is located at the top of the pouch package, such that waste must first be pushed upward before it can descend to potentially foul the filter. Stomal gas, in contrast, potentially is free to diffuse into the region of the filter 2103, being relatively unaffected in its movement by the direction of gravity and/or the partial restriction comprised in crimp region 2120.

Reference is now made to FIGS. 22A-22B, which show different configurations of filters 2201, 2203, 2207, 2205, 2215 attached to pouch embodiments 2202, 2204, according to some exemplary embodiments of the invention.

In some embodiments, a filter element has any desired shape appropriate to the constraints of the panel within which it is placed, for example, round filter element 2201, square filter element 2203, or rectangular filter elements 2205, 2207, 2215. Constraints comprise, for example, being sized and shaped such that crease edges are avoided. Placement within the panel, in some embodiments, is such the filter outlet aperture is away from a region likely to be blocked, and/or such that the filter inlet aperture is raised up relative to potential accumulation of fluid or solid within the collapsed structure of the pouch.

In some embodiments of the invention, the pouch panel in which the filter 2203, 2205, 2207 is placed is chosen to be one crease away from the inlet to the pouch. This allows a potential advantage of separation of flatus from other waste material by the resistance of a crease, without increasing resistance to the point where flatus itself is blocked. Nevertheless, in some embodiments, a filter element is placed two or more creases beyond a pouch inlet (for example, filter elements 2201, 2215). This potentially increases the separating function which helps protect the filter inlet regions. Potentially, it slows the rate at which flatus escapes the filter element 2215, 2201. Potentially, this in turn improves stench control for continuous release, though it may also increase stomal pressure and/or reliance on manual venting.

The panel, in some embodiments, is above (filter 2205), below (filter 2215), and/or to the side (filter 2207) of the inlet aperture. In some embodiments, a plurality of filter elements is provided, for example, both of the marked side filter elements 2207.

Reference is now made to FIGS. 22C-22D, which show filter elements 2205, 2215 having at least one side protected from waste contamination by a sealing element 2212, according to some exemplary embodiments of the invention.

In some embodiments a filter element 2205, 2215 has a preferred orientation conferred by sealing of one or more sides from which waste leakage is deemed most likely to arrive. Thus, for example, filter element 2205 is positioned with the long side facing the pouch inlet sealed. The short sides are sealed as well, in some embodiments.

In some embodiments, sealing allows an outlet aperture 2210 to be positioned closer to a sealed side, without shortening the shortest available path from filter intake to filter outlet. In some embodiments, this allows more thorough (if potentially slower) filtering from a given size of filter element. In some embodiments, it allows reduction of the amount of filter material used. A potential advantage of this is cost savings, another potential advantage is reduced effect on pouch package size, and yet another potential advantage is placement of the outlet aperture nearer to the edge of the panel (in a less occluded position, for example), without increasing interference with panel creasing.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An ostomy appliance to provide continence to a stoma, comprising: a collapsed waste collection pouch for receiving stomal waste, the pouch having an aperture attached to a proximal end of said ostomy appliance and sized to receive waste therefrom;
   a closure region of said pouch comprising a surface extending substantially parallel and proximal to said aperture;
   wherein
   the limits of said closure region are defined by folds;
   said folds restrict waste reaching said aperture from moving past said closure region into the remainder of the pouch, when attached as a collapsed pouch to said ostomy appliance; and
   wherein said pouch comprises a folded configuration having a polygonal cross-section comprising a shape formed by folds comprising at least three crease lines, and wherein said polygonal cross-section comprises a shape formed by folds comprising at least two crease lines at an angle to said at least three crease lines.

2. The ostomy appliance of claim 1, wherein said polygonal cross-section is less than 50% of the enclosed area of the unfolded pouch.

3. The ostomy appliance of claim 2, wherein said polygonal cross-section is less than 25% of the enclosed area of the unfolded pouch.

4. The ostomy appliance of claim 1, wherein at least one region of said pouch outside said closure region extends substantially parallel to said aperture and across at least 80% of said closure region.

5. The ostomy appliance of claim 1, wherein a plurality of separate regions of said pouch, each separated from said closure region by at least one of said folds, are folded to overlap one another.

6. The ostomy appliance of claim 1, wherein said pouch comprises at least two plies of a membranous material, secured to one another at the edges to create a sealed receptacle for receiving waste.

7. The ostomy appliance of claim 1, wherein said folded configuration comprises a predetermined number of layered panels of pouch material lying substantially perpendicular to a proximal-distal axis.

8. The ostomy appliance of claim 1, wherein said closure region surface comprises a substantially flat wall proximal to said proximal end.

9. The ostomy appliance of claim 8, wherein said substantially flat wall proximal to said proximal end comprises a smooth region which occupies a predetermined distance from a distal floor of said ostomy appliance.

10. The ostomy appliance of claim 9, wherein said predetermined distance comprises a stomal height, adjusted by a predetermined spacing.

11. The ostomy appliance of claim 10, wherein said predetermined spacing is greater than 0 mm, and less than 5 mm.

12. The ostomy appliance of claim 10, wherein said predetermined spacing is greater than 0 mm, and less than 2 mm.

13. The ostomy appliance of claim 1, wherein said polygonal cross-section is fitted to the shape of a recess in a component of said ostomy appliance; or
   wherein said polygonal cross-section comprises a shape formed by folds comprising a plurality of substantially parallel crease lines; or
   wherein said polygonal cross-section comprises a shape formed by folds comprising at least two crease lines substantially at relative angles characteristic of right quadrilateral, regular pentagon, or regular hexagon.

14. The ostomy appliance of claim 13, wherein said recess is fitted to the depth of said collapsed waste collection pouch, such that the collapsed pouch is held with layers compressed against one another.

15. The ostomy appliance of claim 13, wherein said component of said ostomy appliance is a pouch restraint.

16. The ostomy appliance of claim 13, wherein said polygonal cross-section comprises a shape formed by folds comprising at least two crease lines substantially at relative angles characteristic of right quadrilateral, regular pentagon, or regular hexagon, and wherein said at least two crease lines comprise intersections in the pouch.

17. The ostomy appliance of claim 1, wherein said folds comprise bends in opposite enclosing surfaces of said pouch, such that said enclosing surfaces are pressed into continuous contact with one another along the extent of said folds.

18. The ostomy appliance of claim 17, wherein said pouch is held into a compact configuration such that said folds are pressed together, such that there is insufficient volume beyond them for said waste to move into.

19. The ostomy appliance of claim 1, wherein said at least three crease lines are substantially parallel.

20. The ostomy appliance of claim 1, wherein said polygonal cross-section comprises a shape formed by folds comprising a plurality of substantially parallel crease lines, and wherein said polygonal cross-section comprises a shape formed by folds comprising at least one crease line at a substantially right angle to said substantially parallel crease lines.

21. The ostomy appliance of claim 1, wherein said pouch is restrained from deployment by the folded structure of said pouch interfering with its own unfolding.

22. The ostomy appliance of claim 21, wherein said interfering comprises a first fold being restrained from opening before a second fold opens; or
wherein said interfering comprises distributing forces acting to deploy the pouch such that non-zero magnitude opening forces at a fold are insufficient to overcome forces that act to close the fold.

23. The ostomy appliance of claim 1, wherein said collapsed waste collection pouch is folded to present a proximal surface comprising (1) a face of a single folded panel or (2) a region which is adapted to be manipulated to deploy the pouch for filling with waste.

24. The ostomy appliance of claim 23, wherein said collapsed waste collection pouch is folded to present a proximal surface comprising a region which is adapted to be manipulated to deploy the pouch for filling with waste, and wherein pulling on a proximal portion of said folded pouch in a single direction deploys the pouch for filling with waste.

25. The ostomy appliance of claim 1, wherein said folded configuration comprises at least one fold following a crease-line which runs substantially at an angle between parallel to and perpendicular to an axis of the bag which follows the direction along which the bag hangs when deployed.

26. The ostomy appliance of claim 1, wherein the proximal end of said ostomy appliance to which said pouch is attached comprises an ostomy appliance cap.

27. The ostomy appliance of claim 1, further comprising a filter element attached to the material of said collapsed waste collection pouch.

28. The ostomy appliance of claim 27, wherein the filter element is adapted to release flatus gas while the ostomy pouch is collapsed, and wherein the folds restrict the access of solid waste to the filter element.

29. The ostomy appliance of claim 1, wherein said polygonal cross-section comprises a shape formed by folds comprising at least four substantially parallel crease lines, and wherein said polygonal cross-section comprises a shape formed by folds comprising at least two crease lines at a substantially right angle to said at least four substantially parallel crease lines.

30. A method of deploying the waste collection pouch from the ostomy appliance of claim 1, wherein the ostomy appliance further comprises a pouch restraint, and wherein the method comprises: setting the pouch restraint to release the pouch for deployment at a
predetermined release pressure; and
automatically releasing said restraint at an actual intra-abdominal release pressure based on said predetermined release pressure.

31. A method of manufacturing an ostomy appliance of claim 1, comprising:
receiving a folding pattern for said waste collection pouch comprising crease lines and directions of folding therearound; and
folding the pouch according to said folding pattern.

32. A folded pouch adapted for use with an ostomy appliance to provide continence to a stoma, comprising:
a pouch body having an aperture configured to fit against a proximal end of said ostomy appliance and sized to receive waste therefrom;
a frame configured to attach to said ostomy appliance and fit said aperture thereto;
a closure region of said pouch body comprising a surface extending substantially parallel and proximal to said aperture;
wherein folding of said pouch restricts waste reaching said aperture from moving past said closure region into the remainder of the pouch body, when attached as a collapsed pouch to said ostomy appliance; and
wherein said pouch body comprises a folded configuration having a polygonal cross-section comprising a shape formed by folds comprising at least three crease lines, and wherein said polygonal cross-section comprises a shape formed by folds comprising at least two crease lines at an angle relative to said at least said three crease lines.

33. The folded pouch of claim 32, wherein said folding comprises folds at an angle deviating from substantially parallel and substantially perpendicular to a direction of force applied when said pouch is manipulated to be deployed for filling with waste.

34. The folded pouch of claim 32, wherein said polygonal cross-section comprises a shape formed by folds comprising at least four substantially parallel crease lines, and wherein said polygonal cross-section comprises a shape formed by folds comprising at least two crease lines at a substantially right angle to said at least four substantially parallel crease lines.

35. An ostomy cap for sealing a surgical stoma comprising:
a folded ostomy pouch; and
a pressure-releasing pouch restraint positioned to prevent the pouch from deploying from its collapsed state below a selected threshold of pressure received from within the abdominal cavity; wherein the folding pattern of the folded ostomy pouch is adjustable to one of a plurality of predetermined folding patterns; and
said selected threshold of pressure is changeable, according to said folding pattern.

* * * * *